(12) United States Patent
Brown et al.

(10) Patent No.: US 8,809,333 B2
(45) Date of Patent: Aug. 19, 2014

(54) IMIDAZOLE, PYRAZOLE, AND TRIAZOLE DERIVATIVES USEFUL AS ANTIBACTERIAL AGENTS

(75) Inventors: Matthew Frank Brown, Stonington, CT (US); Jinshan Michael Chen, Madison, CT (US); Michael Joseph Melnick, Portage, MI (US); Justin Ian Montgomery, Ledyard, CT (US); Usa Reilly, West Haven, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/110,165

(22) PCT Filed: Mar. 27, 2012

(86) PCT No.: PCT/IB2012/051456
§ 371 (c)(1),
(2), (4) Date: Oct. 7, 2013

(87) PCT Pub. No.: WO2012/137099
PCT Pub. Date: Oct. 11, 2012

(65) Prior Publication Data
US 2014/0038975 A1     Feb. 6, 2014

Related U.S. Application Data

(60) Provisional application No. 61/473,370, filed on Apr. 8, 2011.

(51) Int. Cl.
| | | |
|---|---|---|
| *C07D 231/12* | (2006.01) | |
| *C07D 233/61* | (2006.01) | |
| *C07D 249/06* | (2006.01) | |
| *C07D 403/04* | (2006.01) | |
| *C07D 413/04* | (2006.01) | |
| *C07D 413/10* | (2006.01) | |
| *C07D 417/04* | (2006.01) | |
| *C07D 405/04* | (2006.01) | |
| *A61K 31/4192* | (2006.01) | |

(52) U.S. Cl.
CPC ............ *C07D 413/10* (2013.01); *C07D 413/04* (2013.01); *C07D 231/12* (2013.01); *C07D 249/06* (2013.01); *C07D 403/04* (2013.01); *C07D 405/04* (2013.01); *A61K 31/4192* (2013.01); *C07D 233/61* (2013.01); *C07D 417/04* (2013.01)
USPC ...... 514/249; 514/255.05; 514/359; 514/374; 514/399; 514/406; 544/353; 544/405; 548/235; 548/255; 548/338.5; 548/375.1

(58) Field of Classification Search
None
See application file for complete search history.

(56) References Cited

U.S. PATENT DOCUMENTS

| | | | |
|---|---|---|---|
| 4,769,461 A | 9/1988 | Musser et al. | |
| 5,110,831 A | 5/1992 | Magolda et al. | |
| 6,673,965 B1 | 1/2004 | Ward et al. | |
| 2005/0119305 A1 | 6/2005 | Naka et al. | |
| 2006/0247271 A1 | 11/2006 | Bruton | |
| 2006/0276409 A1 | 12/2006 | Hunter et al. | |
| 2008/0085893 A1 | 4/2008 | Yang et al. | |
| 2008/0234297 A1 | 9/2008 | Qian et al. | |
| 2011/0178042 A1* | 7/2011 | Brown et al. | 514/92 |
| 2012/0232083 A1 | 9/2012 | Reilly et al. | |
| 2012/0258948 A1 | 10/2012 | Brown et al. | |

FOREIGN PATENT DOCUMENTS

| | | |
|---|---|---|
| EP | 1437349 | 7/2004 |
| WO | 0130747 | 5/2001 |
| WO | 2004062601 | 7/2004 |
| WO | 2004067502 | 8/2004 |
| WO | 2006063281 | 6/2006 |
| WO | 2006118155 | 11/2006 |
| WO | 2006124897 | 11/2006 |
| WO | 2007069020 | 6/2007 |
| WO | 2008045671 | 4/2008 |
| WO | 2008105515 | 9/2008 |
| WO | 2008115262 | 9/2008 |
| WO | 2009008905 | 1/2009 |
| WO | 2010017060 | 2/2010 |
| WO | 2010024356 | 3/2010 |
| WO | 2010031750 | 3/2010 |
| WO | 2010032147 | 3/2010 |
| WO | 2010100475 | 9/2010 |
| WO | 2011073845 | 6/2011 |
| WO | 2012120397 | 9/2012 |
| WO | 2012137094 | 10/2012 |
| WO | 2012137099 | 10/2012 |

OTHER PUBLICATIONS

"455710(Antibiotics and Antibacterial Drugs)", Annual Drug Data Report, Jan. 1, 2007, p. 629, 29(7).
Apfel, Christian et al., "Hydroxamic Acid Derivatives as Potent Peptide Deformylase Inhibitors and Antibacterial Agents", Journal of Medicinal Medicinal Chemistry, Jun. 15, 2000, pp. 2324-2331, 43(12).
Barlaam, B., et al., "New Alpha-Substituted Succinate-Based Hydroxamic Acids As TNFALPHA Convertase Inhibitors", Journal of Medicinal Chemistry, Jan. 1, 1999, pp. 4890-4908, 42(23).

(Continued)

*Primary Examiner* — Kamal Saeed

(74) *Attorney, Agent, or Firm* — John A. Wichtowski; James T. Wasicak

(57) ABSTRACT

The present invention is directed to a new class of hydroxamic acid derivatives, their use as LpxC inhibitors and, more specifically, their use to treat bacterial infections.

28 Claims, No Drawings

(56) References Cited

OTHER PUBLICATIONS

Brown, Matthew F., et al., "Potent Inhibitors of LpxC for the Treatment of Gram-Negative Infections", Journal of Medicinal Chemistry, Dec. 18, 2011, pp. 914-923, 55(18).
Clements, J.M., et al., "Antimicrobial Activities and Characterization of Novel Inhibitors of LpxC", Antimicrobial Agents and Chemotherapy, American Society for Microbiology, Jun. 1, 2002, pp. 1793-1799, 46(6).
Conreaux, D., et l., "A practical procedure for the selective N-alkylation of 4-alkoxy-2-pyridones and its use in a sulfone-mediated synthesis of N-methyl-4-methoxy-2-pyridone", Tetrahedron Letters, 2005, pp. 7917-7920, 46(46).
Dube, Peter H., et al., "Protective Role of Interleukin-6 During Yersinia enterocolitica Infection Is Mediated through the Modulation of Inflammatory Cytokines", Infection and Immunity, Jun. 2004, pp. 3561-3570, 72(6).
English Translation of International Patent Application WO 2008/105515 publication date Sep. 4, 2008.
Gennadios, H.A., et al., "Mechanistic Inferences from the Binding of Ligands to LpxC, a Metal-Dependent Deacetylase", Biochemistry, 2006, pp. 7940-7948, 45(26).
Gipstein, E., et al., "Synthesis and Polymerization of Alkyl.α-(Alkylsulfonyl)acrylates1a", Journal of Organic Chemistry, 1980, pp. 1486-1489, 45(8).
Imanishi, Jiro, "Expression of Cytokines in Bacterial and Viral Infections and Their Biochemical Aspects", The Japanese Biochemical Society, 2000, pp. 525-530, 127(4).
International Patent Application No. PCT/IB2009/053809, PCT International Search Report (ISR), mailed Apr. 4, 2010, 7 pages.
International Patent Application No. PCT/IB2009/053809, PCT Written Opinion, mailed Apr. 4, 2010, 7 pages.
International Patent Application No. PCT/IB2010/055596, publication No. WO 2011/073845,Search Report and Written Opinion mailed Mar. 23, 2011, 15 pages.
International Patent Application No. PCT/IB2012/050812 PCT International Search Report (ISR) and Written Opinion mailed Apr. 23, 2012, pp. 4.
International Patent Application No. PCT/IB2012/051406 PCT International Search Report (ISR) and Written Opinion mailed Oct. 7, 2012, 5 pages.
IUPAC, E.D., et al., "alkyl groups", Compendium of Chemical Terminology: IUPAC Recommendations; http://www.iupac.org/goldbook/A00228.pdf Jan. 1, 1997.
Kirsch, R, et al., "Super-Fluorinated Liquid Crystals: Towards the Limits of Polarity", European Journal Organic Chemistry, Jul. 2008, pp. 3479-3487, 2008(20).
Kwok, A., et al., "Helicobacter Pylori Eradication Therapy: Indications, efficacy and Safety", Expert Opinion Drug Safety, May 2008, pp. 271-281, 7(3).
Product Label—ACTEMRA* (toclizumab) Injection, for intravenous infusion; revised Apr. 2013, pp. 1-35.
Qu, W., et al., "Quick Assembly of 1,4-Diphenyltriazoles as Probes Targeting β-Amyloid Aggregates in Alzheimer's . Disease", Journal of Medicinal Chemistry, 2007, pp. 3380-3387, 50(14).
Raetz, Christian, H., et al., "Lipid A Modification Systems in Gram-Negative Bacteria", Annual Review Biochemistry, 2007, pp. 295-329, vol. 76.
Rice, Louis B., "Unmet Medical Needs in Antibacterial Therapy", Biochemical Pharmacology, Mar. 30, 2006, pp. 991-995, 71(7).
Wang, Y., et al., "A novel and efficient synthesis of terminal arylacetylenes via Sonogashira coupling reactions catalysed by MCM-41-supported bidentate phosphine palladium (0) complex", Journal of Chemical Research, Dec. 2007, pp. 728-732, 2007(12).
Hennigan, Stephanie, et al., "Interleukin-6 Inhibitors in the Treatment of Rheumatoid Arthritis", Therapeutics and Clinical Risk Management, 2008, pp. 767-775, 4(4).
Antinfective Therapy, Antiboitics and Antibacterial Drugs, "455710" (Vicuron Pharmaceuticals), Drug Data Report, Jul./Aug. 2007, p. 629, 29(7).
IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata: updates compiled by A. Jenkins. ISBN 0-9678550-9-8. doi:10.1351/goldbook. Last update: Feb. 24, 2014; version: 2.3.3.

* cited by examiner

IMIDAZOLE, PYRAZOLE, AND TRIAZOLE DERIVATIVES USEFUL AS ANTIBACTERIAL AGENTS

This application is a national stage application under 35 U.S.C. 371 of PCT/IB2012/051456, filed on Mar. 27, 2012, which claims the benefit of U.S. Provisional Patent Application No. 61/473,370, filed on Apr. 8, 2011, the disclosures of which are hereby incorporated by reference in their entirety.

FIELD OF THE INVENTION

This invention relates to novel hydroxamic acid derivatives. The invention also relates to methods of using such compounds in the treatment of bacterial infections (especially Gram-negative infections) and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Enterobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most Gram-negative bacteria. LpxC [UDP-3-O—(R-3-hydroxymyristoyl)-N-acetylglucosamine deacetylase] is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC with low nM affinity have been reported (Biochemistry 45: 7940-48, 2006).

SUMMARY OF THE INVENTION

A new class of LpxC inhibitors has been discovered. These compounds, or their pharmaceutically acceptable salts, can be represented by Formula I below:

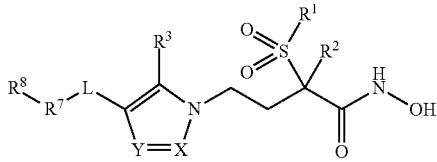

Formula I wherein
$R^1$ is $(C_1-C_3)$alkyl;
$R^2$ is hydrogen or $(C_1-C_3)$alkyl;
$R^3$ is hydrogen or $(C_1-C_3)$alkyl;
X is N or $CR^4$;
Y is N or $CR^4$;
$R^4$ is hydrogen or $(C_1-C_3)$alkyl;
L is a bond, $(C_2-C_6)$alkenylene, $(C_1-C_6)$alkylene, $(C_2-C_6)$alkynylene, —$(CH_2)_nO$—$(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$—, or —$(CH_2)_nNR^5CO(CH_2)_p$—; $R^5$ and $R^6$ are independently hydrogen, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl, or formyl;
n is 0, 1, 2, 3, or 4;
p is 0, 1, 2, 3, or 4;
$R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_3-C_8)$cycloalkyl-$NR^5$—, $(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocycle, $(C_3-C_{13})$heterocycleoxy, $(C_3-C_{13})$heterocyclethio, $(C_3-C_{13})$heterocycle-$NR^5$—, hydroxy$(C_1-C_{10})$alkyl, mercapto$(C_1-C_6)$alkyl, $(NR^5R^6)$alkyl, or $(NR^5R^6)$carbonyl; and
$R^8$ is absent, $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocycle, or $(C_3-C_{13})$heterocycle$(C_1-C_6)$alkyl.

The compounds of Formula I exhibit antibacterial activity, especially against Gram-negative organisms. They may be used to treat bacterial infections in mammals, especially humans. The compounds may also be used for veterinary applications, such as treating infections in livestock and companion animals.

The compounds of Formula I are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation, cream/ointments for topical, otic or ophthalmic use, and solutions/suspensions for oral ingestion.

DETAILED DESCRIPTION OF THE INVENTION

The headings within this document are only being utilized to expedite its review by the reader. They should not be construed as limiting the invention or claims in any manner.

In one embodiment, the present invention provides compounds of Formula I wherein $R^1$ is $(C_1-C_3)$alkyl; $R^2$ is $(C_1-C_3)$alkyl; $R^3$ is hydrogen or $(C_1-C_3)$alkyl; X is N; Y is N or $CR^4$; $R^4$ is hydrogen or $(C_1-C_3)$alkyl; L is a bond, $(C_2-C_6)$alkynylene, —$(CH_2)_nO$—$(CH_2)_p$—, or —$(CH_2)_nS(CH_2)_p$—; n is 0, 1, or 2; p is 0, 1, or 2; $R^7$ is $(C_1-C_6)$alkyl, $(C_6-C_{12})$aryl, cyano, $(C_5-C_8)$cycloalkenyl, $(C_3-C_8)$cycloalkyl, $(C_5-C_{12})$heteroaryl, or $(C_3-C_{13})$heterocycle; and $R^8$ is absent, $(C_6-C_{12})$aryl, $(C_6-C_{12})$aryl$(C_1-C_6)$alkyl, $(C_3-C_8)$cycloalkyl, or $(C_5-C_{12})$heteroaryl.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond, $(C_2-C_6)$alkynylene, —$(CH_2)_nO$—$(CH_2)_p$—, or —$(CH_2)_nS(CH_2)_p$—; n is 0, 1, or 2; p is 0, 1, or 2; $R^7$ is $(C_6-C_{12})$aryl, wherein the $(C_6-C_{12})$aryl is dihydroindenyl, naphthyl, phenyl, or tetrahydronaphthalenyl, wherein each is optionally substituted with 1, 2, or 3 substituents that are independently $(C_1-C_6)$alkoxy, $(C_1-C_6)$alkyl, $(C_1-C_6)$alkylthio, cyano, ethylenedioxy, halo$(C_1-C_6)$alkoxy, halo$(C_1-C_6)$alkyl, halogen, hydroxy, or oxo; and $R^8$ is absent, $(C_3-C_8)$cycloalkyl, or $(C_5-C_{12})$heteroaryl.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond, —C≡C—, —O$(CH_2)$—, or —S$(CH_2)$—; $R^7$ is $(C_6-C_{12})$aryl, wherein the $(C_6-C_{12})$aryl is dihydroindenyl, naphthyl, phenyl, or tetrahydronaphthalenyl, wherein each is optionally substituted with 1, 2, or 3 substituents that are independently $(C_1-C_6)$alkoxy, $(C_1-C_6)$alkyl, $(C_1-C_6)$alkylthio, cyano, ethylenedioxy, halo$(C_1-C_6)$alkoxy, halo$(C_1-C_6)$alkyl, halogen, hydroxy, or oxo; and $R^8$ is absent, $(C_3-C_8)$cycloalkyl, or $(C_5-C_{12})$heteroaryl wherein the $(C_5-C_{12})$heteroaryl is isoxazolyl, oxazolyl, pyrazolyl, pryimidinyl, or thiadiazoyl wherein each is optionally substituted with 1 substituent that is $(C_1-C_6)$alkyl or $NZ^1Z^2$ wherein $Z^1$ and $Z^2$ are hydrogen, and wherein the $(C_3-C_8)$cycloalkyl is cyclopropyl optionally substituted with 1 substituent that is cyano.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond; $R^7$ is $(C_5-C_8)$cycloalkenyl or $(C_3-C_8)$cycloalkyl, wherein the $(C_5-C_8)$cycloalkenyl is cyclohexenyl, and wherein the $(C_3-C_8)$cycloalkyl is cyclohexyl or cyclopentyl; and $R^8$ is absent.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond, $(C_2-C_6)$alkynylene, —$(CH_2)_nO$—$(CH_2)_p$—, or —$(CH_2)_nS(CH_2)_p$—; n is 0, 1, or 2; p is 0, 1, or 2; $R^7$ is $(C_5-C_{12})$heteroaryl wherein the $(C_5-C_{12})$heteroaryl is benzoxazolyl, benzothiazolyl, indolyl, imidazolyl, isoquinolinyl, oxazolyl, pyrazinyl, pyrazolyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl where $Z^1$ and $Z^2$ are hydrogen; and $R^8$ is absent, $(C_6-C_{12})$aryl, or $(C_6-C_{12})$aryl$(C_1-C_6)$alkyl.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond; $R^7$ is $(C_5-C_{12})$heteroaryl wherein the $(C_5-C_{12})$heteroaryl is benzoxazolyl, benzothiazolyl, indolyl, imidazolyl, isoquinolinyl, oxazolyl, pyrazinyl, pyrazolyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl where $Z^1$ and $Z^2$ are hydrogen; and $R^8$ is absent, $(C_6-C_{12})$aryl, or $(C_6-C_{12})$aryl$(C_1-C_6)$alkyl, wherein the $(C_6-C_{12})$aryl$(C_1-C_6)$alkyl is benzyl, and wherein the $(C_6-C_{12})$aryl is phenyl optionally substituted with 1 substituent that is halogen.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond; $R^7$ is $(C_3-C_{13})$heterocycle wherein the $(C_3-C_{13})$heterocycle is 2,3-dihydrobenzofuranyl; and $R^8$ is absent.

In another embodiment, the present invention provides compounds of Formula I wherein $R^1$ is methyl; $R^2$ is methyl; $R^3$ is hydrogen or methyl; X is N; Y is N or $CR^4$; $R^4$ is hydrogen or methyl; L is a bond; $R^7$ is $(C_1-C_6)$alkyl or cyano; and $R^8$ is absent.

In another embodiment, the present invention provides compounds of Formula I wherein $R^1$ is $(C_1-C_3)$alkyl; $R^2$ is hydrogen or $(C_1-C_3)$alkyl; $R^3$ is hydrogen or $(C_1-C_3)$alkyl; X is N; Y is N; L is a bond, $(C_2-C_6)$alkenylene, $(C_1-C_6)$alkylene, $(C_2-C_6)$alkynylene, —$(CH_2)_nO$—$(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$—, or —$(CH_2)_nNR^5CO(CH_2)_p$—; $R^5$ and $R^6$ are independently hydrogen, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl, or formyl; n is 0, 1, 2, 3, or 4; p is 0, 1, 2, 3, or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_3-C_8)$cycloalkyl-$NR^5$—, $(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocycle, $(C_3-C_{13})$heterocycleoxy, $(C_3-C_{13})$heterocyclethio, $(C_3-C_{13})$heterocycle-$NR^5$—, hydroxy$(C_1-C_{10})$alkyl, mercapto$(C_1-C_6)$alkyl, $(NR^5R^6)$alkyl, or $(NR^5R^6)$carbonyl; and $R^8$ is absent, $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocycle, or $(C_3-C_{13})$heterocycle$(C_1-C_6)$alkyl.

In another embodiment, the present invention provides compounds of Formula I wherein $R^1$ is $(C_1-C_3)$alkyl; $R^2$ is hydrogen or $(C_1-C_3)$alkyl; $R^3$ is hydrogen or $(C_1-C_3)$alkyl; X is N; Y is N; L is a bond, —$(CH_2)_nO$—$(CH_2)_p$—, or —$(CH_2)_nS(CH_2)_p$—; n is 0, 1, or 2; p is 0, 1, or 2; $R^7$ is $(C_6-C_{12})$aryl; and $R^8$ is absent.

In another embodiment, the present invention provides compounds of Formula I wherein $R^1$ is methyl; $R^2$ is methyl; $R^3$ is hydrogen or methyl; X is N; Y is N; L is a bond, —O$(CH_2)$—, or —S$(CH_2)$—; $R^7$ is $(C_6-C_{12})$aryl wherein the $(C_6-C_{12})$aryl is naphthyl or phenyl where each is optionally substituted with 1, 2, or 3 substituents that are independently $(C_1-C_6)$alkoxy, $(C_1-C_6)$alkyl, $(C_1-C_6)$alkylthio, halo$(C_1-C_6)$alkyl, or halogen; and $R^8$ is absent.

In another embodiment, the present invention provides compounds of Formula I wherein $R^1$ is methyl; $R^2$ is methyl; $R^3$ is hydrogen; X is N; Y is N; L is a bond, —O$(CH_2)$—, or —S$(CH_2)$—; $R^7$ is $(C_6-C_{12})$aryl wherein the $(C_6-C_{12})$aryl is naphthyl or phenyl where each is optionally substituted with 1, 2, or 3 substituents that are independently $(C_1-C_6)$alkoxy, $(C_1-C_6)$alkyl, $(C_1-C_6)$alkylthio, halo$(C_1-C_6)$alkyl, or halogen; and $R^8$ is absent.

In another embodiment, the present invention provides compounds of Formula I wherein $R^1$ is $(C_1-C_3)$alkyl; $R^2$ is hydrogen or $(C_1-C_3)$alkyl; $R^3$ is hydrogen or $(C_1-C_3)$alkyl; X is N; Y is $CR^4$; $R^4$ is hydrogen or $(C_1-C_3)$alkyl; L is a bond, $(C_2-C_6)$alkenylene, $(C_1-C_6)$alkylene, $(C_2-C_6)$alkynylene, —$(CH_2)_nO$—$(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$—, or —$(CH_2)_nNR^5CO(CH_2)_p$—; $R^5$ and $R^6$ are independently hydrogen, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl, or formyl; n is 0, 1, 2, 3, or 4; p is 0, 1, 2, 3, or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_3-C_8)$cycloalkyl-$NR^5$—, $(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocycle, $(C_3-C_{13})$heterocycleoxy, $(C_3-C_{13})$heterocyclethio, $(C_3-C_{13})$heterocycle-$NR^5$—, hydroxy$(C_1-C_{10})$alkyl, mercapto$(C_1-C_6)$alkyl, $(NR^5R^6)$alkyl, or $(NR^5R^6)$carbonyl; and $R^8$ is absent, $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocycle, or $(C_3-C_{13})$heterocycle$(C_1-C_6)$alkyl.

In another embodiment, the present invention provides compounds of Formula I wherein $R^1$ is $(C_1-C_3)$alkyl; $R^2$ is $(C_1-C_3)$alkyl; $R^3$ is hydrogen; X is N; Y is $CR^4$; $R^4$ is hydrogen or $(C_1-C_3)$alkyl; L is a bond or $(C_2-C_6)$alkynylene; $R^7$ is $(C_1-C_6)$alkyl, $(C_6-C_{12})$aryl, cyano, $(C_5-C_8)$cycloalkenyl, $(C_3-C_8)$cycloalkyl, $(C_5-C_{12})$heteroaryl, or $(C_3-C_{13})$heterocycle; and $R^8$ is absent, $(C_6-C_{12})$aryl, $(C_6-C_{12})$aryl$(C_1-C_6)$alkyl, $(C_3-C_8)$cycloalkyl, or $(C_5-C_{12})$heteroaryl.

In another embodiment, the present invention provides compounds of Formula I wherein $R^1$ is methyl; $R^2$ is methyl; $R^3$ is hydrogen; X is N; Y is $CR^4$; $R^4$ is hydrogen or methyl; L is a bond or —C≡C—; $R^7$ is $(C_6-C_{12})$aryl; and $R^8$ is absent, $(C_3-C_8)$cycloalkyl, or $(C_5-C_{12})$heteroaryl.

In another embodiment, the present invention provides compounds of Formula I wherein $R^1$ is methyl; $R^2$ is methyl; $R^3$ is hydrogen; X is N; Y is $CR^4$; $R^4$ is hydrogen or methyl; L is a bond or —C≡C—; $R^7$ is $(C_6-C_{12})$aryl wherein the $(C_6-C_{12})$aryl is dihydroindenyl, phenyl, or tetrahydronaphthalenyl wherein each is optionally substituted with 1, 2, or 3 substituents that are independently $(C_1-C_6)$alkoxy, $(C_1-C_6)$alkyl, cyano, ethylenedioxy, halo$(C_1-C_6)$alkoxy, halogen, hydroxy, or oxo; and $R^8$ is absent, $(C_3-C_8)$cycloalkyl, or $(C_5-C_{12})$heteroaryl.

In another embodiment, the present invention provides compounds of Formula I wherein $R^1$ is methyl; $R^2$ is methyl; $R^3$ is hydrogen; X is N; Y is $CR^4$; $R^4$ is hydrogen or methyl; L is a bond or —C≡C—; $R^7$ is $(C_6-C_{12})$aryl wherein the $(C_6-C_{12})$aryl is dihydroindenyl, phenyl, or tetrahydronaphthalenyl wherein each is optionally substituted with 1, 2, or 3 substituents that are independently $(C_1-C_6)$alkoxy, $(C_1-C_6)$alkyl, cyano, ethylenedioxy, halo$(C_1-C_6)$alkoxy, halogen, hydroxy, or oxo; and $R^8$ is absent, $(C_3-C_8)$cycloalkyl, or $(C_5-C_{12})$heteroaryl, wherein the $(C_3-C_8)$cycloalkyl is cyclopropyl optionally substituted with cyano, and wherein the $(C_5-C_{12})$heteroaryl is isoxazolyl, oxazolyl, pyrazolyl, pyrimidinyl, or thiadiazolyl wherein each is optionally substituted with 1 substituent that is $(C_1-C_6)$alkyl or $NZ^1Z^2$ wherein $Z^1$ and $Z^2$ are hydrogen.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_6-C_{12})$aryl wherein the $(C_6-C_{12})$aryl is dihydroindenyl, phenyl, or tetrahydronaphthalenyl wherein each is optionally substituted with 1, 2, or 3 substituents that are independently $(C_1-C_6)$alkoxy, $(C_1-C_6)$alkyl, cyano, ethylenedioxy, halo$(C_1-C_6)$alkoxy, halogen, hydroxy, or oxo; and $R^8$ is absent, $(C_3-C_8)$cycloalkyl, or $(C_5-C_{12})$heteroaryl, wherein the $(C_3-C_8)$cycloalkyl is cyclopropyl optionally substituted with cyano, and wherein the $(C_5-C_{12})$heteroaryl is isoxazolyl, oxazolyl, pyrazolyl, pyrimidinyl, or thiadiazolyl wherein each is optionally substituted with 1 substituent that is $(C_1-C_6)$alkyl or $NZ^1Z^2$ wherein $Z^1$ and $Z^2$ are hydrogen.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_5-C_{12})$heteroaryl; and $R^8$ is absent, $(C_6-C_{12})$aryl, or $(C_6-C_{12})$aryl$(C_1-C_6)$alkyl.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_5-C_{12})$heteroaryl wherein the $(C_5-C_{12})$heteroaryl is benzoxazolyl, benzothiazolyl, imidazolyl, indolyl, isoquinolinyl, pyrazinyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl wherein $Z^1$ and $Z^2$ are hydrogen; and $R^8$ is absent, $(C_6-C_{12})$aryl, or $(C_6-C_{12})$aryl$(C_1-C_6)$alkyl.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_5-C_{12})$heteroaryl wherein the $(C_5-C_{12})$heteroaryl is benzoxazolyl, benzothiazolyl, imidazolyl, indolyl, isoquinolinyl, pyrazinyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl wherein $Z^1$ and $Z^2$ are hydrogen; and $R^8$ is absent, $(C_6-C_{12})$aryl, or $(C_6-C_{12})$aryl$(C_1-C_6)$alkyl, wherein the $(C_6-C_{12})$aryl$(C_1-C_6)$alkyl is benzyl, and wherein the $(C_6-C_{12})$aryl is phenyl optionally substituted with 1 substituent that is halogen.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_1-C_6)$alkyl or cyano; and $R^8$ is absent.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_5-C_8)$cycloalkenyl or $(C_3-C_8)$cycloalkyl, wherein the $(C_5-C_8)$cycloalkenyl is cyclohexenyl, and wherein the $(C_3-C_8)$cycloalkyl is cyclohexyl or cyclopentyl; and $R^8$ is absent.

In another embodiment, the present invention provides compounds of Formula I wherein $R^1$ is methyl; $R^2$ is methyl; $R^3$ is hydrogen; X is N; Y is $CR^4$; $R^4$ is hydrogen; L is a bond; $R^7$ is $(C_3-C_{13})$heterocycle wherein $(C_3-C_{13})$heterocycle is 2,3-dihydrobenzofuranyl; and $R^8$ is absent.

In another embodiment, the present invention provides compounds of Formula I wherein $R^1$ is $(C_1-C_3)$alkyl; $R^2$ is hydrogen or $(C_1-C_3)$alkyl; $R^3$ is hydrogen or $(C_1-C_3)$alkyl; X is $CR^4$; Y is N; $R^4$ is hydrogen or $(C_1-C_3)$alkyl; L is a bond, $(C_2-C_6)$alkenylene, $(C_1-C_6)$alkylene, $(C_2-C_6)$alkynylene, —$(CH_2)_nO$—$(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$—, or —$(CH_2)_nNR^5CO(CH_2)_p$—; $R^5$ and $R^6$ are independently hydrogen, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl, or formyl; n is 0, 1, 2, 3, or 4; p is 0, 1, 2, 3, or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, ($C_3$-$C_8$)cycloalkyl, ($C_3$-$C_8$)cycloalkyloxy, ($C_3$-$C_8$)cycloalkylthio, ($C_3$-$C_8$)cycloalkyl-$NR^5$—, ($C_5$-$C_{12}$)heteroaryl, ($C_5$-$C_{12}$)heteroaryloxy, ($C_5$-$C_{12}$)heteroarylthio, ($C_5$-$C_{12}$)heteroaryl-$NR^5$—, ($C_3$-$C_{13}$)heterocycle, ($C_3$-$C_{13}$)heterocycleoxy, ($C_3$-$C_{13}$)heterocyclethio, ($C_3$-$C_{13}$)heterocycle-$NR^5$—, hydroxy($C_1$-$C_{10}$)alkyl, mercapto($C_1$-$C_6$)alkyl, ($NR^5R^6$)alkyl, or ($NR^5R^6$)carbonyl; and $R^8$ is absent, ($C_6$-$C_{12}$)aryl, ($C_6$-$C_{12}$)aryl($C_1$-$C_6$)alkyl, ($C_3$-$C_8$)cycloalkyl, ($C_3$-$C_8$)cycloalkyl($C_1$-$C_6$)alkyl, ($C_5$-$C_{12}$)heteroaryl, ($C_5$-$C_{12}$)heteroaryl($C_1$-$C_6$)alkyl, ($C_3$-$C_{13}$)heterocycle, or ($C_3$-$C_{13}$)heterocycle($C_1$-$C_6$)alkyl.

In another embodiment, the present invention provides compounds of Formula I wherein $R^1$ is ($C_1$-$C_3$)alkyl; $R^2$ is hydrogen or ($C_1$-$C_3$)alkyl; $R^3$ is hydrogen or ($C_1$-$C_3$)alkyl; X is $CR^4$; Y is N; $R^4$ is hydrogen; L is a bond; $R^7$ is ($C_6$-$C_{12}$)aryl; and $R^8$ is absent.

In another embodiment, the present invention provides compounds of Formula I wherein $R^1$ is ($C_1$-$C_3$)alkyl; $R^2$ is ($C_1$-$C_3$)alkyl; $R^3$ is hydrogen; X is $CR^4$; Y is N; $R^4$ is hydrogen; L is a bond; $R^7$ is ($C_6$-$C_{12}$)aryl; and $R^8$ is absent.

In another embodiment, the present invention provides compounds of Formula I wherein $R^1$ is methyl; $R^2$ is methyl; $R^3$ is hydrogen; X is $CR^4$; Y is N; $R^4$ is hydrogen; L is a bond; $R^7$ is ($C_6$-$C_{12}$)aryl; and $R^8$ is absent.

In another embodiment, the present invention provides pharmaceutical compositions comprising a compound of Formula I in admixture with at least one pharmaceutically acceptable excipient.

In another embodiment, the present invention provides methods of treating bacterial infections comprising administering to a patient in need of such treatment a therapeutically effect amount of a compound of Formula I.

In another embodiment, the present invention provides a medicament manufactured or prepared using a compound of Formula I for bacterial infections.

DEFINITIONS

As used throughout this application, including the claims, the following terms have the meanings defined below, unless specifically indicated otherwise. The plural and singular should be treated as interchangeable, other than the indication of number.

The term "($C_2$-$C_6$)alkenyl" as used herein, means a straight or branched chain hydrocarbon containing from 2 to 6 carbons and containing at least one carbon-carbon double bond. Representative examples of ($C_2$-$C_6$)alkenyl include, but are not limited to, ethenyl, 2-propenyl, 2-methyl-2-propenyl, 3-butenyl, 4-pentenyl, and 5-hexenyl.

The term "($C_2$-$C_6$)alkenylene" means a divalent group derived from a straight or branched chain hydrocarbon of from 2 to 6 carbon atoms containing at least one double bond. Representative examples of alkenylene include, but are not limited to, —CH=CH—, —CH=$CH_2CH_2$—, and —CH=C($CH_3$)$CH_2$—.

The term "($C_1$-$C_6$)alkoxy" as used herein, means a ($C_1$-$C_6$) alkyl group, as defined herein, appended to the parent molecular moiety through an oxygen atom. Representative examples of ($C_1$-$C_6$)alkoxy include, but are not limited to, methoxy, ethoxy, propoxy, 2-propoxy, butoxy, tert-butoxy, pentyloxy, and hexyloxy.

The term "($C_1$-$C_3$)alkoxy" as used herein, means a ($C_1$-$C_3$) alkyl group, as defined herein, appended to the parent molecular moiety through an oxygen atom. Examples of ($C_1$-$C_3$)alkoxy include methoxy, ethoxy, propoxy, and 2-propoxy (isopropoxy).

The term "($C_1$-$C_6$)alkoxy($C_1$-$C_6$)alkyl" as used herein, means a ($C_1$-$C_6$)alkoxy group, as defined herein, appended to the parent molecular moiety through a ($C_1$-$C_6$)alkyl group, as defined herein. Representative examples of ($C_1$-$C_6$)alkoxy ($C_1$-$C_6$)alkyl include, but are not limited to, tert-butoxymethyl, 2-ethoxyethyl, 2-methoxyethyl, and methoxymethyl.

The term "($C_1$-$C_6$)alkoxycarbonyl" as used herein, means a ($C_1$-$C_6$)alkoxy group, as defined herein, appended to the parent molecular moiety through a carbonyl group, as defined herein. Representative examples of ($C_1$-$C_6$)alkoxycarbonyl include, but are not limited to, methoxycarbonyl, ethoxycarbonyl, and tert-butoxycarbonyl.

The term "($C_1$-$C_6$)alkoxycarbonyl($C_1$-$C_6$)alkyl" as used herein, means a ($C_1$-$C_6$)alkoxycarbonyl group, as defined herein, appended to the parent molecular moiety through a ($C_1$-$C_6$)alkyl group, as defined herein. Representative examples of ($C_1$-$C_6$)alkoxycarbonyl($C_1$-$C_6$)alkyl include, but are not limited to, 3-methoxycarbonylpropyl, 4-ethoxycarbonylbutyl, and 2-tert-butoxycarbonylethyl.

The term "($C_1$-$C_6$)alkoxysulfonyl" as used herein, means a ($C_1$-$C_6$)alkoxy group, as defined herein, appended appended to the parent molecular moiety through a sulfonyl group, as defined herein. Representative examples of ($C_1$-$C_6$)alkoxysulfonyl include, but are not limited to, methoxysulfonyl, ethoxysulfonyl and propoxysulfonyl.

The term "($C_1$-$C_3$)alkyl" as used herein, means a straight or branched chain hydrocarbon containing from 1 to 3 carbon atoms. Examples of ($C_1$-$C_3$)alkyl include methyl, ethyl, n-propyl, and iso-propyl.

The term "($C_1$-$C_6$)alkyl" as used herein, means a straight or branched chain hydrocarbon containing from 1 to 6 carbon atoms. Representative examples of ($C_1$-$C_6$)alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "($C_1$-$C_6$)alkylcarbonyl" as used herein, means a ($C_1$-$C_6$)alkyl group, as defined herein, appended to the parent molecular moiety through a carbonyl group, as defined herein. Representative examples of ($C_1$-$C_6$)alkylcarbonyl include, but are not limited to, acetyl, 1-oxopropyl, 2,2-dimethyl-1-oxopropyl, 1-oxobutyl, and 1-oxopentyl.

The term "($C_1$-$C_6$)alkylcarbonyl($C_1$-$C_6$)alkyl" as used herein, means a ($C_1$-$C_6$)alkylcarbonyl group, as defined herein, appended to the parent molecular moiety through a ($C_1$-$C_6$)alkyl group, as defined herein. Representative examples of ($C_1$-$C_6$)alkylcarbonyl($C_1$-$C_6$)alkyl include, but are not limited to, 2-oxopropyl, 3,3-dimethyl-2-oxopropyl, 3-oxobutyl, and 3-oxopentyl.

The term "($C_1$-$C_6$)alkylcarbonyloxy" as used herein, means a ($C_1$-$C_6$)alkylcarbonyl group, as defined herein, appended to the parent molecular moiety through an oxygen atom. Representative examples of ($C_1$-$C_6$)alkylcarbonyloxy include, but are not limited to, acetyloxy, ethylcarbonyloxy, and tert-butylcarbonyloxy.

The term "($C_1$-$C_6$)alkylene" means a divalent group derived from a straight or branched chain hydrocarbon of from 1 to 6 carbon atoms. Representative examples of ($C_1$-$C_6$)alkylene include, but are not limited to, —$CH_2$—, —CH($CH_3$)—, —C($CH_3$)$_2$—, —$CH_2CH_2$—, —$CH_2CH_2CH_2$—, —$CH_2CH_2CH_2CH_2$—, —$CH_2CH(CH_3)CH_2$—, and —$CH_2CH_2CH_2CH_2CH_2CH_2$—.

The term "($C_1$-$C_6$)alkylsulfinyl" as used herein, means an ($C_1$-$C_6$)alkyl group, as defined herein, appended to the parent molecular moiety through a sulfinyl group, as defined herein. Representative examples of ($C_1$-$C_6$)alkylsulfinyl include, but are not limited to, methylsulfinyl and ethylsulfinyl.

The term "$(C_1-C_6)$alkylsulfonyl" as used herein, means an $(C_1-C_6)$alkyl group, as defined herein, appended to the parent molecular moiety through a sulfonyl group, as defined herein. Representative examples of $(C_1-C_6)$alkylsulfonyl include, but are not limited to, methylsulfonyl and ethylsulfonyl.

The term "$(C_1-C_6)$alkylsulfonyl$(C_1-C_6)$alkyl" as used herein, means a $(C_1-C_6)$alkylsulfonyl group, as defined herein, appended to the parent molecular moiety through a $(C_1-C_6)$alkyl group, as defined herein.

The term "$(C_1-C_6)$alkylthio" as used herein, means a $(C_1-C_6)$alkyl group, as defined herein, appended to the parent molecular moiety through a sulfur atom. Representative examples of $(C_1-C_6)$alkylthio include, but are not limited to, methylthio, ethylthio, tert-butylthio, and hexylthio.

The term "$(C_1-C_6)$alkylthiocarbonyl" as used herein, means a $(C_1-C_6)$alkylthio group, as defined herein, appended to the parent molecular moiety through a carbonyl group. Representative examples of $(C_1-C_6)$alkylthiocarbonyl include, but are not limited to, methylthiocarbonyl, ethylthiocarbonyl, tert-butylthiocarbonyl, and hexylthiocarbonyl.

The term "$(C_1-C_6)$alkylthio$(C_1-C_6)$alkyl" as used herein, means a $(C_1-C_6)$alkylthio group, as defined herein, appended to the parent molecular moiety through a $(C_1-C_6)$alkyl group, as defined herein. Representative examples of $(C_1-C_6)$alkylthio$(C_1-C_6)$alkyl include, but are not limited to, methylthiomethyl and 2-(ethylthio)ethyl.

The term "$(C_2-C_6)$alkynyl" as used herein, means a straight or branched chain hydrocarbon group containing from 2 to 6 carbon atoms and containing at least one carbon-carbon triple bond. Representative examples of $(C_2-C_6)$alkynyl include, but are not limited to, acetylenyl, 1-propynyl, 2-propynyl, 3-butynyl, 2-pentynyl, and 1-butynyl.

The term "$(C_2-C_6)$alkynylene" means a divalent group derived from a straight or branched chain hydrocarbon of from 2 to 6 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "$(C_6-C_{12})$aryl," as used herein, means phenyl or a bicyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl.

The $(C_6-C_{12})$aryl groups of the invention are optionally substituted with 1, 2, 3, 4, or 5 groups that are independently $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxysulfonyl, $(C_1-C_6)$alkyl, $(C_1-C_6)$alkylcarbonyl, $(C_1-C_6)$alkylcarbonyl$(C_1-C_6)$alkyl, $(C_1-C_6)$alkylcarbonyloxy, $(C_1-C_6)$alkylsulfinyl, $(C_1-C_6)$alkylsulfonyl, $(C_1-C_6)$alkylthio, $(C_1-C_6)$alkylthio$(C_1-C_6)$alkyl, $(C_2-C_6)$alkynyl, carboxy, carboxy$(C_1-C_6)$alkyl, cyano, cyano$(C_1-C_6)$alkyl, ethylenedioxy, formyl, halo$(C_1-C_6)$alkoxy, halo$(C_1-C_6)$alkyl, halogen, hydroxy, hydroxy$(C_1-C_6)$alkyl, mercapto, methylenedioxy, nitro, oxo, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl $(C_1-C_6)$alkyl. Representative examples of substituted aryl include, but are not limited to, benzo[1,3]dioxolyl, 2-bromophenyl, 3-bromophenyl, 4-bromophenyl, 3-chlorophenyl, 4-chlorophenyl, 3-chloro-4-cyanophenyl, 4-chloro-3-fluorophenyl, 4-chloro-2-fluorophenyl, 2-chloro-4-methoxyphenyl, 2-cyanophenyl, 3-cyanophenyl, 4-cyanophenyl, 3-cyano-4-ethoxyphenyl, 3-cyano-4-fluorophenyl, 2,3-dihydrobenzo[b][1,4]dioxinyl, 2,3-dichlorophenyl, 2,6-dichlorophenyl, 2,4-dichlorophenyl, 3,4-dichlorophenyl, 2,3-difluorophenyl, 2,4-difluorophenyl, 2,5-difluorophenyl, 3,4-difluorophenyl, 4-difluoromethoxy-3-methylphenyl, 3-difluoromethoxyphenyl, 2,6-dimethoxyphenyl, 3,4-dimethoxyphenyl, 2,5-dimethylphenyl, 2-ethylphenyl, 2-fluorophenyl, 3-fluorophenyl, 4-fluorophenyl, 2-fluoro-3-methoxyphenyl, 2-fluoro-4-methoxyphenyl, 3-fluoro-4-methoxyphenyl, 4-fluoro-3-methylphenyl, 3-fluoro-2-methylphenyl, 3-hydroxyphenyl, 2-isopropylphenyl, 2-methoxyphenyl, 3-methoxyphenyl, 4-methoxyphenyl, 2-methylphenyl, 3-methylphenyl, 4-methyphenyl, 2-methyl-4-hydroxyphenyl, 3-methyl-4-hydroxyphenyl, 3-methylthiophenyl, 1-oxo-2,3-dihydro-1H-indenyl, 3-oxo-2,3-dihydro-1H-indenyl, 8-oxo-5,6,7,8-tetrahydronaphthalenyl, 2-tert-butylphenyl, 3-tert-butylphenyl, 3-trifluoromethoxyphenyl, 4-trifluoromethylphenyl, and 2,3,4,-trifluorophenyl.

The term "$(C_6-C_{12})$aryl$(C_1-C_6)$alkyl" as used herein, means a $(C_6-C_{12})$aryl group, as defined herein, appended to the parent molecular moiety through an $(C_1-C_6)$alkyl group, as defined herein. Representative examples of $(C_6-C_{12})$aryl$(C_1-C_6)$alkyl include, but are not limited to, benzyl, 2-phenylethyl, 3-phenylpropyl, and 2-naphth-2-ylethyl.

The term "$(C_6-C_{12})$aryl-NR$^5$—" as used herein, means a $(C_6-C_{12})$aryl group, as defined herein, appended to the parent molecular moiety through an —NR$^5$— group.

The term "$(C_6-C_{12})$aryloxy" as used herein, means a $(C_6-C_{12})$aryl group, as defined herein, appended to the parent molecular moiety through an oxygen atom. Representative examples of $(C_6-C_{12})$aryloxy include, but are not limited to, phenoxy and naphthalenyloxy.

The term "$(C_6-C_{12})$arylthio" as used herein, means a $(C_6-C_{12})$aryl group, as defined herein, appended to the parent molecular moiety through a sulfur atom. Representative examples of $(C_6-C_{12})$arylthio include, but are not limited to, phenthio and naphthalenylthio.

The term "carbonyl" as used herein, means a —C(O)— group.

The term "carboxy" as used herein, means a —CO$_2$H group.

The term "carboxy$(C_1-C_6)$alkyl" as used herein, means a carboxy group, as defined herein, is attached to the parent molecular moiety through a $(C_1-C_6)$alkyl group.

The term "cyano" as used herein, means a —CN group.

The term "cyano$(C_1-C_6)$alkyl" as used herein, means a cyano group, as defined herein, appended to the parent molecular moiety through a $(C_1-C_6)$alkyl group, as defined herein. Representative examples of cyanoalkyl include, but are not limited to, cyanomethyl, 2-cyanoethyl, and 3-cyanopropyl.

The term "$(C_5-C_8)$cycloalkenyl" as used herein, means a cyclopentyl, cyclohexyl, cycloheptyl, or cyclooctyl group that contains at least one carbon-carbon double bond. Representative examples of $(C_5-C_8)$cycloalkenyl include, but are not limited to, cyclohexenyl, cyclohexadienyl, cyclopentenyl, cycloheptenyl, and cyclooctenyl.

The term "$(C_3-C_8)$cycloalkyl" as used herein, means a saturated cyclic hydrocarbon group containing from 3 to 8 carbons, examples of $(C_3-C_8)$cycloalkyl include cyclopropyl, cyclobutyl, cyclopentyl, cyclohexyl, cycloheptyl, and cyclooctyl.

The $(C_3-C_8)$cycloalkyl groups of the invention are optionally substituted with 1, 2, 3, or 4 groups that are independently $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxysulfonyl, $(C_1-C_6)$alkyl, $(C_1-C_6)$alkylcarbonyl, $(C_1-C_6)$alkylcarbonyl$(C_1-$ C$_6$)alkyl, (C$_1$-C$_6$)alkylcarbonyloxy, (C$_1$-C$_6$)alkylsulfinyl, (C$_1$-C$_6$)alkylsulfonyl, (C$_1$-C$_6$)alkylthio, (C$_1$-C$_6$)alkylthio(C$_1$-C$_6$)alkyl, (C$_2$-C$_6$)alkynyl, carboxy, carboxy(C$_1$-C$_6$)alkyl, cyano, cyano(C$_1$-C$_6$)alkyl, ethylenedioxy, formyl, halo(C$_1$-C$_6$)alkoxy, halo(C$_1$-C$_6$)alkyl, halogen, hydroxy, hydroxy(C$_1$-C$_6$)alkyl, mercapto, nitro, oxo, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl(C$_1$-C$_6$)alkyl.

The term "(C$_3$-C$_8$)cycloalkyl(C$_1$-C$_6$)alkyl" as used herein, means a (C$_3$-C$_8$)cycloalkyl group, as defined herein, appended to the parent molecular moiety through a (C$_1$-C$_6$)alkyl group, as defined herein. Representative examples of (C$_3$-C$_8$)cycloalkyl(C$_1$-C$_6$)alkyl include, but are not limited to, cyclopropylmethyl, 2-cyclobutylethyl, cyclopentylmethyl, cyclohexylmethyl, and 4-cycloheptylbutyl.

The term "(C$_3$-C$_8$)cycloalkyl-NR$^5$—" as used herein, means a (C$_3$-C$_8$)cycloalkyl group, as defined herein, appended to the parent molecular moiety through a —NR$^5$— group.

The term "(C$_3$-C$_8$)cycloalkyloxy" as used herein, means a (C$_3$-C$_8$)cycloalkyl group, as defined herein, appended to the parent molecular moiety through an oxygen atom. Representative examples of (C$_3$-C$_8$)cycloalkyloxy include, but are not limited to, cyclopropyloxy, 2-cyclobutyloxy, cyclopentyloxy, cyclohexyloxy, and 4-cycloheptyloxy.

The term "(C$_3$-C$_8$)cycloalkylthio" as used herein, means a (C$_3$-C$_8$)cycloalkyl group, as defined herein, appended to the parent molecular moiety through a sulfur atom. Representative examples of (C$_3$-C$_8$)cycloalkylthio include, but are not limited to, cyclopropylthio, cyclobutylthio, cyclopentylthio, cyclohexylthio, and cycloheptylthio.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "halo(C$_1$-C$_3$)alkoxy" as used herein, means at least one halogen, as defined herein, appended to the parent molecular moiety through a (C$_1$-C$_3$)alkoxy group, as defined herein. Representative examples of halo(C$_1$-C$_3$)alkoxy include, but are not limited to, chloromethoxy, 2-fluoroethoxy, trifluoromethoxy, and pentafluoroethoxy.

The term "halo(C$_1$-C$_6$)alkyl" as used herein, means at least one halogen, as defined herein, appended to the parent molecular moiety through a (C$_1$-C$_6$)alkyl group, as defined herein. Representative examples of halo(C$_1$-C$_6$)alkyl include, but are not limited to, chloromethyl, 2-fluoroethyl, trifluoromethyl, pentafluoroethyl, and 2-chloro-3-fluoropentyl.

The term "halo(C$_1$-C$_3$)alkyl" as used herein, means at least one halogen, as defined herein, appended to the parent molecular moiety through a (C$_1$-C$_3$)alkyl group, as defined herein. Representative examples of halo(C$_1$-C$_3$)alkyl include, but are not limited to, chloromethyl, difluoromethyl, 2-fluoroethyl, 2,2-difluoroethyl, trifluoromethyl, pentafluoroethyl, and 2-chloro-3-fluoropentyl.

The term "(C$_5$-C$_{12}$)heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and/or optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The monocyclic heteroaryl and the bicyclic heteroaryl are connected to the parent molecular moiety through any carbon atom or any nitrogen atom contained within the monocyclic heteroaryl or the bicyclic heteroaryl. Representative examples of bicyclic heteroaryl include, but are not limited to, benzimidazolyl, benzofuranyl, benzothienyl, benzoxadiazolyl, benzoxazolyl, benzothiazolyl, cinnolinyl, dihydroquinolinyl, dihydroisoquinolinyl, furopyridinyl, indazolyl, indolyl, isoquinolinyl, naphthyridinyl, phthalazinyl, pyrrolopyridinyl, 1H-pyrrolo[2,3-b]pyridinyl, quinazolinyl, quinolinyl, quinoxalinyl, tetrahydroquinolinyl, and thienopyridinyl.

The (C$_5$-C$_{12}$)heteroaryl groups of the invention are optionally substituted with 1, 2, 3, or 4 groups that are independently (C$_1$-C$_6$)alkoxy, (C$_1$-C$_6$)alkoxy(C$_1$-C$_6$)alkyl, (C$_1$-C$_6$)alkoxycarbonyl, (C$_1$-C$_6$)alkoxycarbonyl(C$_1$-C$_6$)alkyl, (C$_1$-C$_6$)alkoxysulfonyl, (C$_1$-C$_6$)alkyl, (C$_1$-C$_6$)alkylcarbonyl, (C$_1$-C$_6$)alkylcarbonyl(C$_1$-C$_6$)alkyl, (C$_1$-C$_6$)alkylcarbonyloxy, (C$_1$-C$_6$)alkylsulfinyl, (C$_1$-C$_6$)alkylsulfonyl, (C$_1$-C$_6$)alkylthio, (C$_1$-C$_6$)alkylthio(C$_1$-C$_6$)alkyl, (C$_2$-C$_6$)alkynyl, carboxy, carboxy(C$_1$-C$_6$)alkyl, cyano, cyano(C$_1$-C$_6$)alkyl, ethylenedioxy, formyl, halo(C$_1$-C$_6$)alkoxy, halo(C$_1$-C$_6$)alkyl, halogen, hydroxy, hydroxy(C$_1$-C$_6$)alkyl, mercapto, nitro, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl(C$_1$-C$_6$)alkyl. Heteroaryl groups of the invention that are substituted may be as tautomers. The present invention encompasses all tautomers including non-aromatic tautomers.

The term "(C$_5$-C$_{12}$)heteroaryl(C$_1$-C$_6$)alkyl" as used herein, means a (C$_5$-C$_{12}$)heteroaryl, as defined herein, appended to the parent molecular moiety through an (C$_1$-C$_6$)alkyl group, as defined herein. Representative examples of (C$_5$-C$_{12}$)heteroaryl(C$_1$-C$_6$)alkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "(C$_3$-C$_{12}$)heteroaryl-NR$^5$—" as used herein, means a (C$_5$-C$_{12}$)heteroaryl, as defined herein, appended to the parent molecular moiety through a NR$^5$ group.

The term "(C$_5$-C$_{12}$)heteroaryloxy" as used herein, means a (C$_5$-C$_{12}$)heteroaryl group, as defined herein, appended to the parent molecular moiety through an oxygen atom. Representative examples of (C$_5$-C$_{12}$)heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "(C$_5$-C$_{12}$)heteroarylthio" as used herein, means a (C$_5$-C$_{12}$)heteroaryl group, as defined herein, appended to the parent molecular moiety through a sulfur atom. Representative examples of (C$_5$-C$_{12}$)heteroarylthio include, but are not limited to, pyridin-3-ylthio and quinolin-3-ylthio.

The term "(C$_3$-C$_{13}$)heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle consists of a monocyclic heterocycle fused to a phenyl, or a monocyclic heterocycle fused to a cycloalkyl, or a monocyclic heterocycle fused to a cycloalkenyl. The monocyclic heterocycle and bicyclic heterocycle are connected to the parent molecular moiety through any carbon atom or any nitrogen atom contained within the heterocycle. Representative examples of (C$_5$-C$_{13}$)heterocycle include, but are not limited to, azetidinyl, azepanyl, aziridinyl, diazepanyl, 2,3-dihydrobenzofuranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The (C$_3$-C$_{13}$)heterocycle groups of the invention are optionally substituted with 1, 2, 3, 4, or 5 groups that are independently independently (C$_2$-C$_6$)alkenyl, (C$_1$-C$_6$)alkoxy, (C$_1$-C$_6$)alkoxy(C$_1$-C$_6$)alkyl, (C$_1$-C$_6$)alkoxycarbonyl, (C$_1$-C$_6$)alkoxycarbonyl(C$_1$-C$_6$)alkyl, (C$_1$-C$_6$)alkoxysulfonyl, (C$_1$-C$_6$)alkyl, (C$_1$-C$_6$)alkylcarbonyl, (C$_1$-C$_6$)alkylcarbonyl(C$_1$-C$_6$)alkyl, (C$_1$-C$_6$)alkylcarbonyloxy, (C$_1$-C$_6$)alkylsulfinyl, (C$_1$-C$_6$)alkylsulfonyl, (C$_1$-C$_6$)alkylthio, (C$_1$-C$_6$)alkylthio(C$_1$-C$_6$)alkyl, (C$_2$-C$_6$)alkynyl, carboxy, carboxy(C$_1$-C$_6$)alkyl, cyano, cyano(C$_1$-C$_6$)alkyl, ethylenedioxy, formyl, halo(C$_1$-C$_6$)alkoxy, halo(C$_1$-C$_6$)alkyl, halogen, hydroxy, hydroxy(C$_1$-C$_6$)alkyl, mercapto, nitro, oxo, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl(C$_1$-C$_6$)alkyl.

The term "(C$_3$-C$_{13}$)heterocycle(C$_1$-C$_6$)alkyl" as used herein, means a (C$_5$-C$_{13}$)heterocycle, as defined herein, appended to the parent molecular moiety through an (C$_1$-C$_6$) alkyl group, as defined herein.

The term "(C$_3$-C$_{13}$)heterocycle-NR$^5$—" as used herein, means a (C$_5$-C$_{13}$)heterocycle, as defined herein, appended to the parent molecular moiety through a NR$^5$ group.

The term "(C$_3$-C$_{13}$)heterocycleoxy" as used herein, means a (C$_5$-C$_{13}$)heterocycle, as defined herein, appended to the parent molecular moiety through an oxygen atom.

The term "(C$_3$-C$_{13}$)heterocyclethio" as used herein, means a (C$_5$-C$_{13}$)heterocycle, as defined herein, appended to the parent molecular moiety through a sulfur atom. Representative examples of heteroarylthio include, but are not limited to, pyridin-3-ylthio and quinolin-3-ylthio.

The term "hydroxy" as used herein, means an —OH group.

The term "hydroxy(C$_1$-C$_{10}$)alkyl" as used herein, means at least one hydroxy group, as defined herein, is appended to the parent molecular moiety through a (C$_1$-C$_{10}$)alkyl group, as defined herein. Representative examples of hydroxy(C$_1$-C$_{10}$) alkyl include, but are not limited to, hydroxymethyl, 2-hydroxyethyl, 3-hydroxypropyl, 2,3-dihydroxypentyl, 2-ethyl-4-hydroxyheptyl, 5,6-dihydroxyoctyl, and 9-hydroxynonyl.

The term "hydroxy(C$_1$-C$_6$)alkylthio" as used herein, means a hydroxy(C$_1$-C$_6$)alkyl group, as defined herein, is appended to the parent molecular moiety through a sulfur atom.

The term "mercapto" as used herein, means a —SH group.

The term "mercapto(C$_1$-C$_{10}$)alkyl" as used herein, means at least one mercapto group, as defined herein, is appended to the parent molecular moiety through a (C$_1$-C$_{10}$)alkyl group, as defined herein.

The term "methylenedioxy" as used herein, means a —O(CH$_2$)O— group wherein the oxygen atoms of the methylenedioxy group are attached to the parent molecular moiety through two adjacent carbon atoms forming a five membered ring.

The term "nitro" as used herein, means a —NO$_2$ group.

The term "NZ$^1$Z$^2$" as used herein, means two groups, Z$^1$ and Z$^2$, which are appended to the parent molecular moiety through a nitrogen atom. Z$^1$ and Z$^2$ are each independently hydrogen, (C$_1$-C$_6$)alkyl, (C$_1$-C$_6$)alkylcarbonyl, or formyl. Representative examples of NZ$^1$Z$^2$ include, but are not limited to, amino, methylamino, acetylamino, acetylmethylamino, butylamino, diethylamino, dimethylamino, ethylmethylamino, and formylamino.

The term "(NZ$^1$Z$^2$)carbonyl" as used herein, means a NZ$^1$Z$^2$ group, as defined herein, appended to the parent molecular moiety through a carbonyl group, as defined herein. Representative examples of (NZ$^1$Z$^2$)carbonyl include, but are not limited to, aminocarbonyl, (methylamino)carbonyl, (dimethylamino)carbonyl, and (ethylmethylamino)carbonyl.

The term "NZ$^1$Z$^2$(C$_1$-C$_6$)alkyl" as used herein, means a NZ$^1$Z$^2$ group, as defined herein, appended to the parent molecular moiety through a (C$_1$-C$_6$)alkyl group, as defined herein.

The term "(NZ$^1$Z$^2$)carbonyloxy" as used herein, means a (NZ$^1$Z$^2$)carbonyl group, as defined herein, appended to the parent molecular moiety through an oxygen atom.

The term "(NZ$^1$Z$^2$)sulfonyl" as used herein, means a NZ$^1$Z$^2$ group, as defined herein, appended to the parent molecular moiety through a sulfonyl group, as defined herein. Representative examples of (NZ$^1$Z$^2$)sulfonyl include, but are not limited to, aminosulfonyl, (methylamino)sulfonyl, (dimethylamino)sulfonyl, and (ethylmethylamino)sulfonyl.

The term "(NZ$^1$Z$^2$)carbonyl(C$_1$-C$_6$)alkyl" as used herein, means a (NZ$^1$Z$^2$)carbonyl group, as defined herein, appended to the parent molecular moiety through a (C$_1$-C$_6$)alkyl group, as defined herein.

The term "(NZ$^1$Z$^2$)thiocarbonyloxy" as used herein, means a (NZ$^1$Z$^2$)thiocarbonyl group, as defined herein, appended to the parent molecular moiety through an oxygen atom.

The term "oxo" as used herein, means a =O moiety.

The term "sulfinyl" as used herein, means a —S(O)— group.

The term "sulfonyl" as used herein, means a —SO$_2$— group.

The phrase "therapeutically effective amount" means an amount of a compound of Formula I that, when administered to a patient, provides the desired effect, i.e., lessening in the severity of the symptoms associated with a bacterial infection, decreasing the number of bacteria in the affected tissue, and/or preventing bacteria in the affected tissue from increasing in number (localized or systemic).

The term "patient" means a warm blooded animals such as for example, livestock, guinea pigs, mice, rats, gerbils, cats, rabbits, dogs, monkeys, chimpanzees, and humans.

The term "treat" means the ability of the compounds to relieve, alleviate or slow the progression of the patient's bacterial infection (or condition) or any tissue damage associated with the disease.

The phrase "pharmaceutically acceptable" indicates that the substance or composition must be compatible chemically and/or toxicologically, with the other ingredients comprising a formulation, and/or the mammal being treated therewith.

The term "isomer" means "stereoisomer" and "geometric isomer" as defined below.

The term "stereoisomer" means compounds that possess one or more chiral centers and each center may exist in the (R) or (S) configuration. Stereoisomers include all diastereomeric, enantiomeric and epimeric forms as well as racemates and mixtures thereof.

The term "geometric isomer" means compounds that may exist in cis, trans, anti, entgegen (E), and zusammen (Z) forms as well as mixtures thereof.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare these pharmaceutically acceptable base salts are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

Certain of the compounds of the Formula I may exist as geometric isomers. The compounds of the Formula I may possess one or more asymmetric centers, thus existing as two or more stereoisomeric forms. The present invention includes all the individual stereoisomers and geometric isomers of the compounds of Formula I and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

Medical and Veterinary Uses

The compounds may be used for the treatment or prevention of infectious disorders, especially those caused by susceptible and multi-drug resistant (MDR) Gram-negative bacteria. Examples of such Gram-negative bacteria include *Acinetobacter baumannii, Acinetobacter* spp., *Achromobacter* spp., *Aeromonas* spp., *Bacteroides fragilis, Bordetella* spp., *Borrelia* spp., *Brucella* spp., *Campylobacter* spp., *Citrobacter diversus* (koseri), *Citrobacter freundii, Enterobacter aerogenes, Enterobacter cloacae, Escherichia coli, Francisella tularensis, Fusobacterium* spp., *Haemophilus influenzae* (β-lactamase positive and negative), *Helicobacter pylori, Klebsiella oxytoca, Klebsiella pneumoniae* (including those encoding extended-spectrum β-lactamases (hereinafter "ESBLs"), *Legionella pneumophila, Moraxella catarrhalis* (β-lactamase positive and negative), *Morganella morganii, Neisseria gonorrhoeae, Neisseria meningitidis, Proteus vulgaris, Porphyromonas* spp., *Prevotella* spp., *Mannheimia haemolyticus, Pasteurella* spp., *Proteus mirabilis, Providencia* spp., *Pseudomonas aeruginosa, Pseudomonas* spp., *Salmonella* spp., *Shigella* spp., *Serratia marcescens, Treponema* spp., *Burkholderia cepacia, Vibrio* spp., *Yersinia* spp., and *Stenotrophomonas maltophilia*. Examples of other Gram-negative organisms include members of the Enterobacteriaceae that express ESBLs; KPCs, CTX-M, metallo-β-lactamases (such as NDM-1, for example), and AmpC-type beta-lactamases that confer resistance to currently available cephalosporins, cephamycins, carbapenems, beta-lactams, and beta-lactam/beta-lactamase inhibitor combinations.

In a more specific embodiment, the Gram-negative bacteria are selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia, Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, beta-lactams, and beta-lactams/beta-lactamase inhibitor combinations.

Examples of infections that may be treated with the compounds of Formula I include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: www.informahealthcare.com, Expert Opin. Drug Saf. (2008) 7(3).

In order to exhibit this antibacterial activity, the compounds of Formula I need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessibly by local application, such as, for example, eyes, ears including external and middle ear infections, vaginal, open wound, skin including the surface skin and the underneath dermal structures, or lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 100% by weight, of the active material, depending on the method of administration. Where the compositions comprise dosage units, each unit will contain, for example, from about 0.5-1000 mg of the active ingredient. The dosage as employed for adult human treatment will range, for example, from about 10 to 3000 mg per day, depending on the route and frequency of administration.

If desired, the compounds of the invention may be administered in combination with one or more additional anti-bacterial agents ("the additional active agent"). Such use of compounds of the invention in combination with an additional active agent may be for simultaneous, separate or sequential use.

The Examples and preparations provided below further illustrate and exemplify the compounds of the present invention and methods of preparing such compounds. It is to be understood that the scope of the present invention is not limited in any way by the scope of the following Examples and preparations. In the following Examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Synthetic Methodology

Compounds of Formula I can be prepared by a variety of methods. Reaction schemes below are representative methods for preparing compounds of Formula I. Modifications of these methods should be readily apparent to those skilled in the art.

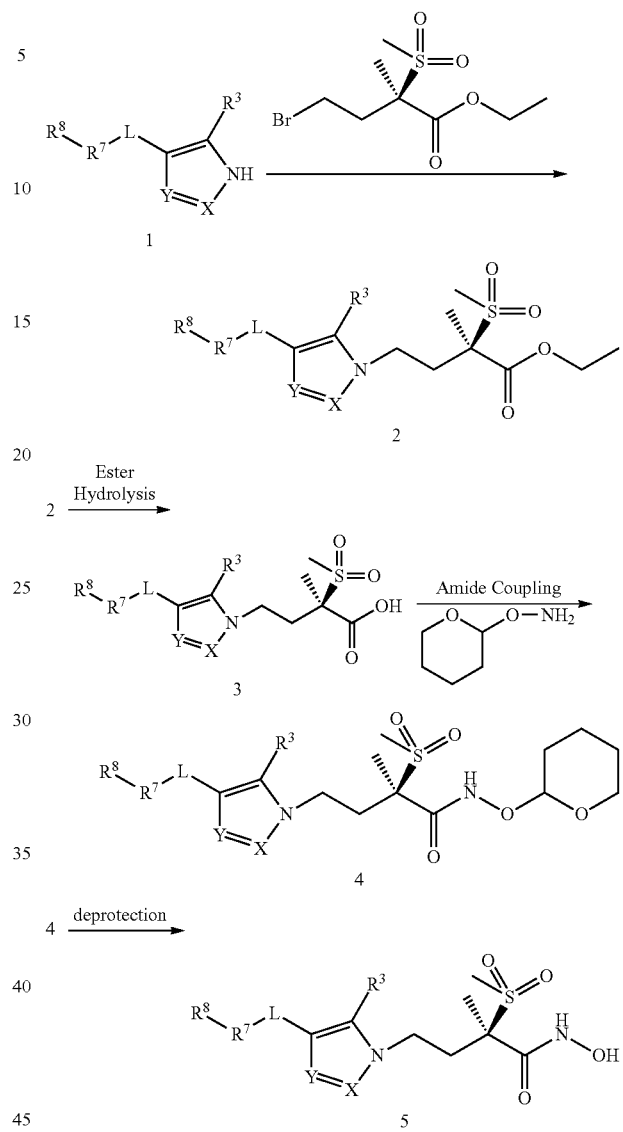

Scheme A

Scheme A depicts one method for preparation of compounds of Formula I where $R^3$, $R^7$, $R^8$, X, Y, and L are as defined in Formula I of the Summary section herein. A compound such as pyrazole 1 is N-alkylated with Ethyl (2R)-4-bromo-2-methyl-2-(methylsulfonyl)butanoate, using mild bases such as $Cs_2CO_3$, $K_2CO_3$ and others which are obvious to those skilled in the art, to generate structure 2. The pyrazole derivatives 1 are known in the art or are prepared using synthetic methods known in the art. In pyrazole 1, $R^3$, $R^7$, $R^8$ and L represent the same moiety as is desired in the final product. Structure 2 is converted to carboxylic acid 3 by basic hydrolysis using reagents such as NaOH, LiOH, and KOH. Structure 3 is treated with O-(tetrahydro-2-H-pyran-2-yl)hydroxylamine using standard amide coupling conditions, for example, employing coupling reagents such as HATU, CDMT, EDCI to provide protected hydroxamic acid 4. Finally, the tetrahydropyran protecting group in structure 4 is removed using acid such as HCl or PPTS in a protic solvent such as water or ethanol, to provide compounds of Formula I.

Scheme B

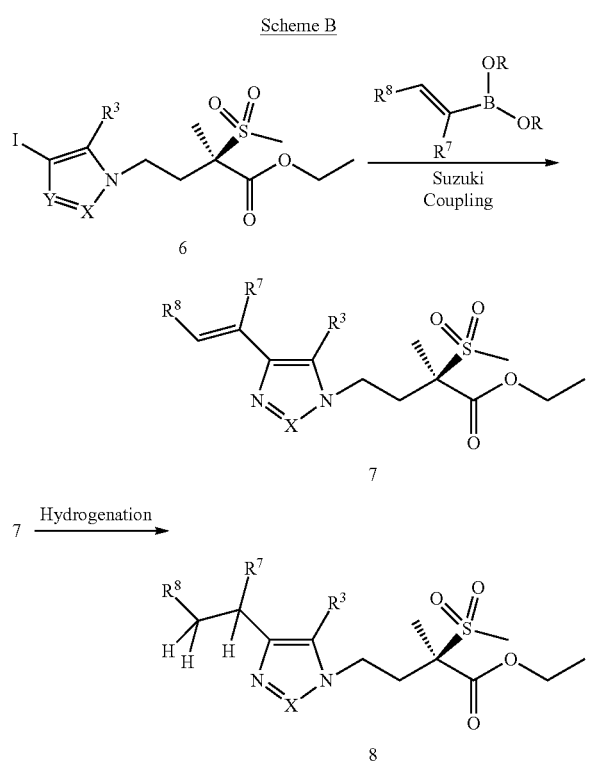

Scheme B depicts an alternative approach to preparing compounds of Formula I where $R^3$, $R^7$, $R^8$, X, Y, and L are as defined in Formula I of the Summary section herein. Iodopyrazole 6 and the appropriate boronic acid/ester are subjected to a Suzuki coupling reaction to give ester 7. Ester 7 is converted to the final hydroxamic acid 5 as described in scheme A. Alternatively, structure 7 can be treated under hydrogenation conditions using a catalyst such as Palladium on carbon to give structure 8 which is converted to compounds of Formula I as described in scheme A.

Scheme C

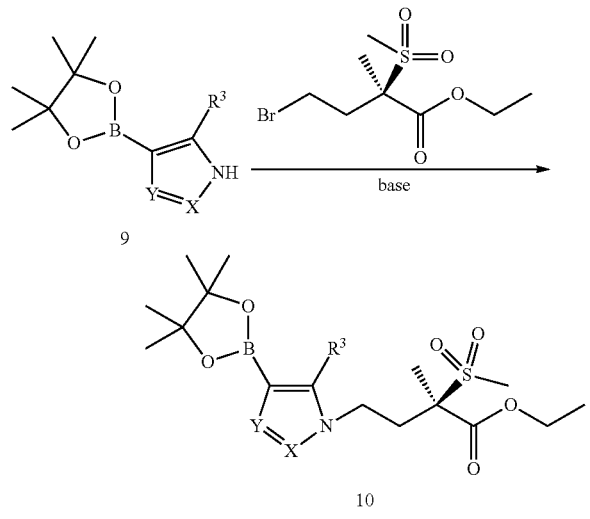

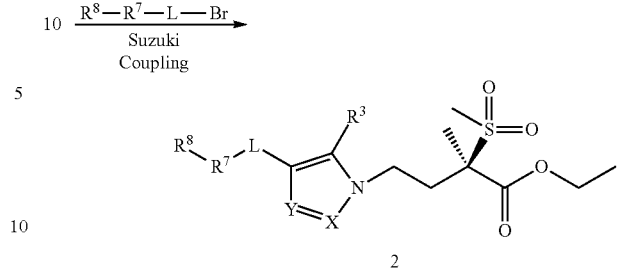

An additional route to access ester compounds 2 is illustrated in scheme C where $R^3$, $R^7$, $R^8$, X, Y, and L are as defined in Formula I of the Summary section herein. Boronic ester 9 can be N-alkylated using mild base to give boronate 10. The reaction of 10 with the appropriate aryl bromide or heteroaryl bromide under standard Suzuki coupling conditions (for example, $Pd(PPh_3)_4$ catalyst, base such as $K_2CO_3$ in DMF/water or dioxane/water at 80° C.) yields structure 2 which is treated as described in Scheme A to provide compounds of Formula I.

Scheme D

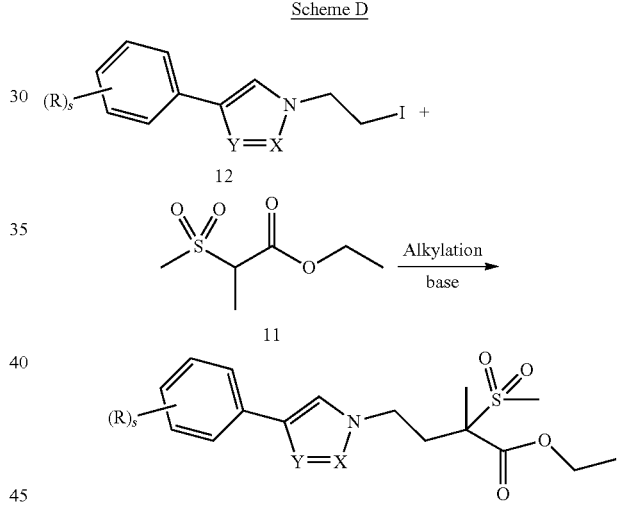

Ester 2 may also be prepared according to the route illustrated in scheme D where $R^3$, $R^7$, $R^8$, X, Y, and L are as defined in Formula I of the Summary section herein and R is an aryl substituent as defined in the definition section herein and "s" is an integer 0-5. A compound 12 is treated with the enolate of structure 11 to provide an ester of structure 2 which is then converted to a compound of Formula I using the methodology described in Scheme A.

Scheme E

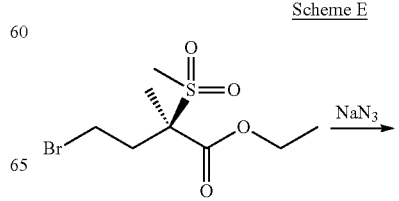

-continued

13

14

Amide Coupling

15

"Click Reaction"

4 deprotection

5

Compounds of formula I are prepared via the synthetic route depicted in scheme E or a variation thereof where $R^3$, $R^7$, $R^8$, X, Y, and L are as defined in Formula I of the Summary section herein. Modification of the order of the synthetic steps in scheme E should be readily apparent to those skilled in the art. Treatment of ethyl (2R)-4-bromo-2-methyl-2-(methylsulfonyl)butanoate with sodium azide provides compound 13 which is saponified to acid 14 and then coupled to the protected hydroxamic acid using procedures and/or conditions as described herein to provide azide 15. Azide 15 is treated under the Azide alkyne Huisgen cycloaddition aka "click reaction" conditions with the appropriate alkyne to give compound 4. Typical conditions for the "click reaction" involve treatment of the azide and alkyne with a source of Cu (II), such as CuSO$_4$, and sodium ascorbate in solvent such as EtOH and water. Alternative conditions should be obvious to those skilled in the art. The tetrahydropyran protecting group in structure 4 is removed using acid such as HCl or PPTS in a protic solvent such as water or ethanol to give compounds of Formula I.

LIST OF ABBREVIATIONS

Aq.=aqueous
CDMT=2-chloro-4,6-dimethoxy-1,3,5-triazine
DCM=dichloromethane
DIPEA=diisopropylethylamine
DMF=dimethylformamide
DMSO=dimethyl sulfoxide
d=doublet
dd=doublet of doublets
dq=doublet of quartets
dt=doublet of triplets
EDCI=1-ethyl-3-(3-dimethylaminopropyl)carbodiimide.HCl
eq.=equivalents
Et$_2$O=diethyl ether
EtOAc=ethyl acetate
EtOH=ethanol
g=grams
h=hours
HCl=hydrochloric acid
HOBT=1-hydroxybenzotriazole
HPLC=high pressure liquid chromatography
Hpt=heptane
Hz=hertz
J=coupling constant
M=molar
m=multiplet
m/z=mass to charge ratio
MeCN=acetonitrile
MeOH=methanol
2-MeTHF=2-methyltetrahydrofuran
mg=milligram
MHz=megahertz
min=minutes
mL=milliliter
mm=millimeter
mmol=millimole
MS=mass spectrometry
NMR=nuclear magnetic resonance
PPTS=pyridinium p-toluene sulfonate
q=quartet
RT=room temperature
s=singlet
t=triplet
TEA=triethylamine
TFA=trifluoroacetic acid
THF=tetrahydrofuran Preparation of Intermediates Preparation 1

Ethyl 2-(methylsulfonyl)propanoate

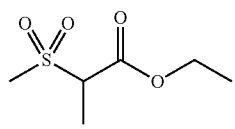

Sodium methyl sulfinate (103 g, 937 mmol) was combined with the ethyl 2-chloropropionate (109 g, 892 mmol) in EtOH (350 mL) in a 500 mL one neck round bottom flask. The reaction was warmed to 77° C. for 20 hours, and then allowed to cool to room temperature. Solids were removed by filtration through celite, and the filter pad was washed with EtOH. The combined filtrates were concentrated in vacuo. The crude product was suspended in diethyl ether (250 mL), and solids were removed by filtration. The filtrate was concentrated in vacuo to afford the title compound as a pale yellow oil (51 g, 73%). $^1$H NMR (400 MHz, CHLOROFORM-d) δ 1.32 (t, J=7.05 Hz, 3H) 1.67 (d, J=7.47 Hz, 3H) 3.05 (s, 3H) 3.83-3.92 (m, 1H) 4.18-4.37 (m, 2H).

Preparation 2

(+/−)-Ethyl 4-bromo-2-methyl-2-(methylsulfonyl)butanoate

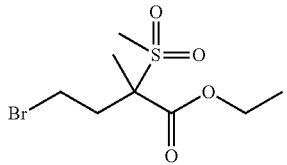

Sodium hydride (60% dispersion in mineral oil, 2.33 g, 58.3 mmol) was washed with hexane (2×10 mL) in a 100 mL two neck round bottom flask under nitrogen and then suspended in DMF (30 mL). The suspension was treated dropwise with ethyl 2-(methylsulfonyl)propanoate (10.0 g, 55.49 mmol) in DMF (10 mL). The mixture was stirred for 30 min at RT, cooled to 0° C., and treated dropwise with 1,2-dibromoethane (5.17 mL, 58.8 mmol). The mixture was allowed to warm to room temperature while stirring overnight. The mixture was quenched with saturated ammonium chloride (100 mL) and then extracted with diethyl ether (4×50 mL). The combined organic layers were washed with 50% saturated sodium chloride (4×50 mL), dried (MgSO$_4$), filtered and the filtrate concentrated in vacuo. The crude material was chromatographed over silica gel (350 g, 230-400 mesh) eluting with 10-20% EtOAc/hexane to afford the title compound as a pale yellow oil (7.9 g, 50%). $^1$H NMR (400 MHz, CHLOROFORM-d) δ 1.33 (t, J=7.05 Hz, 3H) 1.64 (s, 3H) 2.49-2.59 (m, 1H) 2.78 (ddd, J=13.89, 10.16, 6.64 Hz, 1H) 3.05 (s, 3H) 3.33-3.41 (m, 1H) 3.46-3.54 (m, 1H) 4.22-4.37 (m, 2H).

Preparation 3

Ethyl (2R)-4-bromo-2-methyl-2-(methylsulfonyl)butanoate

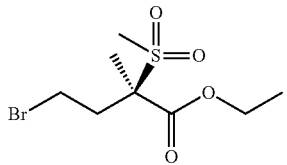

Chiral separation of (+/−)-Ethyl 4-bromo-2-methyl-2-(methylsulfonyl)butanoate

Crude (+/−)-ethyl 4-bromo-2-methyl-2-(methylsulfonyl) butanoate (1.82 kg) was purified via flash chromatography using an LP-600 column and toluene as the eluant to afford pure (+/−)-ethyl 4-bromo-2-methyl-2-(methylsulfonyl)butanoate (1.63 kg). The purified material was dissolved in EtOH (75 g/L) and resolved via chiral multi-column chromatography (condition listed in Table 1) on MCC-2 to afford enantiomer #1 (738.4 g, =4.719 min, $[α]_{589}^{20}$=+14.1°) at 99% enantiomeric purity and enantiomer #2 (763.8 g, =4.040 min) at 95% enantiomeric purity. Purity of the enantiomers was determined via chiral HPLC, 4.6×250 mm Chiralpak AD, 10μ column, 215 nm wavelength, mobile phase: EtOH, isocratic elution at 1 mL/min at ambient temperature. Enantiomer #1 was determined to be Ethyl (2R)-4-bromo-2-methyl-2-(methylsulfonyl)butanoate.

TABLE 1

| Stationary Phase | ChiralPak AD, 20μ |
|---|---|
| Column Dimension/Temp | 5 × 10 cm/30° C. |
| Mobile Phase | 100% EtOH |
| Feed Concentration | 75 g/L in mobile phase |
| Feed Rate | 4.0 mL/min |
| Eluant Rate | 90.5 mL/min |
| Raffinate Rate | 35.6 mL/min |
| Extract Rate | 58.9 mL/min |
| Recycling Rate | 262 mL/min |
| Period Time | 1.0 min |

Preparation 4

Ethyl (2R)-2-methyl-2-(methylsulfonyl)-4-[4-(4,4,5,5-tetramethyl-1,3,2-dioxaborolan-2-yl)-1H-pyrazol-1-yl]butanoate

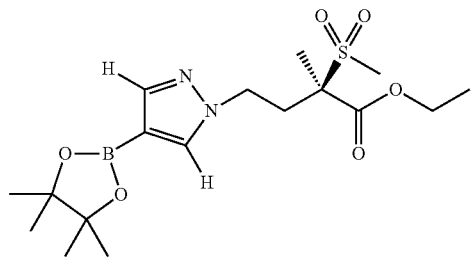 [SMILES: CCOC(=O)[C@@](C)(CCn1cc(B2OC(C)(C)C(C)(C)O2)cn1)S(C)(=O)=O]

4-Pyrazole boronic acid, 4,4,4',4',5,5,5',5'-octamethyl-2,2'-bi(1,3,2-dioxaborolane) (800 mg, 4.12 mmol, 1 eq), Cs$_2$CO$_3$ (3.36 g, 10.3 mmol, 2.5 eq) and NaI (124 mg, 0.825 mmol, 0.2 eq) were added to a vial. A solution of ethyl (2R)-4-bromo-2-methyl-2-(methylsulfonyl)butanoate (1.54 g, 5.36 mmol, 1.3 eq) in MeCN (10 mL) was added to the vial and the sealed mixture was heated at 50° C. overnight. The reaction mixture was cooled to room temperature and filtered through celite, washing with EtOAc. The crude product mixture was purified by flash chromatography on silica gel (40 g) eluting with 0-100% EtOAc/Hpt to give the desired product ethyl (2R)-2-methyl-2-(methylsulfonyl)-4-[4-(4,4,5,5-tetramethyl-1,3,2-dioxaborolan-2-yl)-1H-pyrazol-1-yl]butanoate (810 mg, 49% yield). $^1$H NMR (400 MHz, CHLOROFORM-d) δ 7.78-7.75 (m, 1H), 7.71-7.67 (m, 1H), 4.40-

4.05 (m, 4H), 3.05 (s, 3H), 2.85-2.74 (m, 1H), 2.57-2.46 (m, 1H), 1.68 (s, 3H), 1.36-1.17 (m, 15H). LC-MS M+H+401.3.

Preparation 5

2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide

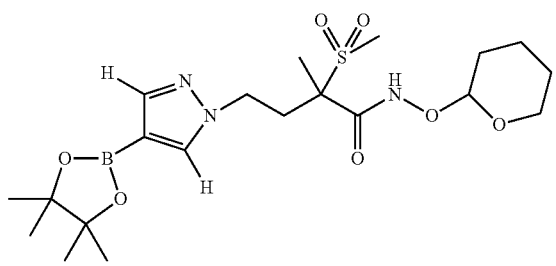 [SMILES: CC1(C)OB(c2cnn(CCC(C)(C(=O)NOC3CCCCO3)S(C)(=O)=O)c2)OC1(C)C]

Step A: 2-methyl-2-(methylsulfonyl)-4-[4-(4,4,5,5-tetramethyl-1,3,2-dioxaborolan-2-yl)-1H-pyrazol-1-yl]butanoic acid To a solution of ethyl 2-methyl-2-(methylsulfonyl)-4-[4-(4,4,5,5-tetramethyl-1,3,2-dioxaborolan-2-yl)-1H-pyrazol-1-yl]butanoate (28 g, 0.07 mol) in THF (100 mL) was added a solution of LiOH (4.2 g, 0.017 mol) in H$_2$O (50 mL). The mixture was stirred at room temperature for 5 h. The THF was removed under reduced pressure and the aqueous phase was washed with EtOAc (50 mL×2) and then acidified with aqueous HCl (3 M). The solid precipitate was filtered to give the first batch of (2-methyl-2-(methylsulfonyl)-4-[4-(4,4,5,5-tetramethyl-1,3,2-dioxaborolan-2-yl)-1H-pyrazol-1-yl]butanoic acid. The mother liquid was refrigerated for 20 h, filtered to give the second batch of 2-methyl-2-(methylsulfonyl)-4-[4-(4,4,5,5-tetramethyl-1,3,2-dioxaborolan-2-yl)-1H-pyrazol-1-yl]butanoic acid. The two batches were combined the and dried to give 2-methyl-2-(methylsulfonyl)-4-[4-(4,4,5,5-tetramethyl-1,3,2-dioxaborolan-2-yl)-1H-pyrazol-1-yl] butanoic acid (13 g, 50%) as a white solid.

Step B: 2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide To a solution of (2-methyl-2-(methylsulfonyl)-4-[4-(4,4,5,5-tetramethyl-1,3,2-dioxaborolan-2-yl)-1H-pyrazol-1-yl]butanoic acid (7.0 g, 0.019 mol) in DMSO (300 mL) was added HOBT (3.24 g, 0.024 mol). The reaction solution was stirred at room temperature for 20 min, EDCI.HCl (4.6 g, 0.024 mol) and O-tetrahydro-2H-pyran-2-yl-hydroxylamine (2.5 g, 0.021 mol) were added at room temperature and the reaction mixture was stirred at room temperature overnight. Water (200 mL) and EtOAc (200 mL) were added and the layers were separated. The aqueous layer was extracted with EtOAc (100 mL×3). The organic layers were combined and washed with H$_2$O (50 mL), brine (20 mL), dried over anhydrous Na$_2$SO$_4$, and concentrated. The residue was purified by flash chromatography on silica gel eluting with MeOH/DCM (0-10% gradient) to give a 2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide (4.7 g, 52%). LC-MS M+H+472.2.

Preparation 6

Ethyl (2R)-4-(4-iodo-1H-pyrazol-1-yl)-2-methyl-2-(methylsulfonyl)butanoate

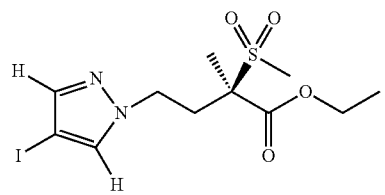 [SMILES: CCOC(=O)[C@@](C)(CCn1cc(I)cn1)S(C)(=O)=O]

To a solution 4-iodoopyrazole (1.7 g, 8.8 mmol) in THF (80 mL) was added ethyl (2R)-4-bromo-2-methyl-2-(methylsulfonyl)butanoate (3.05 g, 10.5 mmol) that had been dissolved in THF (20 mL). To this solution was added cesium carbonate (6.1 g, 18.4 mmol) and the reaction mixture was stirred at 50° C. for 16 hours. Water (50 mL) was added to the reaction and the crude product was extracted with ethyl acetate (3×100 mL). The organic phases were combined, dried over sodium sulfate, filtered and concentrated. The crude product was purified on a silicycle silica gel column (40 g) eluting with 30% ethyl acetate/heptane to 100% ethyl acetate to give the desired product ethyl (2R)-4-(4-iodo-1H-pyrazol-1-yl)-2-methyl-2-(methylsulfonyl)butanoate (3.3 g, 94% yield).
$^1$H NMR (400 MHz, CHLOROFORM-d) δ 7.46 (d, J=0.6 Hz, 1H), 7.40 (d, J=0.6 Hz, 1H), 4.16 (dd, J=0.7, 7.2 Hz, 4H), 3.01 (s, 3H), 2.77-2.67 (m, 1H), 2.51-2.42 (m, 1H), 1.64 (s, 3H), 1.27 (t, J=7.2 Hz, 3H). LC-MS M+H+409.0

Preparation 7

(2R)-4-azido-2-methyl-2-(methylsulfonyl)-N-(tetrahydro-2H-pyran-2-yloxy)butanamide

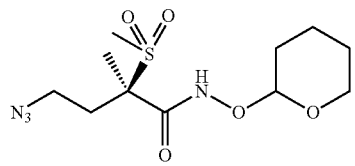 [SMILES: C[C@@](CCN=[N+]=[N-])(C(=O)NOC1CCCCO1)S(C)(=O)=O]

Step A: ethyl (2R)-4-azido-2-methyl-2-(methylsulfonyl)butanoate

To a solution of ethyl (2R)-4-bromo-2-methyl-2-(methylsulfonyl)butanoate (4.5 g, 15.7 mmol, 1 eq) in DMSO (5 mL) was added sodium azide (1.02 g, 15.7 mmol, 1 eq). The mixture was heated at 80° C. for 3 h. The mixture was then diluted with EtOAc and washed with water. The organic layer was dried (MgSO$_4$), filtered and concentrated to give ethyl (2R)-4-azido-2-methyl-2-(methylsulfonyl)butanoate which was used without further purification.

Step B: (2R)-4-azido-2-methyl-2-(methylsulfonyl)butanoic acid

To a solution of ethyl (2R)-4-azido-2-methyl-2-(methylsulfonyl)butanoate (3.9 g, 15.6 mmol, 1 eq) in water (7.5 mL) was added LiOH (16 mmol). The mixture was allowed to stir at 80° C. for 16 h. The crude product was then purified by reverse phase chromatography on a 100 g C18 column eluting with a 0-20% MeOH/water gradient (containing 0.5% TFA) to give the desired product (2R)-4-azido-2-methyl-2-(methylsulfonyl)butanoic acid (1.2 g, 35% yield). LC-MS: M+H+ 222.1.

Step C: (2R)-4-azido-2-methyl-2-(methylsulfonyl)-N-(tetrahydro-2H-pyran-2-yloxy)butanamide To a solution of the (2R)-4-azido-2-methyl-2-(methylsulfonyl)butanoic acid (1.05 g, 4.73 mmol, 1 eq) in THF (15 mL) was added CDMT (830 mg, 4.7 mmol, 1 eq) and N-methylmorpholine (1.46 g, 14.2 mmol, 3 eq). The resulting mixture was stirred at RT for 3 h. O-(tetrahydro-2-H-pyran-2-yl)hydroxylamine (554 mg, 4.72 mmol, 1 eq) was added and the reaction was allowed to stir for 16 h. The white solid precipitate was then filtered off. The filtrate was concentrated in vacuo. The crude product mixture was purified by a silica gel column eluting with 0-20% MeOH/DCM to give the desired product (2R)-4-azido-2-methyl-2-(methylsulfonyl)-N-(tetrahydro-2H-pyran-2-yloxy)butanamide (1 g, 66% yield). $^1$H NMR (400 MHz, METHANOL-d$_4$) δ 5.03-4.92 (m, 1H), 4.21-4.03 (m, 1H), 3.60-3.44 (m, 2H), 3.41-3.32 (m, 1H), 3.03 (m, 3H), 2.68-2.57 (m, 1H), 2.10-2.00 (m, 1H), 1.89-1.61 (m, 4H), 1.59 (d, J=3.7 Hz, 5H). LC-MS M+H+321.3

Example 1

(2R)-4-[4-(cyclohex-1-en-1-yl)-1H-pyrazol-1-yl]-N-hydroxy-2-methyl-2-(methylsulfonyl)butanamide

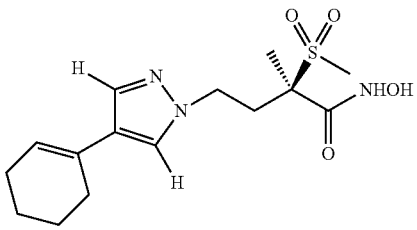

Step A: ethyl (2R)-4-[4-(cyclohex-1-en-1-yl)-1H-pyrazol-1-yl]-2-methyl-2-dimethylsulfonyl)butanoate To a vial containing ethyl (2R)-4-(4-iodo-1H-pyrazol-1-yl)-2-methyl-2-(methylsulfonyl)butanoate (500 mg, 1.25 mmol, 1.0 eq), cyclohex-1-en-1-ylboronic acid (205 mg, 1.62 mmol, 1.3 eq), cesium fluoride (759 mg, 5.00 mmol, 4 eq) and Pd(PPh$_3$)$_4$ (100 mg 0.087 mmol, 0.07 eq) was added THF (5 mL). The vial was sealed and the mixture was heated at 60° C. overnight. The mixture was filtered through celite, and eluted with EtOAc. The filtrate was absorbed onto silica gel and purified by flash chromatography, eluting with 0-20% EtOAc/Hpt then 5% MeOH/EtOAc to give ethyl (2R)-4-[4-(cyclohex-1-en-1-yl)-1H-pyrazol-1-yl]-2-methyl-2-(methylsulfonyl)butanoate (370 mg, 83.6% yield). LC-MS M+H+ 355.1.

Step B: (2R)-4-[4-(cyclohex-1-en-1-yl)-1H-pyrazol-1-yl]-2-methyl-2-(methylsulfonyl)butanoic acid To a solution of ethyl (2R)-4-[4-(cyclohex-1-en-1-yl)-1H-pyrazol-1-yl]-2-methyl-2-(methylsulfonyl)butanoate (370 mg, 1.04 mmol, 1.0 eq) in MeOH/THF (3 mL:3 mL) was added LiOH (52.5 mg, 2.19 mmol, 2.1 eq) in H$_2$O (1.5 mL) and the mixture allowed to stir at RT overnight. The mixture was diluted with 5 mL of H$_2$O and washed with Et$_2$O. The aqueous layer was then acidified with 1 M HCl which precipitated out a white solid. The solid was filtered off and washed with heptane to give (2R)-4-[4-(cyclohex-1-en-1-yl)-1H-pyrazol-1-yl]-2-methyl-2-(methylsulfonyl)butanoic acid (339 mg, 99.5% yield). $^1$H NMR (400 MHz, CHLOROFORM-d) δ 7.75-7.66 (m, 1H), 7.41-7.35 (m, 1H), 6.05-5.96 (m, 1H), 4.78-4.59 (m, 1H), 4.55-4.38 (m, 1H), 3.14 (s, 3H), 2.77-2.64 (m, 1H), 2.51-2.37 (m, 1H), 2.28-2.19 (m, 2H), 2.18-2.06 (m, 2H), 1.80-1.69 (m, 2H), 1.64 (s, 5H). LC-MS M+H+327.1.

Step C: (2R)-4-[4-(cyclohex-1-en-1-yl)-1H-pyrazol-1-yl]-2-methyl-2-(methylsulfonyl)-N-(tetrahydro-2H-pyran-2-yloxy)butanamide To a solution of (2R)-4-[4-(cyclohex-1-en-1-yl)-1H-pyrazol-1-yl]-2-methyl-2-(methylsulfonyl)butanoic acid (339 mg, 1.04 mmol, 1.0 eq) in dichloromethane (10 mL) under nitrogen, was added DIPEA (285 mg, 2.20 mmol, 0.384 mL, 2.12 eq) followed by the addition of 1-hydroxybenzotriazole monohydrate (307 mg, 2.00 mmol, 1.93 eq). The solution was allowed to stir for 30 minutes before being treated with O-tetrahydro-2H-pyran-2-yl-hydroxylamine (163 mg, 1.39 mmol, 1.34 eq) and then dimethylaminopropyl-3-ethylcarbodiimide hydrochloride (285 mg 1.49 mmol, 1.43 eq). The mixture was then allowed to stir for 3 hours at RT. The mixture was then absorbed onto silica gel and purified by flash chromatography eluting with 5-100% EtOAc/Hpt to give (2R)-4-[4-(cyclohex-1-en-1-yl)-1H-pyrazol-1-yl]-2-methyl-2-(methylsulfonyl)-N-(tetrahydro-2H-pyran-2-yloxy)butanamide (230 mg, 52% yield). LC-MS M+H+426.1.

Step D: (2R)-4-[4-(cyclohex-1-en-1-yl)-1H-pyrazol-1-yl]-N-hydroxy-2-methyl-2-(methylsulfonyl)butanamide To a solution of 2R)-4-[4-(cyclohex-1-en-1-yl)-1H-pyrazol-1-yl]-2-methyl-2-(methylsulfonyl)-N-(tetrahydro-2H-pyran-2-yloxy)butanamide (195 mg, 0.458 mmol, 1.0 eq) in EtOH (5 mL) was added PPTS (34.4 mg, 0.137 mmol, 0.3 eq) and the reaction mixture was heated at reflux overnight. The mixture was filtered through a thin film of celite, which was rinsed twice with ethyl acetate. The filtrates were dried over sodium sulfate, and then adsorbed onto silica gel. The mixture was then purified by flash chromatography on silica gel eluting with 5-20% MeOH in DCM to give (2R)-4-[4-(cyclohex-1-en-1-yl)-1H-pyrazol-1-yl]-N-hydroxy-2-methyl-2-(methylsulfonyl)butanamide (5.6 mg, 3.6% yield). $^1$H NMR (400 MHz, METHANOL-d$_4$) δ 7.58 (s, 1H), 7.53 (s, 1H), 5.99 (br. s., 1H), 4.31-4.01 (m, 2H), 3.04 (s, 3H), 2.81-2.66 (m, 1H), 2.43-2.29 (m, 1H), 2.25 (d, J=1.8 Hz, 2H), 2.12 (d, J=2.7 Hz, 2H), 1.72 (td, J=2.7, 5.6 Hz, 2H), 1.67-1.58 (m, 2H), 1.54 (s, 3H). LC-MS M+H+342.2.

Example 2

(2R)-4-(4-cyclohexyl-1H-pyrazol-1-yl)-N-hydroxy-2-methyl-2-(methylsulfonyl)butanamide

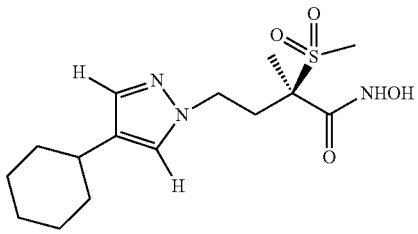

Step A: ethyl (2R)-4-(4-cyclohexyl-1H-pyrazol-1-yl)-2-methyl-2-(methylsulfonyl)butanoate A solution of ethyl (2R)-4-[4-(cyclohex-1-en-1-yl)-1H-pyrazol-1-yl]-2-methyl-2-(methylsulfonyl)butanoate (120 mg, 0.339 mmol, 1.0 eq) in MeOH (5 mL) was subjected to hydrogenation conditions (8-bar pressure, room temperature) on a Thales Nano H-cube using a 10% Pd/C catcart, (catalyst cartridge). The solution was then concentrated to give ethyl (2R)-4-(4-cyclohexyl-1H-pyrazol-1-yl)-2-methyl-2-(methylsulfonyl)butanoate (87 mg, 72% yield). LC-MS M+H+357.1.

Step B: (2R)-4-(4-cyclohexyl-1H-pyrazol-1-yl)-2-methyl-2-(methylsulfonyl)butanoic acid To a solution of (2R)-4-(4-cyclohexyl-1H-pyrazol-1-yl)-2-methyl-2-(methylsulfonyl)butanoate (87 mg, 0.24 mmol, 1 eq) in MeOH/THF (2 mL:2 mL) was added LiOH (21.5 mg, 0.512 mmol, 2.1 eq) in H$_2$O (1 mL). The mixture was allowed to stir at RT overnight. The mixture was washed with Et$_2$O and the aqueous layer acidified with 1M HCl. The solid precipitate was filtered off to give (2R)-4-(4-cyclohexyl-1H-pyrazol-1-yl)-2-methyl-2-(methylsulfonyl)butanoic acid (70 mg, 87%) which was used without further purification. LC-MS M+H+329.1.

Step C: (2R)-4-(4-cyclohexyl-1H-pyrazol-1-yl)-2-methyl-2-(methylsulfonyl)-N-(tetrahydro-2H-pyran-2-yloxy)butanamide To a solution of ((2R)-4-(4-cyclohexyl-1H-pyrazol-1-yl)-2-methyl-2-(methylsulfonyl)butanoic acid (30 mg, 0.091 mmol, 1 eq) in dichloromethane (5 mL) under nitrogen, was added DIPEA (24.9 mg, 0.193 mmol, 0.0340 mL, 2.12 eq) followed by 1-hydroxybenzotriazole monohydrate (27.0 mg, 0.176 mmol, 1.93 eq). The solution was allowed to stir for 30 minutes before being treated with O-tetrahydro-2H-pyran-2-yl-hydroxylamine (14.3 mg, 0.122 mmol, 1.34 eq) and then dimethylaminopropyl-3-ethylcarbodiimide hydrochloride (24.9 mg, 0.130 mmol, 1.43 eq). The mixture was allowed to stir for 3 hours at RT. The reaction mixture was then adsorbed onto silica gel and purified by flash chromatography eluting with 5-100% EtOAc/Hpt to give (2R)-4-(4-cyclohexyl-1H-pyrazol-1-yl)-2-methyl-2-(methylsulfonyl)-N-(tetrahydro-2H-pyran-2-yloxy)butanamide (8.8 mg, 23% yield). LC-MS M+H+428.1.

Step D: (2R)-4-(4-cyclohexyl-1H-pyrazol-1-yl)-N-hydroxy-2-methyl-2-(methylsulfonyl)butanamide To a solution of (2R)-4-(4-cyclohexyl-1H-pyrazol-1-yl)-2-methyl-2-(methylsulfonyl)-N-(tetrahydro-2H-pyran-2-yloxy)butanamide (260 mg, 0.608 mmol, 1 eq) in EtOH (6 mL), was added PPTS (45.7 mg, 0.182 mmol, 0.3 eq), and the reaction mixture was heated at reflux overnight. The crude product mixture was purified by reverse phase HPLC (Column: Phenomenex Gemini NX 150×21.2 mm 5µ; Flow rate 28 mL/min; conditions: 5-95% Water/MeOH containing 0.1% NH$_4$OH) to give (2R)-4-(4-cyclohexyl-1H-pyrazol-1-yl)-N-hydroxy-2-methyl-2-(methylsulfonyl)butanamide (137 mg, 65% yield). $^1$H NMR (400 MHz, DMSO-d$_6$) δ 7.48 (s, 1H), 7.25 (s, 1H), 4.13-4.03 (m, 1H), 3.97-3.85 (m, 1H), 3.02 (s, 3H), 2.68-2.57 (m, 1H), 2.43-2.33 (m, 1H), 2.21-2.08 (m, 1H), 1.89-1.80 (m, 1H), 1.74-1.57 (m, 3H), 1.42 (s, 3H), 1.25 (s, 6H). LC-MS M+H+344.1.

Example 3

(2R)-4-(4-cyclopentyl-1H-pyrazol-1-yl)-N-hydroxy-2-methyl-2-(methylsulfonyl)butanamide

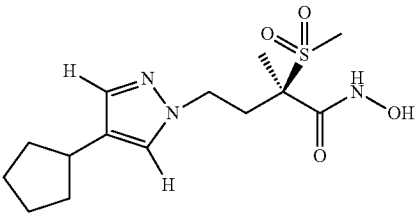 [SMILES: C[C@@](CCn1cc(C2CCCC2)cn1)(C(=O)NO)S(C)(=O)=O]

Step A: ethyl (2R)-4-[4-(cyclopent-1-en-1-yl)-1H-pyrazol-1-yl]-2-methyl-2-(methylsulfonyl)butanoate Ethyl (2R)-4-(4-iodo-1H-pyrazol-1-yl)-2-methyl-2-(methylsulfonyl)butanoate (100 mg, 0.25 mmol, 1 eq) was weighed into a 40 mL vial equipped with a septa cap. Cyclopent-1-en-1-ylboronic acid (97 mg, 0.5 mmol, 2 eq) and potassium phosphate (159 mg, 0.75 mmol, 3 eq) was added, followed by PdCl$_2$(PPh$_3$)$_2$ (18 mg, 0.025 mmol, 0.1 eq). The vial was evacuated and backfilled 3 times with nitrogen gas. 2-MeTHF (9 mL) and water (1 mL) were added to the vial and the mixture heated at 100° C. overnight. The reaction mixture was then filtered through celite and eluted with MeOH. The crude product mixture was then purified by flash chromatography on a 25 g silicycle silica gel column eluting with 20% EtOAc/Hpt to give ethyl (2R)-4-[4-(cyclopent-1-en-1-yl)-1H-pyrazol-1-yl]-2-methyl-2-(methylsulfonyl)butanoate which was used without further purification. LC-MS M+H+ 341.4.

Step B: ethyl (2R)-4-(4-cyclopentyl-1H-pyrazol-1-yl)-2-methyl-2-dimethylsulfonyl)butanoate A solution of ethyl (2R)-4-[4-(cyclopent-1-en-1-yl)-1H-pyrazol-1-yl]-2-methyl-2-(methylsulfonyl)butanoate (250 mg, 0.734 mmol, 1 eq) in MeOH (30 mL) was subjected to hydrogenation conditions (10% Pd/C catcart, 10 bar H₂ pressure) on a Thales nano H-cube. The mixture was concentrated to give ethyl (2R)-4-(4-cyclopentyl-1H-pyrazol-1-yl)-2-methyl-2-(methylsulfonyl)butanoate (100 mg, 40% yield) which was used without further purification. LC-MS M+H+ 343.4.

Step C: (2R)-4-(4-cyclopentyl-1H-pyrazol-1-yl)-2-methyl-2-(methylsulfonyl)butanoic acid To a solution of ethyl (2R)-4-(4-cyclopentyl-1H-pyrazol-1-yl)-2-methyl-2-(methylsulfonyl)butanoate (100 mg, 0.292 mmol) in dioxane (3 mL) was added a 2M LiOH solution (0.0876 mL, 1.75 mmol, 6 eq). The reaction was allowed to stir overnight at RT. The mixture was then acidified with 1M HCl. The aqueous phase was then extracted with EtOAc, dried (MgSO₄), filtered, and concentrated in vacuo to give (2R)-4-(4-cyclopentyl-1H-pyrazol-1-yl)-2-methyl-2-(methylsulfonyl)butanoic acid (92 mg, 100% yield) which was used without further purification. LC-MS M+H+315.1.

Step D: (2R)-4-(4-cyclopentyl-1H-pyrazol-1-yl)-2-methyl-2-(methylsulfonyl)-N-(tetrahydro-2H-pyran-2-yloxy)butanamide (2R)-4-(4-cyclopentyl-1H-pyrazol-1-yl)-2-methyl-2-(methylsulfonyl)butanoic acid (100 mg, 0.318 mmol, 1 eq) and CDMT (73.2 mg, 0.413 mmol, 1.3 eq) were charged into a flask. The flask was flushed with nitrogen and then 2-MeTHF (5 mL) added. To this mixture was added N-methylmorpholine (50 uL, 0.445 mmol, 1.4 eq) and the reaction mixture was stirred at RT for one hour. O-Tetrahydro-2H-pyran-2-yl-hydroxylamine (49 mg, 0.413 mmol, 1.3 eq) was added and the reaction mixture was stirred overnight at RT. Water (25 mL) was added and the organic phase was separated. The aqueous phase was extracted with ethyl acetate (50 mL). The organic phases were combined, dried over sodium sulfate, filtered and concentrated to give (2R)-4-(4-cyclopentyl-1H-pyrazol-1-yl)-2-methyl-2-(methylsulfonyl)-N-(tetrahydro-2H-pyran-2-yloxy)butanamide (100 mg, 76% yield) which was used without further purification. LC-MS M+H+414.1.

Step E: (2R)-4-(4-cyclopentyl-1H-pyrazol-1-yl)-N-hydroxy-2-methyl-2-dimethylsulfonyl)butanamide To a solution of (2R)-4-(4-cyclopentyl-1H-pyrazol-1-yl)-2-methyl-2-(methylsulfonyl)-N-(tetrahydro-2H-pyran-2-yloxy)butanamide (100 mg, 0.242 mmol) in dioxane (2 mL), DCM (2 mL) and water (500 uL) was added a 4.0M sol of HCl in dioxane (0.36 mL, 1.45 mmol). The reaction mixture was stirred at RT for 30 minutes. The solvent was removed and the crude mixture was purified by HPLC (Column: Phenomenex Luna (2) C18 150×3.0 mm 5μ; flow rate 0.75 mL/min; Gradient: 5-100% MeOH/Water containing 0.1% TFA) to give (2R)-4-(4-cyclopentyl-1H-pyrazol-1-yl)-N-hydroxy-2-methyl-2-(methylsulfonyl)butanamide (4 mg, 5% yield). LC-MS M+H+330.1.

Example 4

(2R)—N-hydroxy-2-methyl-4-(3-methyl-4-phenyl-1H-pyrazol-1-yl)-2-(methylsulfonyl)butanamide

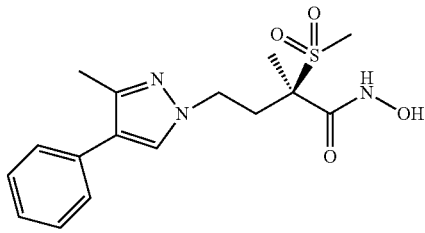 [SMILES: Cc1nn(CC[C@](C)(C(=O)NO)S(C)(=O)=O)cc1-c1ccccc1]

Step A: ethyl (2R)-2-methyl-4-(3-methyl-4-phenyl-1H-pyrazol-1-yl)-2-(methylsulfonyl)butanoate To a solution of the 3-methyl-4-phenylpyrazole (400 mg, 2.53 mmol, 1 eq) in THF (25 mL) was added cesium carbonate (2.52 g, 7.70 mmol, 3 eq) and (R)-ethyl 4-bromo-2-methyl-2-(methylsulfonyl)butanoate (950 mg, 3.31 mmol, 1.3 eq). The resulting suspension was heated to 70° C. and stirred overnight. The reaction was filtered through celite, and the filter pad was washed with ethyl acetate (2×100 mL). Combined filtrates were concentrated and the crude material was purified on a Analogix SF15-24 g column using an eluant of ethyl acetate in heptane (0-80%) to give ethyl (2R)-2-methyl-4-(3-methyl-4-phenyl-1H-pyrazol-1-yl)-2-(methylsulfonyl)butanoate (178 mg, 19.3%). LC-MS M+H+365.1.

Step B: (2R)-2-methyl-4-(3-methyl-4-phenyl-1H-pyrazol-1-yl)-2-(methylsulfonyl)butanoic acid To a solution of the ethyl (2R)-2-methyl-4-(3-methyl-4-phenyl-1H-pyrazol-1-yl)-2-(methylsulfonyl)butanoate (178 mg, 0.488 mmol, 1 eq) in THF: Methanol:water (2:2:1, 5 mL) was added potassium hydroxide (170 mg, 3.03 mmol) and reaction was stirred at RT overnight. The reaction was concentrated, and the residue was dissolved in aqueous 1N sodium hydroxide (20 mL) and washed with ethyl acetate (3×20 mL). The aqueous layer was acidified using concentrated HCl, and extracted with ethyl acetate (3×50 mL). The combined organics extracts were dried (MgSO₄), filtered, and concentrated to afford (2R)-2-methyl-4-(3-methyl-4-phenyl-1H-pyrazol-1-yl)-2-(methylsulfonyl)butanoic acid (129 mg, 78.6%). LC-MS M+H+382.1.

Step C: (2R)-2-methyl-4-(3-methyl-4-phenyl-1H-pyrazol-1-yl)-2-(methylsulfonyl)-N-(tetrahydro-2H-pyran-2-yloxy)butanamide To a solution of (2R)-2-methyl-4-(3-methyl-4-phenyl-1H-pyrazol-1-yl)-2-(methylsulfonyl)butanoic acid (129 mg, 0.38 mmol, 1 eq) in anhydrous DCM (7 mL) was added DIPEA (140 uL, 0.804 mmol, 2.1 eq), followed by HOBt (120 mg, 0.784 mmol, 2.05 eq) and the solution was stirred at RT for 30 minutes. The mixture was then treated with O-tetrahydro-2H-pyran-2-yl-hydroxylamine (70 mg, 0.60 mmol, 1.6 eq) followed by EDCI (110 mg, 0.574 mmol, 1.5 eq) and the reaction was allowed to stir at RT. The reaction mixture was concentrated in vacuo to give a crude white solid. The crude mixture was purified via flash chromatography using an Analogix SF15-12 g silica column eluting with ethyl acetate in heptane (0-80%) to give (2R)-2-methyl-4-(3-methyl-4-phenyl-1H-pyrazol-1-yl)-2-(methylsulfonyl)-N-(tetrahydro-2H-pyran-2-yloxy)butanamide (110 mg, 66% yield). LC-MS M+H+436.1.

Step D: (2R)—N-hydroxy-2-methyl-4-(3-methyl-4-phenyl-1H-pyrazol-1-yl)-2-(methylsulfonyl)butanamide To a solution of (2R)-2-methyl-4-(3-methyl-4-phenyl-1H-pyrazol-1-yl)-2-(methylsulfonyl)-N-(tetrahydro-2H-pyran-2-yloxy)butanamide (110 mg, 0.253 mmol) in EtOH (5 mL) was added PPTS (20 mg, 0.080 mmol) and the mixture was heated at reflux for 3 h. The solution was concentrated to afford a crude white solid which was purified via flash chromatography using an Analogix SF10-8 g silica column eluting with ethyl acetate in heptane (50-80%) to give (2R)—N-hydroxy-2-methyl-4-(3-methyl-4-phenyl-1H-pyrazol-1-yl)-2-(methylsulfonyl)butanamide (32 mg, 36% yield). $^1$H NMR (400 MHz, CHLOROFORM-d) δ 7.54-7.25 (m, 1H), 4.39-4.21 (m, 2H), 3.04 (s, 3H), 2.91-2.77 (m, 1H), 2.59-2.46 (m, 1H), 2.43 (s, 3H), 1.71 (s, 3H). LC-MS M+H+352.1.

Example 5

(2R)—N-hydroxy-2-methyl-4-(4-methyl-1H-pyrazol-1-yl)-2-(methylsulfonyl)butanamide

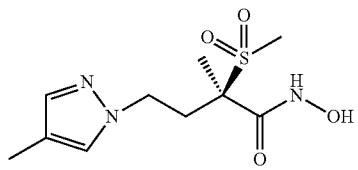 [SMILES: Cc1cnn(CC[C@](C)(C(=O)NO)S(C)(=O)=O)c1]

Step A: ethyl (2R)-2-methyl-4-(4-methyl-1H-pyrazol-1-yl)-2-(methylsulfonyl)butanoate To a solution of the 4-methylpyrazole (143 mg, 1.74 mmol, 1 eq) and (R)-ethyl 4-bromo-2-methyl-2-(methylsulfonyl)butanoate (500 mg 1.74 mmol, 1 eq) in THF (10 mL) was added cesium carbonate (2.27 g, 6.96 mmol, 4 eq). The resulting suspension was heated to 55° C. and allowed to stir overnight. The reaction was then diluted with EtOAc (10 mL) and the mixture filtered through a pad of celite, which was eluted with ~10 mL of EtOAc. The crude material was purified by flash chromatography on a 40 g silica gel column eluting with an heptane/ethyl acetate/MeOH gradient) to give ethyl (2R)-2-methyl-4-(4-methyl-1H-pyrazol-1-yl)-2-(methylsulfonyl)butanoate which was used directly in the next step. $^1$H NMR (400 MHz, CHLOROFORM-d) δ 7.27 (s, 1H), 7.13 (s, 1H), 4.30-4.11 (m, 2H), 3.03 (s, 3H), 2.80-2.71 (m, 1H), 2.51-2.41 (m, 1H), 2.04 (s, 3H), 1.66 (s, 3H). LC-MS M+H+ 289.4.

Step B: (2R)-2-methyl-4-(4-methyl-1H-pyrazol-1-yl)-2-(methylsulfonyl)butanoic acid To a solution of (2R)-2-methyl-4-(4-methyl-1H-pyrazol-1-yl)-2-(methylsulfonyl)butanoate (182 mg 0.455 mmol, 1 eq) in 2:2:1 THF-MeOH-water (6 mL) was added 0.1 M aq. LiOH and the reaction mixture was allowed to stir overnight at RT. The reaction mixture was concentrated under reduced pressure (to remove organics) to provide an aqueous solution, which was diluted with water (5 mL) and acidified to pH=2 with 1 M HCl. Upon acidification, a white precipitate formed, which was filtered, washed with water, and dried under reduced pressure to give (2R)-2-methyl-4-(4-methyl-1H-pyrazol-1-yl)-2-(methylsulfonyl)butanoic acid. LC-MS M+H+261.1.

Step C: (2R)-2-methyl-4-(4-methyl-1H-pyrazol-1-yl)-2-(methylsulfonyl)-N-(tetrahydro-2H-pyran-2-yloxy)butanamide To a solution of (2R)-2-methyl-4-(4-methyl-1H-pyrazol-1-yl)-2-(methylsulfonyl)butanoic acid (20 mg, 0.077 mmol, 1 eq) and CDMT (17.6 mg, 0.10 mmol, 1.3 eq) in THF (1 mL) was added N-methylmorpholine (10.9 mg, 0.108 mmol, 0.0120 mL, 1.4 eq) and the reaction mixture was stirred at RT for one hour. O-Tetrahydro-2H-pyran-2-yl-hydroxylamine (9.00 mg, 0.077 mmol, 1 eq) was added to the reaction mixture which was stirred overnight at RT. Water was added and the organic phase was separated. The aqueous phase was extracted with Et$_2$O. The organic phases were combined, dried over sodium sulfate, filtered and concentrated to give (2R)-2-methyl-4-(4-methyl-1H-pyrazol-1-yl)-2-(methylsulfonyl)-N-(tetrahydro-2H-pyran-2-yloxy)butanamide, (19 mg, 68%).

Step D: (2R)—N-hydroxy-2-methyl-4-(4-methyl-1H-pyrazol-1-yl)-2-(methylsulfonyl)butanamide To a solution of (2R)-2-methyl-4-(4-methyl-1H-pyrazol-1-yl)-2-(methylsulfonyl)-N-(tetrahydro-2H-pyran-2-yloxy) butanamide (19 mg, 0.053 mmol, 0.5 eq) in dichloromethane (0.5 mL) and MeOH (0.1 mL) was added a 4.0 M solution of HCl in 1,4-dioxane (0.5 mL). The reaction was allowed to stir for 1 h. The solvent was removed under reduced pressure. The crude material was triturated in pentane/Et$_2$O. The product was filtered, washed with heptane, and dried under reduced pressure to provide (2R)—N-hydroxy-2-methyl-4-(4-methyl-1H-pyrazol-1-yl)-2-(methylsulfonyl)butanamide as an off-white solid (5 mg). $^1$H NMR (400 MHz, DMSO-d$_6$) δ 7.51-7.43 (m, 1H), 7.24-7.17 (m, 1H), 3.74-3.60 (m, 1H), 3.51-3.41 (m, 1H), 3.02 (s, 3H), 2.70-2.54 (m, 1H), 2.21-2.06 (m, 1H), 1.92 (s, 3H), 1.42 (s, 3H).

Example 6

(2R)—N-hydroxy-2-methyl-2-(methylsulfonyl)-4-(4-phenyl-1H-pyrazol-1-yl)butanamide

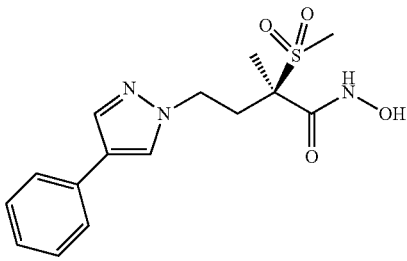 [SMILES: C[C@@](CCn1cc(-c2ccccc2)cn1)(C(=O)NO)S(C)(=O)=O]

Step A: ethyl (2R)-2-methyl-2-(methylsulfonyl)-4-(4-phenyl-1H-pyrazol-1-yl)butanoate To a solution of 2-phenylpyrazole (0.586 g, 4.06 mmol, 1 eq) in DMF (10 mL) was added Cs$_2$CO$_3$ (1.68 g), catalytic NaI and (R)-ethyl 4-bromo-2-methyl-2-(methylsulfonyl)butanoate (1.28 g, 4.47 mmol, 1.1 eq). The mixture was heated at 60° C. overnight. The mixture was then diluted with EtOAc and washed with water. The organic layer was dried (MgSO$_4$), filtered and concentrated. The crude product was purified by flash chromatography on silica gel eluting with 0-100% EtOAc to give ethyl (2R)-2-methyl-2-(methylsulfonyl)-4-(4-phenyl-1H-pyrazol-1-yl)butanoate. $^1$H NMR (400 MHz, METHANOL-d$_4$) δ 7.95 (s, 1H), 7.80 (s, 1H), 7.56-7.46 (m, 2H), 7.32 (t, J=7.7 Hz, 2H), 7.18 (s, 1H), 4.45-4.23 (m, 2H), 4.17-3.98 (m, 2H), 3.08 (s, 3H), 2.91-2.76 (m, 1H), 2.52-2.36 (m, 1H), 1.66 (s, 3H), 1.29-1.12 (m, 3H). LC-MS M+H+351.1.

Step B: (2R)-2-methyl-2-(methylsulfonyl)-4-(4-phenyl-1H-pyrazol-1-yl)butanoic acid To a solution of ethyl (2R)-2-methyl-2-(methylsulfonyl)-4-(4-phenyl-1H-pyrazol-1-yl)butanoate (1.22 g, 3.48 mmol, 1 eq) in THF-H$_2$O (15 mL:15 mL) was added LiOH (0.258 g, 10.4 mmol, 3 eq). The mixture was allowed to stir at RT overnight. The mixture was acidified with 1M HCl and extracted with EtOAc. The organic layers were combined, dried (MgSO$_4$), filtered and concentrated to give (2R)-2-methyl-2-(methylsulfonyl)-4-(4-phenyl-1H-pyrazol-1-yl)butanoic acid (0.855 g, 76 yield). $^1$H NMR (400 MHz, DMSO-d$_6$) δ 8.20 (s, 1H), 7.86 (s, 1H), 7.53 (d, J=7.4 Hz, 2H), 7.32 (t, J=7.7 Hz, 2H), 7.15 (s, 1H), 4.35-4.23 (m, 1H), 4.20-4.08 (m, 1H), 3.11 (s, 3H), 2.71-2.57 (m, 1H), 2.38-2.25 (m, 1H), 1.50 (s, 3H). LC-MS M+H+323.1.

Step C: (2R)-2-methyl-2-(methylsulfonyl)-4-(4-phenyl-1H-pyrazol-1-yl)-N-(tetrahydro-2H-pyran-2-yloxy)butanamide To a solution of (2R)-2-methyl-2-(methylsulfonyl)-4-(4-phenyl-1H-pyrazol-1-yl)butanoic acid (0.855 g, 2.65 mmol, 1 eq) in DMF (20 mL) was added DIPEA (1.06 g, 7.96 mmol, 1.45 mL, 3.eq), O-tetrahydro-2H-pyran-2-yl-hydroxylamine (0.621 g, 5.30 mmol, 2 eq) and HATU (1.54 g, 3.98 mmol, 1.5 eq). The reaction was allowed to stir at RT overnight. The mixture was diluted with EtOAc and water. The aqueous layer was extracted several times with EtOAc, dried (MgSO$_4$), filtered and concentrated. The crude product mixture was purified by flash chromatography on a 40 g silica column eluting with 0-100% EtOAc/DCM to give (2R)-2-methyl-2-(methylsulfonyl)-4-(4-phenyl-1H-pyrazol-1-yl)-N-(tetrahydro-2H-pyran-2-yloxy)butanamide (685 mg, 61% yield). LC-MS M−H 420.3.

Step D: (2R)—N-hydroxy-2-methyl-2-(methylsulfonyl)-4-(4-phenyl-1H-pyrazol-1-yl)butanamide To a solution of (2R)-2-methyl-2-(methylsulfonyl)-4-(4-phenyl-1H-pyrazol-1-yl)-N-(tetrahydro-2H-pyran-2-yloxy) butanamide (0.685 g, 1.62 mmol, 1 eq) in THF (20 mL) was added HCl (4M aq. sol.) and the reaction was allowed to stir at RT overnight. The reaction mixture was concentrated and azeotroped with MeOH to remove water to give (2R)—N-hydroxy-2-methyl-2-(methylsulfonyl)-4-(4-phenyl-1H-pyrazol-1-yl)butanamide (497 mg, 91% yield) as a white solid. $^1$H NMR (400 MHz, DMSO-d$_6$) δ 10.85-10.73 (m, 1H), 10.30-10.18 (m, 1H), 8.19 (s, 1H), 7.86 (s, 1H), 7.60-7.50 (m, 2H), 7.32 (t, J=7.7 Hz, 2H), 7.15 (s, 1H), 4.27-4.14 (m, 1H), 4.10-3.95 (m, 1H), 3.04 (s, 3H), 2.79-2.63 (m, 1H), 2.32-2.18 (m, 1H), 1.46 (s, 3H). LC-MS M+H+338.0.

Example 7

(2R)-4-(4-cyano-1H-pyrazol-1-yl)-N-hydroxy-2-methyl-2-(methylsulfonyl)butanamide

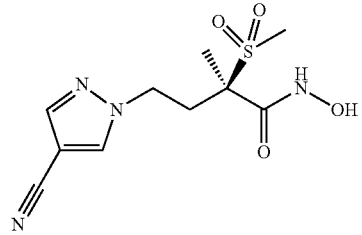 [SMILES: C[C@@](CCn1cc(C#N)cn1)(C(=O)NO)S(C)(=O)=O]

Step A: (2R)-4-(4-cyano-1H-pyrazol-1-yl)-2-methyl-2-(methylsulfonyl)butanoic acid To a solution of 4-cyanopyrazole (0.150 g, 1.61 mmol, 1 eq) in acetonitrile (10 mL) was added cesium carbonate (1.31 g, 4.03 mmol, 2.5 eq), sodium iodide (0.048 mg, 0.322 mmol, 0.2 eq) and (R)-ethyl 4-bromo-2-methyl-2-(methylsulfonyl) butanoate (0.555 g, 1.93 mmol, 1.2 eq). The mixture was heated at 50° C. overnight. The reaction mixture was cooled to room temperature and was filtered via Buchner funnel, and eluted with EtOAc. The filtrate was concentrated under reduced pressure and was diluted with up in tetrahydrofuran (5 mL) and water (5 mL). Lithium hydroxide (0.116 g, 4.83 mmol, 3 eq) was added, and the reaction mixture was allowed to stir at room temperature for four hours. The reaction mixture was concentrated under reduced pressure, diluted with ethyl acetate (10 mL), and concentrated again. This yielded (2R)-4-(4-cyano-1H-pyrazol-1-yl)-2-methyl-2-(methylsulfonyl)butanoic acid as a yellow oil, which was carried on crude in the next step. LC-MS M+H+272.2.

Step B: (2R)-4-(4-cyano-1H-pyrazol-1-yl)-2-methyl-2-(methylsulfonyl)-N-(tetrahydro-2H-pyran-2-yloxy) butanamide To a solution of the crude (2R)-4-(4-cyano-1H-pyrazol-1-yl)-2-methyl-2-(methylsulfonyl)butanoic acid in 2-methyltetrahydrofuran (20 mL) was added N-methyl morpholine (0.494 g, 4.83 mmol, 3 eq) and CDMT (0.424 g, 2.42 mmol, 1.5 eq). The solution was allowed to stir at room temperature for one hour. O-tetrahydro-2H-pyran-2-yl-hydroxylamine (0.283 g, 2.42 mmol, 1.5 eq) was added to the solution, and the reaction mixture was allowed to stir for an additional hour at room temperature. Water (20 mL) was added, and the solution was extracted with 2-methyltetrahydrofuran (100 mL). The aqueous layer was re-extracted with 2-methyltetrahydrofuran (150 mL) and the combined organic layers were washed with brine. The organic layer was dried over sodium sulfate, filtered, and concentrated. The crude product mixture was purified by flash chromatography on a 40 g silica column eluting with 70-100% EtOAc/Heptane to give (2R)-4-(4-cyano-1H-pyrazol-1-yl)-2-methyl-2-(methylsulfonyl)-N-(tetrahydro-2H-pyran-2-yloxy)butanamide (165 mg, 28% yield over two steps) as a white solid. LC-MS M−H 369.4.

Step C: (2R)-4-(4-cyano-1H-pyrazol-1-yl)-N-hydroxy-2-methyl-2-(methylsulfonyl)butanamide To a solution of (2R)-4-(4-cyano-1H-pyrazol-1-yl)-2-methyl-2-(methylsulfonyl)-N-(tetrahydro-2H-pyran-2-yloxy)butanamide (0.165 g, 0.445 mmol) in EtOH (20 mL) was added HCl (1 M solution, 5 mL). The reaction mixture was allowed to stir at room temperature overnight. The reaction mixture was concentrated and was purified via reverse-phase chromatography system, using 5%-95% acetonitrile/water with 0.1% formic acid modifier as the gradient elution solvent. Target fractions were combined and evaporated to yield (2R)-4-(4-cyano-1H-pyrazol-1-yl)-N-hydroxy-2-methyl-2-(methylsulfonyl)butanamide (21 mg, 16% yield) as a white solid. $^1$H NMR (400 MHz, DMSO-$d_6$) δ 1.47 (s, 3H), 2.16-2.33 (m, 1H), 2.59-2.80 (m, 1H), 3.04 (s, 3H), 3.96-4.17 (m, 1H), 4.18-4.39 (m, 1H), 8.05 (s, 1H) 8.57 (s, 1H), 9.24 (br. s., 1H) 10.97 (br. s., 1H). LC-MS M−H 285.3.

Example 8

(2R)—N-hydroxy-2-methyl-2-(methylsulfonyl)-4-[4-(pyrazin-2-yl)-1H-pyrazol-1-yl]butanamide

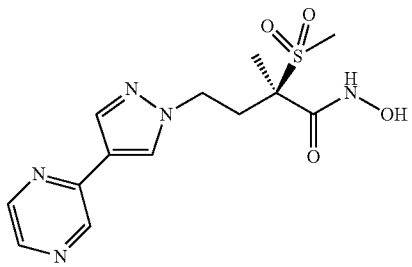 [SMILES: C[C@@](CCn1cc(-c2cnccn2)cn1)(C(=O)NO)S(C)(=O)=O]

Step A: ethyl (2R)-2-methyl-2-(methylsulfonyl)-4-[4-(pyrazin-2-yl)-1H-pyrazol-1-yl]butanoate To a solution of 2-(1H-pyrazol-4-yl)pyrazine (0.157 g, 1.07 mmol) in acetonitrile (10 mL) was added cesium carbonate (0.873 g, 2.78 mmol, 2.5 eq), sodium sulfate (0.032 g, 0.214 mmol, 0.2 eq) and (R)-ethyl 4-bromo-2-methyl-2-(methylsulfonyl)butanoate (0.4 g 1.39 mmol, 1.3 eq). The mixture was heated at 50° C. overnight. The reaction mixture was filtered over a pad of diatomateous earth. The filtrate was evaporated in vacuo. The crude product was purified by flash chromatography on silica gel eluting with 40-100% ethyl acetate/heptane to give ethyl (2R)-2-methyl-2-(methylsulfonyl)-4-[4-(pyrazin-2-yl)-1H-pyrazol-1-yl]butanoate (0.320 g, 1.39 mmol, 65% yield). LC-MS M+H+353.2.

Step B: (2R)-2-methyl-2-(methylsulfonyl)-4-[4-(pyrazin-2-yl)-1H-pyrazol-1-yl]-N-(tetrahydro-2H-pyran-2-yloxy)butanamide To a solution of ethyl (2R)-2-methyl-2-(methylsulfonyl)-4-[4-(pyrazin-2-yl)-1H-pyrazol-1-yl]butanoate (0.32 g, 0.908 mmol) in THF-$H_2O$ (20 mL:10 mL) was added lithium hydroxide (0.217 g, 9.08 mmol, 10 eq). The mixture was allowed to stir at room temperature overnight. The mixture was then acidified with 1M HCl and extracted with ethyl acetate. The organic layer was washed with brine, dried over sodium sulfate, filtered, and concentrated to dryness. The solid was taken up in 2-methyltetrahydrofuran (20 mL). N-methyl morpholine (0.185 g, 1.81 mmol, 1.4 eq) was added, followed by CDMT (0.273 g, 1.55 mmol, 1.2 eq). The reaction mixture was allowed to stir for one hour. O-Tetrahydro-2H-pyran-2-yl-hydroxylamine (0.182 g, 1.55 mmol, 1.2 eq) was added, and the reaction mixture was allowed to stir for an additional two hours. Water (20 mL) was added, and the solution was extracted with 2-MeTHF (100 mL). The aqueous layer was re-extracted with 2-MeTHF (150 mL) and the combined organic layers were washed with brine. The organic layer was dried over sodium sulfate, filtered, and concentrated. The crude was purified by flash chromatography, eluting with 0-10% MeOH/EtOAC to give (2R)-2-methyl-2-(methylsulfonyl)-4-[4-(pyrazin-2-yl)-1H-pyrazol-1-yl]-N-(tetrahydro-2H-pyran-2-yloxy)butanamide (182 mg, 33% yield). LC-MS M−H 424.1.

Step C: (2R)—N-hydroxy-2-methyl-2-(methylsulfonyl)-4-[4-(pyrazin-2-yl)-1H-pyrazol-1-yl]butanamide To a solution of (2R)-2-methyl-2-(methylsulfonyl)-4-[4-(pyrazin-2-yl)-1H-pyrazol-1-yl]-N-(tetrahydro-2H-pyran-2-yloxy)butanamide (0.182 g, 0.430 mmol) in EtOH (8 mL) was added 1M HCl (15 mL). The reaction mixture was allowed to stir at RT overnight. The reaction mixture was concentrated, and azeotroped with methanol to remove water to give (2R)—N-hydroxy-2-methyl-2-(methylsulfonyl)-4-[4-(pyrazin-2-yl)-1H-pyrazol-1-yl]butanamide (142 mg, 97% yield) as an off-white solid. $^1$H NMR (400 MHz, DMSO-$d_6$) δ 1.49 (s, 3H) 2.21-2.33 (m, 1H) 2.68-2.80 (m, 1H) 3.06 (s, 3H) 4.05-4.15 (m, 1H) 4.22-4.32 (m, 1H) 8.12 (s, 1H) 8.40 (d, J=2.54 Hz, 1H) 8.50 (s, 1H) 8.54 (dd, J=2.54, 1.56 Hz, 1H) 8.96 (d, J=1.56 Hz, 1H) 10.93 (br. s., 1H) 11.14 (s, 1H) LC-MS M+H+340.1.

Example 9

(2R)—N-hydroxy-2-methyl-2-(methylsulfonyl)-4-[4-(quinoxalin-2-yl)-1H-pyrazol-1-yl]butanamide

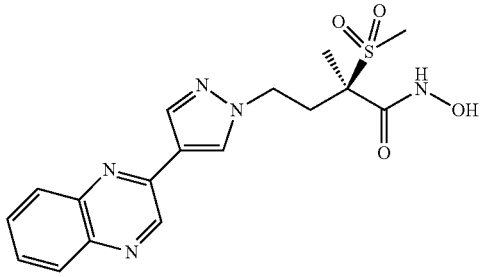 [SMILES: C[C@@](CCn1cc(-c2cnc3ccccc3n2)cn1)(C(=O)NO)S(C)(=O)=O]

Step A: ethyl (2R)-2-methyl-2-(methylsulfonyl)-4-[4-(quinoxalin-2-yl)-1H-pyrazol-1-yl]butanoate To a solution of 2-(1H-pyrazol-4-yl)quinoxaline (0.400 g, 1.39 mmol) in acetonitrile (10 mL) was added cesium carbonate (8.73 g, 2.68 mmol, 2.5 eq), sodium iodide (0.032 g, 0.214 mmol, 0.2 eq) and (R)-ethyl 4-bromo-2-methyl-2-(methylsulfonyl)butanoate (0.400 g 1.39 mmol, 1.3 eq). The reaction mixture was heated at 50° C. overnight. The reaction was filtered over a pad of diatomateous earth. The filtrate was evaporated and the crude was purified by flash chromatography on silica gel eluting with 40-100% ethyl acetate/heptane to give ethyl (2R)-2-methyl-2-(methylsulfonyl)-4-[4-(quinoxalin-2-yl)-1H-pyrazol-1-yl]butanoate (0.078 g, 14% yield) as a colorless oil. LC-MS M+H+403.1.

Step B: (2R)-2-methyl-2-(methylsulfonyl)-4-[4-(quinoxalin-2-yl)-1H-pyrazol-1-yl]butanoic acid To a solution of ethyl (2R)-2-methyl-2-(methylsulfonyl)-4-[4-(quinoxalin-2-yl)-1H-pyrazol-1-yl]butanoate (0.078 g, 0.19 mmol) in THF-H$_2$O (20 mL:10 mL) was added LiOH (0.047 g, 1.94 mmol, 10 eq). The mixture was allowed to stir at room temperature overnight. The mixture was acidified with 1M HCl and extracted with ethyl acetate. The organic layers were combined, dried over sodium sulfate, filtered, and concentrated to give (2R)-2-methyl-2-(methylsulfonyl)-4-[4-(quinoxalin-2-yl)-1H-pyrazol-1-yl]butanoic acid (0.072 g, 99% yield) as a white solid. LC-MS M+H+375.1.

Step C: (2R)-2-methyl-2-(methylsulfonyl)-4-[4-(quinoxalin-2-yl)-1H-pyrazol-1-yl]-N-(tetrahydro-2H-pyran-2-yloxy)butanamide To a solution of (2R)-2-methyl-2-(methylsulfonyl)-4-(4-phenyl-1H-pyrazol-1-yl)butanoic acid (0.076 g, 0.23 mmol) in 2-methyltetrahydrofuran (20 mL) was added N-methyl morpholine (0.034 g, 0.328 mmol, 1.4 eq), followed by CDMT (0.049 g, 0.281 mmol, 1.2 eq). The reaction mixture was allowed to stir for one hour. O-Tetrahydro-2H-pyran-2-yl-hydroxylamine (0.033 g, 0.281 mmol, 1.2 eq) was added, and the reaction was allowed to stir for an additional two hours. Water (20 mL) was added, and the solution was extracted with 2-methyltetrahydrofuran (100 mL). The aqueous layer was re-extracted with 2-MeTHF (150 mL) and the combined organic layers were washed with brine. The organic layer was dried over Na$_2$SO$_4$, filtered, and concentrated in vacuo. The crude material was purified by flash chromatography, eluting with 100% ethyl acetate to (2R)-2-methyl-2-(methylsulfonyl)-4-[4-(quinoxalin-2-yl)-1H-pyrazol-1-yl]-N-(tetrahydro-2H-pyran-2-yloxy)butanamide (54 mg, 49% yield). LC-MS M–H 472.5.

Step D: (2R)—N-hydroxy-2-methyl-2-(methylsulfonyl)-4-[4-(quinoxalin-2-yl)-1H-pyrazol-1-yl]butanamide To a solution of (2R)-2-methyl-2-(methylsulfonyl)-4-[4-(quinoxalin-2-yl)-1H-pyrazol-1-yl]-N-(tetrahydro-2H-pyran-2-yloxy)butanamide (0.685 g, 1.62 mmol, 1 eq) in EtOH (8 mL) was added 1M HCl (4 mL). The reaction mixture was allowed to stir at RT overnight. The reaction mixture was concentrated and azeotroped with MeOH to remove water to give (2R)—N-hydroxy-2-methyl-2-(methylsulfonyl)-4-[4-(quinoxalin-2-yl)-1H-pyrazol-1-yl]butanamide (38 mg, 86% yield) as a light yellow solid. $^1$H NMR (400 MHz, DMSO-d$_6$) δ 1.51 (s, 3H) 2.26-2.37 (m, 1H) 2.72-2.85 (m, 1H) 3.07 (s, 3H) 4.10-4.20 (m, 1H) 4.27-4.38 (m, 1H) 7.73 (s, 1H) 7.80 (s, 1H) 7.98 (d, J=8.39 Hz, 1H) 8.02 (d, J=0.78 Hz, 1H) 8.31 (s, 1H) 8.72 (s, 1H) 9.30 (s, 1H) 10.23 (s, 1H) 11.01 (br. s., 1H). LC-MS M+H+390.1.

Example 10

(2R)-4-[4-(1,3-benzoxazol-2-yl)-1H-pyrazol-1-yl]-N-hydroxy-2-methyl-2-(methylsulfonyl)butanamide

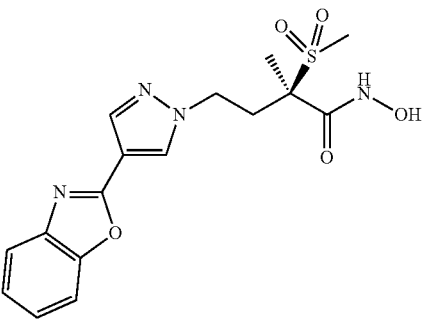 [SMILES: C[C@@](CCn1cc(-c2nc3ccccc3o2)cn1)(C(=O)NO)S(C)(=O)=O]

Step A: ethyl (2R)-4-[4-(1,3-benzoxazol-2-yl)-1H-pyrazol-1-yl]-2-methyl-2-dimethylsulfonyl)butanoate To a solution of 2-(1H-pyrazol-4-yl)-1,3-benzoxazole (0.250 g, 1.35 mmol) in acetonitrile (10 mL) was added cesium carbonate (1.10 g, 3.38 mmol, 2.5 eq), sodium iodide (0.041 g, 0.270 mmol, 0.2 eq) and (R)-ethyl 4-bromo-2-methyl-2-(methylsulfonyl)butanoate (0.504 g, 1.76 mmol, 1.3 eq). The mixture was heated at 50° C. overnight. The reaction mixture was filtered over a pad of diatomateous earth. The filtrate was evaporated and the crude was purified by flash chromatography on silica gel eluting with 10-100% ethyl acetate/heptane to give ethyl (2R)-4-[4-(1,3-benzoxazol-2-yl)-1H-pyrazol-1-yl]-2-methyl-2-(methylsulfonyl)butanoate (0.482 g, 91% yield) as a white solid. LC-MS M+H+392.1.

Step B: (2R)-4-[4-(1,3-benzoxazol-2-yl)-1H-pyrazol-1-yl]-2-methyl-2-(methylsulfonyl)butanoic acid To a solution of ethyl (2R)-4-[4-(1,3-benzoxazol-2-yl)-1H-pyrazol-1-yl]-2-methyl-2-(methylsulfonyl)butanoate (0.482 g, 1.23 mmol) in THF/H$_2$O (20 mL:10 mL) was added lithium hydroxide (0.295 g, 12.3 mmol, 10 eq). The mixture was allowed to stir at RT overnight. The mixture was acidified with 1M HCl and extracted with ethyl acetate. The organic layers were combined, dried over sodium sulfate, filtered, and concentrated to give (2R)-4-[4-(1,3-benzoxazol-2-yl)-1H-pyrazol-1-yl]-2-methyl-2-(methylsulfonyl)butanoic acid (0.420 g, 94% yield) as a white solid. LC-MS M+H+364.1.

Step C: (2R)-4-[4-(1,3-benzoxazol-2-yl)-1H-pyrazol-1-yl]-2-methyl-2-(methylsulfonyl)-N-(tetrahydro-2H-pyran-2-yloxy)butanamide To a solution of (2R)-4-[4-(1,3-benzoxazol-2-yl)-1H-pyrazol-1-yl]-2-methyl-2-(methylsulfonyl)butanoic acid (0.420 g, 1.16 mmol) in 2-MeTHF (30 mL) was added N-methyl morpholine (0.165 g, 1.62 mmol, 1.4 eq), followed by CDMT (0.244 g, 1.39 mmol, 1.2 eq). The reaction mixture was allowed to stir for one hour. O-tetrahydro-2H-pyran-2- yl-hydroxylamine (0.162 g, 1.39 mmol, 1.2 eq) was added, and the reaction was allowed to stir for an additional two hours. Water (20 mL) was added, and the solution was extracted with 2-MeTHF (100 mL). The aqueous layer was re-extracted with 2-MeTHF (150 mL) and the combined organic layers were washed with brine. The organic layer was dried over sodium sulfate, filtered, and concentrated in vacuo. The crude material was purified by flash chromatography, eluting with 30%-100% ethyl acetate/heptane to yield (2R)-4-[4-(1,3-benzoxazol-2-yl)-1H-pyrazol-1-yl]-2-methyl-2-(methylsulfonyl)-N-(tetrahydro-2H-pyran-2-yloxy)butanamide (410 mg, 77% yield) as a colorless oil. LC-MS M−H 461.3.

Step D: (2R)-4-[4-(1,3-benzoxazol-2-yl)-1H-pyrazol-1-yl]-N-hydroxy-2-methyl-2-(methylsulfonyl)butanamide To a solution of (2R)-4-[4-(1,3-benzoxazol-2-yl)-1H-pyrazol-1-yl]-2-methyl-2-(methylsulfonyl)-N-(tetrahydro-2H-pyran-2-yloxy)butanamide (0.410 g, 0.886 mmol) in EtOH (40 mL) was added 1M HCl (20 mL). The reaction mixture was allowed to stir at room temperature overnight. The reaction mixture was concentrated and was purified via reverse-phase chromatography, using 5%-95% acetonitrile/water with 0.1% formic acid modifier. The target fractions were combined and evaporated to give (2R)-4-[4-(1,3-benzoxazol-2-yl)-1H-pyrazol-1-yl]-N-hydroxy-2-methyl-2-(methylsulfonyl)butanamide (120 mg, 36% yield) as a light peach solid. $^1$H NMR (400 MHz, DMSO-d$_6$) δ 1.50 (s, 3H) 2.21-2.40 (m, 1H) 2.70-2.87 (m, 1H) 3.06 (s, 3H) 4.03-4.21 (m, 1H) 4.26-4.51 (m, 1H) 7.27-7.44 (m, 2H) 7.63-7.78 (m, 2H) 8.14 (s, 1H) 8.64 (s, 1H) 9.23 (br. s., 1H) 10.99 (br. s., 1H) LC-MS M+H+379.1.

Example 11

(2R)-4-{4-[(3-cyanophenyl)ethynyl]-1H-pyrazol-1-yl}-N-hydroxy-2-methyl-2-(methylsulfonyl)butanamide

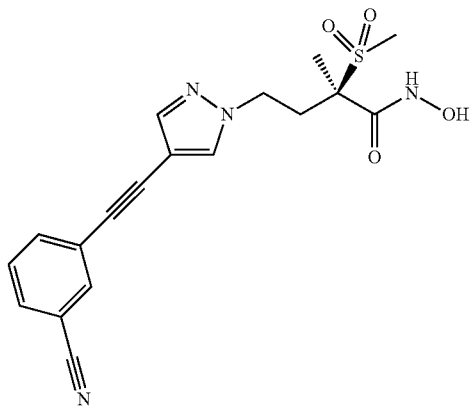 [SMILES: C[C@@](CCn1cc(C#Cc2cccc(C#N)c2)cn1)(C(=O)NO)S(C)(=O)=O]

Step A: ethyl (2R)-4-{4[(3-cyanophenyl)ethynyl]-1H-pyrazol-1-yl}-2-methyl-2-(methylsulfonyl)butanoate To a solution of 3-ethynylbenzonitrile (0.25 g, 1.26 mmol) in acetonitrile (10 mL) was added cesium carbonate (1.03 g, 3.16 mmol, 2.5 eq), sodium iodide (0.038 g, 0.253 mmol, 0.2 eq) and (R)-ethyl 4-bromo-2-methyl-2-(methylsulfonyl)butanoate (0.472 g, 1.64 mmol, 1.3 eq). The mixture was heated at 50° C. overnight. The reaction mixture was filtered over a pad of diatomateous earth. The filtrate was evaporated and the crude material was purified by flash chromatography on silica gel eluting with 10-100% ethyl acetate/heptane to give ethyl (2R)-4-{4-[(3-cyanophenyl)ethynyl]-1H-pyrazol-1-yl}-2-methyl-2-(methylsulfonyl)butanoate (0.415 g, 82% yield) as a white solid. LC-MS M+H+400.2.

Step B: (2R)-4-{4-[(3-cyanophenyl)ethynyl]-1H-pyrazol-1-yl}-2-methyl-2-(methylsulfonyl)butanoic acid To a solution of ethyl (2R)-4-{4-[(3-cyanophenyl)ethynyl]-1H-pyrazol-1-yl}-2-methyl-2-(methylsulfonyl)butanoate (0.415 g, 1.04 mmol) in THF-H$_2$O (20 mL:10 mL) was added lithium hydroxide (0.249 g, 10.4 mmol, 10 eq). The reaction mixture was allowed to stir at room temperature overnight. The reaction mixture was then acidified with 1M HCl and extracted with ethyl acetate. The organic layers were combined, dried over sodium sulfate, filtered, and concentrated to give (2R)-4-{4-[(3-cyanophenyl)ethynyl]-1H-pyrazol-1-yl}-2-methyl-2-(methylsulfonyl)butanoic acid (0.360 g, 93% yield) as a white solid. LC-MS M+H+372.1.

Step C: (2R)-4-{4-[(3-cyanophenyl)ethynyl]-1H-pyrazol-1-yl}-2-methyl-2-(methylsulfonyl)-N-(tetrahydro-2H-pyran-2-yloxy)butanamide To a solution of (2R)-4-{4-[(3-cyanophenyl)ethynyl]-1H-pyrazol-1-yl}-2-methyl-2-(methylsulfonyl)butanoic acid (0.360 g, 0.969 mmol) in 2-MeTHF (30 mL) was added N-methyl morpholine (0.139 g, 1.36 mmol, 1.4 eq), followed by CDMT (0.204 g, 1.16 mmol, 1.2 eq). The reaction mixture was allowed to stir for one hour. O-Tetrahydro-2H-pyran-2-yl-hydroxylamine (0.136 g, 1.16 mmol, 1.2 eq) was added, and the reaction mixture and was allowed to stir for an additional two hours. Water (20 mL) was added, and the solution was extracted with 2-MeTHF (100 mL). The aqueous layer was re-extracted with 2-MeTHF (150 mL), and the combined organic layers were washed with brine. The organic layer was dried over sodium sulfate, filtered, and concentrated. The crude was purified by flash chromatography, eluting with 30%-100% ethyl acetate/heptane to yield (2R)-4-{4-[(3-cyanophenyl)ethynyl]-1H-pyrazol-1-yl}-2-methyl-2-(methylsulfonyl)-N-(tetrahydro-2H-pyran-2-yloxy)butanamide (209 mg, 46% yield) as a colorless oil. LC-MS M−H 469.3.

Step D: (2R)-4-{4-[(3-cyanophenyl)ethynyl]-1H-pyrazol-1-yl}-N-hydroxy-2-methyl-2-(methylsulfonyl)butanamide To a solution of (2R)-4-{4-[(3-cyanophenyl)ethynyl]-1H-pyrazol-1-yl}-2-methyl-2-(methylsulfonyl)-N-(tetrahydro-2H-pyran-2-yloxy)butanamide (0.209 g, 0.444 mmol) in EtOH (40 mL) was added 1M HCl (20 mL). The reaction was allowed to stir at room temperature overnight. The reaction mixture was concentrated, taken back up in MeOH, and concentrated again to give (2R)-4-{4-[(3-cyanophenyl)ethynyl]-1H-pyrazol-1-yl}-N-hydroxy-2-methyl-2-(methylsulfonyl)butanamide (160 mg, 93% yield) as a white solid.
$^1$H NMR (400 MHz, DMSO-d$_6$) δ 1.46 (s, 3H), 2.18-2.30 (m, 1H), 2.64-2.77 (m, 1H), 3.05 (s, 3H), 4.04-4.12 (m, 1H), 4.17-4.28 (m, 1H), 7.55-7.63 (m, 1H), 7.74 (s, 1H), 7.76-7.86 (m, 2H), 7.91-7.96 (m, 1H), 8.18 (s, 1H), 10.89-11.04 (m, 1H). LC-MS M+H+387.1.

Example 12

(2R)—N-hydroxy-2-methyl-2-(methylsulfonyl)-4-{4-[4-(1,3-oxazol-2-yl)phenyl]-1H-pyrazol-1-yl}butanamide

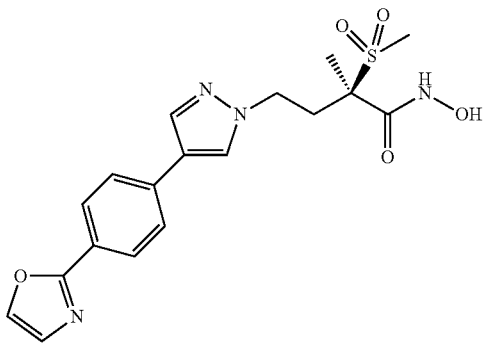 [SMILES: C[C@@](CCn1cc(-c2ccc(-c3ncco3)cc2)cn1)(C(=O)NO)S(C)(=O)=O]

Step A: ethyl (2R)-2-methyl-2-(methylsulfonyl)-4-[4-(4,4,5,5-tetramethyl-1,3,2-dioxaborolan-2-yl)-1H-pyrazol-1-yl]butanoate To a solution of 4-(4,4,5,5-tetramethyl-1,3,2-dioxaborolan-2-yl)-1H-pyrazole (0.8 g, 4.12 mmol) in acetonitrile (10 mL) was added cesium carbonate (3.36 g, 10.3 mmol, 2.5 eq), sodium iodide (0.124 g, 0.825 mmol, 0.2 eq) and (R)-ethyl 4-bromo-2-methyl-2-(methylsulfonyl)butanoate (1.54 g, 5.36 mmol, 1.3 eq). The mixture was heated at 50° C. overnight. The reaction mixture was filtered over a pad of diatomateous earth and the filtrate was evaporated to dryness. The crude product was purified by flash chromatography on silica gel eluting with 10-100% ethyl acetate/heptane to give ethyl (2R)-2-methyl-2-(methylsulfonyl)-4-[4-(4,4,5,5-tetramethyl-1,3,2-dioxaborolan-2-yl)-1H-pyrazol-1-yl]butanoate (0.810 g, 49% yield) as a white solid. LC-MS M+H+401.3.

Step B: (2R)-2-methyl-2-(methylsulfonyl)-4-{4-[4-(1,3-oxazol-2-yl)phenyl]-1H-pyrazol-1-yl}butanoic acid To a solution of ethyl (2R)-2-methyl-2-(methylsulfonyl)-4-[4-(4,4,5,5-tetramethyl-1,3,2-dioxaborolan-2-yl)-1H-pyrazol-1-yl]butanoate (0.2 g, 0.5 mmol) in MeOH (2.5 mL) in a microwave reactor vial was added 2-(4-bromophenyl)-1,3-oxazole (0.118 g, 0.525 mmol, 1.05 eq), potassium carbonate (0.214 g, 1.5 mmol, 3 eq), and palladium tetrakis (0.117 g, 0.1 mmol, 0.2 eq). The reaction mixture was irradiated at 120° C. in a microwave reactor for five minutes. The vial was allowed to cool to RT, and a solution of lithium hydroxide (0.036 g, 1.5 mmol, 3 eq) in water (2 mL) was added. The reaction mixture was allowed to stir at room temperature for one hour. The mixture was then washed with ethyl acetate (100 mL) and 1M sodium hydroxide (50 mL). The aqueous layer was separated and acidified to pH 1 with 6M HCl. The aqueous layer was extracted with ethyl acetate. The organic layer was dried over sodium sulfate, filtered, and concentrated to give (2R)-2-methyl-2-(methylsulfonyl)-4-{4-[4-(1,3-oxazol-2-yl)phenyl]-1H-pyrazol-1-yl}butanoic acid (0.125 g, 64% yield) as a white solid. LC-MS M+H+390.1.

Step C: (2R)-2-methyl-2-(methylsulfonyl)-4-{4-[4-(1,3-oxazol-2-yl)phenyl]-1H-pyrazol-1-yl}-N-(tetrahydro-2H-pyran-2-yloxy)butanamide To a solution of (2R)-2-methyl-2-(methylsulfonyl)-4-{4-[4-(1,3-oxazol-2-yl)phenyl]-1H-pyrazol-1-yl}butanoic acid (0.125 g, 0.321 mmol) in 2-methyltetrahydrofuran (20 mL) was added n-methyl morpholine (0.046 g, 0.449 mmol, 1.4 eq), followed by CDMT (0.068 g, 0.385 mmol, 1.2 eq). The reaction was allowed to stir for one hour. O-Tetrahydro-2H-pyran-2-yl-hydroxylamine (0.045 g, 0.385 mmol, 1.2 eq) was added, and the reaction mixture was allowed to stir for an additional two hours. Water (20 mL) was added, and the solution was extracted with 2-MeTHF (100 mL). The aqueous layer was re-extracted with 2-MeTHF (150 mL) and the combined organic layers were washed with brine. The organic layer was dried over sodium sulfate, filtered, and concentrated in vacuo. The crude material was purified by flash chromatography, eluting with 50%-100% ethyl acetate/heptane to yield (2R)-2-methyl-2-(methylsulfonyl)-4-{4-[4-(1,3-oxazol-2-yl)phenyl]-1H-pyrazol-1-yl}-N-(tetrahydro-2H-pyran-2-yloxy)butanamide (31 mg, 20% yield) as a colorless oil. LC-MS M–H 487.5.

Step D: (2R)—N-hydroxy-2-methyl-2-(methylsulfonyl)-4-{4-[4-(1,3-oxazol-2-yl)phenyl]-1H-pyrazol-1-yl}butanamide To a solution of (2R)-2-methyl-2-(methylsulfonyl)-4-{4-[4-(1,3-oxazol-2-yl)phenyl]-1H-pyrazol-1-yl}-N-(tetrahydro-2H-pyran-2-yloxy)butanamide (0.031 g, 0.063 mmol) in EtOH (20 mL) was added 6M HCl (5 mL). The reaction mixture was allowed to stir at room temperature overnight. The reaction mixture was concentrated and was purified via reverse-phase chromatography, using 5%-95% acetonitrile/water with 0.1% formic acid modifier. The target fractions were combined and evaporated to give (2R)—N-hydroxy-2-methyl-2-(methylsulfonyl)-4-{4-[4-(1,3-oxazol-2-yl)phenyl]-1H-pyrazol-1-yl}butanamide (6 mg, 20% yield) as a white solid. $^1$H NMR (400 MHz, CHLOROFORM-d) δ 1.22-1.30 (m, 3H), 2.44-2.59 (m, 1H), 2.76-2.92 (m, 1H), 2.94-3.11 (m, 3H), 4.19-4.45 (m, 2H), 7.23 (s, 1H), 7.45-7.56 (m, 2H), 7.66-7.74 (m, 2H), 7.80-7.86 (m, 1H), 7.93-8.06 (m, 2H). LC-MS M+H+405.1.

Example 13

N-hydroxy-2-methyl-2-(methylsulfonyl)-4-(4-phenyl-1H-imidazol-1-yl)butanamide

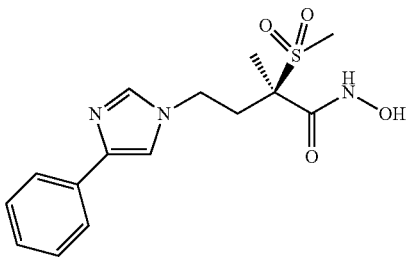 [SMILES: C[C@@](CCn1cnc(-c2ccccc2)c1)(C(=O)NO)S(C)(=O)=O]

Step A: 1-(2-iodoethyl)-4-phenyl-1H-imidazole

To a solution of 2-(4-phenyl-1H-imidazol-1-yl)ethanol (500 mg, 2.66 mmol, 1 eq) in DCM (10 mL) was added PPh₃ (778 mg, 2.96 mmol, 1.1 eq), imidazole (203 mg, 2.98 mmol, 1.1 eq) and iodine (753 mg, 2.97 mmol, 1.1 eq). The reaction mixture was allowed to stir at RT overnight. The organic layer was extracted with 1N HCl. The combined acid extracts were then adjusted to pH~8 with solid sodium carbonate. The aqueous layer was extracted 2× with Et₂O. The combined ether extracts were dried over sodium sulfate, filtered and concentrated to dryness to give 1-(2-iodoethyl)-4-phenyl-1H-imidazole (623 mg, 78% yield) which was used without further purification. LC-MS M+H+298.9.

Step B: ethyl 2-methyl-2-(methylsulfonyl)-4-(4-phenyl-1H-imidazol-1-yl)butanoate To a solution of Ethyl 2-(methylsulfonyl)propanoate (377 mg, 2.09 mmol, 1 eq) and 1-(2-iodoethyl)-4-phenyl-1H-imidazole (623 mg, 2.09 mmol, 1 eq) in DMF (7 mL) was added Cs₂CO₃ (1.70 g, 5.22 mmol, 2.5 eq) and the reaction mixture was allowed to stir overnight at RT, then for a further 24 h at 45° C. EtOAc was added and the mixture was washed with water. The organic layer was dried over MgSO₄, filtered and concentrated. The crude product mixture was purified by flash chromatography on silica gel eluting with 10-95% ethyl acetate in heptanes to give ethyl 2-methyl-2-(methylsulfonyl)-4-(4-phenyl-1H-imidazol-1-yl)butanoate (335 mg, 46% yield). LC-MS M+H+351.1.

Step C: 2-methyl-2-(methylsulfonyl)-4-(4-phenyl-1H-imidazol-1-yl)butanoic acid To a solution of ethyl 2-methyl-2-(methylsulfonyl)-4-(4-phenyl-1H-imidazol-1-yl)butanoate (335 mg, 0.956 mmol, 1 eq) in THF/MeOH/Water (4:1:1) was added lithium hydroxide monohydrate (160 mg, 3.82 mmol, 4 eq) and the mixture was allowed to stir at RT overnight. The reaction was diluted with 1 N HCl and loaded onto a 6 g MCX column. The column was washed with 1 column volume water and 2 column volumes MeOH. The washes were discarded. The column was then eluted with 0.5 N NH₃ in Methanol. The eluant was concentrated to give 2-methyl-2-(methylsulfonyl)-4-(4-phenyl-1H-imidazol-1-yl)butanoic acid (304 mg, 98% yield). LC-MS M+H+323.4.

Step D: 2-methyl-2-(methylsulfonyl)-4-(4-phenyl-1H-imidazol-1-yl)-N-(tetrahydro-2H-pyran-2-yloxy)butanamide To a solution of 2-methyl-2-(methylsulfonyl)-4-(4-phenyl-1H-imidazol-1-yl)butanoic acid (304.6 mg, 0.945 mmol, 1 eq) in DCM (10 mL) was added TEA (172 mg, 1.70 mmol, 0.237 mL, 1.80 eq), EDCI (254 mg, 1.32 mmol, 1.4 eq), HOBT (260 mg 1.70 mmol, 1.80 eq) and O— tetrahydro-2H-pyran-2-ylhydroxylamine (166 mg, 1.42 mmol, 1.5 eq). The reaction was allowed stir at RT overnight. The reaction mixture was diluted with DCM and water. The aqueous layer was extracted several times with DCM and the combined organic layers were dried (MgSO₄), filtered and concentrated. The crude product mixture was absorbed onto silica gel and purified by flash chromatography on silica gel eluting with an EtOAc-heptane gradient to give 2-methyl-2-(methylsulfonyl)-4-(4-phenyl-1H-imidazol-1-yl)-N-(tetrahydro-2H-pyran-2-yloxy)butanamide (24 mg, 6% yield). LC-MS M+H+422.6.

Step E: N-hydroxy-2-methyl-2-(methylsulfonyl)-4-(4-phenyl-1H-imidazol-1-yl)butanamide To a solution of 2-methyl-2-(methylsulfonyl)-4-(4-phenyl-1H-imidazol-1-yl)-N-(tetrahydro-2H-pyran-2-yloxy)butanamide (24.3 mg, 0.058 mmol, 1 eq) in DCM (4 mL) was added 4M HCl in dioxane (0.290 mL, 1.16 mmol, 20 eq). The reaction mixture was allowed to stir at RT for 5 mins. MeOH (100 uL) was added to the mixture. The mixture was then concentrated to dryness to give N-hydroxy-2-methyl-2-(methylsulfonyl)-4-(4-phenyl-1H-imidazol-1-yl)butanamide (8.1 mg, 37% yield). LC-MS M+H+338.5.

Example 14

(2R)—N-hydroxy-2-methyl-2-(methylsulfonyl)-4-(4-phenyl-1H-1,2,3-triazol-1-yl)butanamide

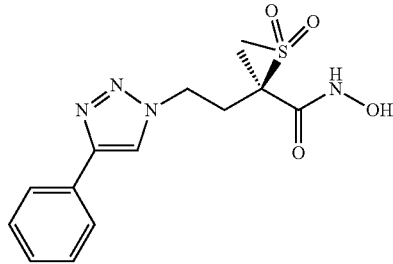 [SMILES: C[C@@](CCn1cc(-c2ccccc2)nn1)(C(=O)NO)S(C)(=O)=O]

To a solution of (2R)-4-azido-2-methyl-2-(methylsulfonyl)-N-(tetrahydro-2H-pyran-2-yloxy)butanamide (200 mg 0.622 mmol, 1 eq) in DMSO (2 mL) was added ethylnyl benzene (64 mg, 0.622 mmol, 1 eq.), CuI (24 mg, 0.124 mmol, 0.2 eq.) and Na₂CO₃ (200 mg, 1.9 mmol, 3 eq). The resulting mixture was stirred at 80° C. for 3 h. The reaction mixture was filtered to remove inorganic material and then 1 mL TFA was added. The mixture was stirred at RT for 3 h and then concentrated (using a Genevac). The crude product mixture was purified by reverse phase chromatography on a 5 g C18 column eluting with a 0 to 80% MeCN in water with 0.1% formic acid gradient, at a flow rate of 12 mL/min, to give (2R)—N-hydroxy-2-methyl-2-(methylsulfonyl)-4-(4-phenyl-1H-1,2,3-triazol-1-yl)butanamide (160 mg, 76% yield). ¹H NMR (400 MHz, DMSO-d₆) δ=11.10-10.92 (m, 1H), 9.36-9.15 (m, 1H), 8.62 (s, 1H), 7.90-7.71 (m, 2H), 7.48-7.39 (m, 2H), 7.35-7.25 (m, 1H), 4.59-4.43 (m, 1H), 4.38-4.20 (m, 1H), 3.06 (s, 3H), 2.88-2.71 (m, 1H), 2.39-2.27 (m, 1H), 1.52 (s, 3H). LC-MS M+H+339.2.

Example 15

(2R)—N-hydroxy-2-methyl-4-(5-methyl-4-phenyl-1H-1,2,3-triazol-1-yl)-2-(methylsulfonyl)butanamide

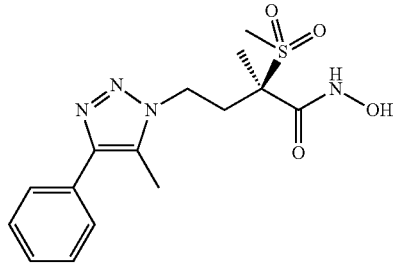 [SMILES: Cc1c(-c2ccccc2)nnn1CC[C@](C)(C(=O)NO)S(C)(=O)=O]

Step A: ethyl (2R)-2-methyl-4-(5-methyl-4-phenyl-1H-1,2,3-triazol-1-yl)-2-dimethylsulfonyl)butanoate To a solution of ethyl (2R)-4-azido-2-methyl-2-(methylsulfonyl)butanoate (2580 mg, 10.3 mmol, 1 eq) in Toluene (10 mL) and DMSO (10 mL) was added prop-1-yn-1-ylbenzene (1200 mg, 10.33 mmol, 1 eq) and 300 mg of "Ru catalyst", Chloro(pentamethylcyclopentadienyl)bis(triphenylphosphine)ruthenium(II) [CAS 92361-49-4]. The reaction mixture was heated at 80° C. for 3 h then allowed to stand at RT for 2 days. The mixture was then diluted with $CH_2Cl_2$, washed with water, dried ($MgSO_4$), filtered and concentrated to give a mixture of regioisomeric products ethyl (2R)-2-methyl-4-(5-methyl-4-phenyl-1H-1,2,3-triazol-1-yl)-2-(methylsulfonyl)butanoate and ethyl (2R)-2-methyl-4-(4-methyl-5-phenyl-1H-1,2,3-triazol-1-yl)-2-(methylsulfonyl)butanoate.

Step B: (2R)-2-methyl-4-(5-methyl-4-phenyl-1H-1,2,3-triazol-1-yl)-2-(methylsulfonyl)butanoic acid To a solution of the mixture of ethyl (2R)-2-methyl-4-(5-methyl-4-phenyl-1H-1,2,3-triazol-1-yl)-2-(methylsulfonyl)butanoate and ethyl (2R)-2-methyl-4-(4-methyl-5-phenyl-1H-1,2,3-triazol-1-yl)-2-(methylsulfonyl)butanoate (150 mg, 0.41 mmol, 1 eq) in THF (5 mL) and water (1 mL) was added LiOH (0.41 mmol, 1 eq) and the reaction mixture was allowed to stir at RT overnight. The reaction mixture was acidified with 1M HCl and extracted with $CH_2Cl_2$. The organic layer was dried ($MgSO_4$), filtered and concentrated and the crude product was used in the next step without further purification.

Step C: (2R)—N-hydroxy-2-methyl-4-(5-methyl-4-phenyl-1H-1,2,3-triazol-1-yl)-2-(methylsulfonyl)butanamide To a solution of (2R)-2-methyl-4-(5-methyl-4-phenyl-1H-1,2,3-triazol-1-yl)-2-(methylsulfonyl)butanoic acid and (2R)-2-methyl-4-(4-methyl-5-phenyl-1H-1,2,3-triazol-1-yl)-2-(methylsulfonyl)butanoic acid (115 mg, 0.341 mmol, 1 eq) in THF (5 mL) was added N-methyl morpholine (65.5 mg, 0.341 mmol, 1 eq), and CDMT (59.9 mg, 0.341 mmol, 1 eq). The reaction mixture was allowed to stir at RT for 1 h then O-tetrahydro-2H-pyran-2-yl-hydroxylamine (39.9 mg 0.341 mmol, 1 eq) was added and the reaction mixture was allowed to stir at RT for 2 days. Upon completion of the coupling reaction (as observed by LC-MS monitoring), 1 mL of TFA was added and the mixture was allowed to stir at RT for 3 h. The reaction mixture was concentrated and purified by HPLC to give (2R)—N-hydroxy-2-methyl-4-(5-methyl-4-phenyl-1H-1,2,3-triazol-1-yl)-2-(methylsulfonyl)butanamide (14 mg) as a 10:1 mixture with the corresponding regioisomer (2R)—N-hydroxy-2-methyl-4-(4-methyl-5-phenyl-1H-1,2,3-triazol-1-yl)-2-(methylsulfonyl)butanamide. $^1H$ NMR (400 MHz, METHANOL-d4) δ 7.61-7.67 (m, 2H), 7.43-7.50 (m, 2H), 7.38 (d, J=7.42 Hz, 1H), 4.51-4.63 (m, 1H), 4.36-4.48 (m, 1H), 3.06 (s, 3H), 2.85-2.93 (m, 1H), 2.51 (s, 3H), 2.43 (ddd, J=13.42, 10.10, 5.37 Hz, 1H), 1.72 (s, 3H). LC-MS M+H+353.1.

Example 16

(2R)-4-[4-(2-chloro-4-methoxyphenyl)-1H-1,2,3-triazol-1-yl]-N-hydroxy-2-methyl-2-(methylsulfonyl)butanamide

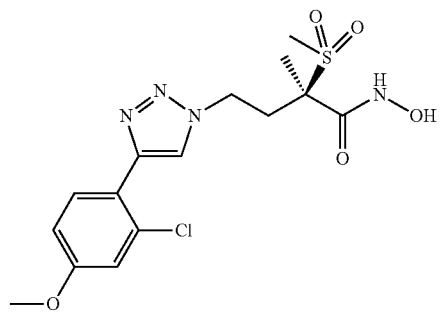 [SMILES: COc1ccc(-c2cn(CC[C@](C)(C(=O)NO)S(C)(=O)=O)nn2)c(Cl)c1]

To a solution of 2-chloro-1-ethynyl-4-methoxybenzene (15 mg, 0.093 mmol, 1 eq) and (2R)-4-azido-2-methyl-2-(methylsulfonyl)-N-(tetrahydro-2H-pyran-2-yloxy)butanamide (30 mg 0.093 mmol, 1 eq) in EtOH—$H_2O$ (7 mL:1 mL) was added sodium ascorbate (19 mg, 0.093 mmol, 1 eq) and $CuSO_4$ (9 mg, 0.037 mmol, 0.4 eq). The reaction mixture was stirred vigorously at RT overnight. The reaction mixture was concentrated to remove the EtOH/$H_2O$. The residue was dissolved in EtOAc and the $CuSO_4$ solid was filtered off. The filtrated was adsorbed onto silica and purified by flash chromatography on a 12 g silica gel column eluting with 0-100% EtOAc/Hpt to give (2R)-4-[4-(2-chloro-4-methoxyphenyl)-1H-1,2,3-triazol-1-yl]-2-methyl-2-(methylsulfonyl)-N-(tetrahydro-2H-pyran-2-yloxy)butanamide (18 mg). To a solution of (2R)-4-[4-(2-chloro-4-methoxyphenyl)-1H-1,2,3-triazol-1-yl]-2-methyl-2-(methylsulfonyl)-N-(tetrahydro-2H-pyran-2-yloxy)butanamide (18 mg, 0.037 mmol, 1 eq) in EtOH (93 mL) was added 4 M HCl. The reaction mixture was allowed to stir at RT for 3 h and then concentrated to give (2R)-4-[4-(2-chloro-4-methoxyphenyl)-1H-1,2,3-triazol-1-yl]-N-hydroxy-2-methyl-2-(methylsulfonyl)butanamide (10 mg, 67% yield). $^1H$ NMR (400 MHz, METHANOL-$d_4$) δ 8.69 (s, 1H), 7.80 (d, J=8.6 Hz, 1H), 7.15 (d, J=2.5 Hz, 1H), 7.09-7.02 (m, 1H), 4.85-4.73 (m, 1H), 4.71-4.57 (m, 1H), 3.87 (s, 3H), 3.07 (s, 4H), 2.63-2.50 (m, 1H), 1.69 (s, 3H). LC-MS M+H+403.1.

Examples 17-24

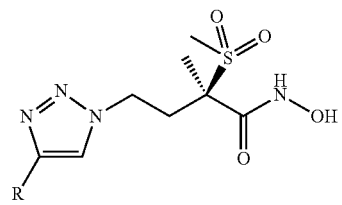

Examples 17-24 (Table 2) were prepared in parallel according to the following general procedure:

To a solution of (2R)-4-azido-2-methyl-2-(methylsulfonyl)-N-(tetrahydro-2H-pyran-2-yloxy)butanamide (1 eq) and the appropriate alkyne (2 eq) in EtOH/H$_2$O (5:1) was added CuSO$_4$ (0.4 eq) and sodium ascorbate (1 eq). The reaction mixture was allowed to stir at RT for 18 h. The reaction mixture was then filtered to remove solids and 1 M HCl solution was added. After stirring at RT for 3 h the mixture was concentrated to dryness. The crude product mixture was purified by HPLC.

TABLE 2

| Example | R | Compound Name | HPLC retention time (min)[a] | MW[b] | MS[c] |
|---|---|---|---|---|---|
| 17 | 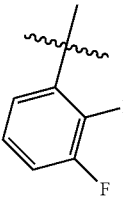 | (2R)-4-[4-(2,3-difluorophenyl)-1H-1,2,3-triazol-1-yl]-N-hydroxy-2-methyl-2-(methylsulfonyl)butanamide | 2.16 | 374.086 | 375.1119 |
| 18 | 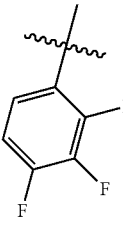 | (2R)-N-hydroxy-2-methyl-2-(methylsulfonyl)-4-[4-(2,3,4-trifluorophenyl)-1H-1,2,3-triazol-1-yl]butanamide | 2.28 | 392.0766 | 393.1049 |
| 19 | 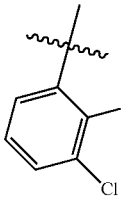 | (2R)-4-[4-(2,3-dichlorophenyl)-1H-1,2,3-triazol-1-yl]-N-hydroxy-2-methyl-2-(methylsulfonyl)butanamide | 2.4 | 406.0269 | 407.0161 |
| 20 | 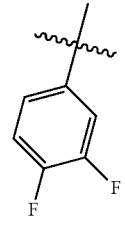 [SMILES: *c1ccc(F)c(F)c1] | (2R)-4-[4-(3,4-difluorophenyl)-1H-1,2,3-triazol-1-yl]-N-hydroxy-2-methyl-2-(methylsulfonyl)butanamide | 2.19 | 374.086 | 375.181 |
| 21 | 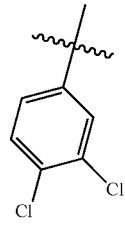 [SMILES: *c1ccc(Cl)c(Cl)c1] | (2R)-4-[4-(3,4-dichlorophenyl)-1H-1,2,3-triazol-1-yl]-N-hydroxy-2-methyl-2-(methylsulfonyl)butanamide | 2.52 | 406.0269 | 407.0463 |
| 22 | 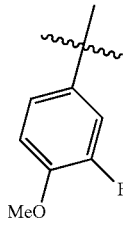 | (2R)-4-[4-(2-fluoro-4-methoxyphenyl)-1H-1,2,3-triazol-1-yl]-N-hydroxy-2-methyl-2-(methylsulfonyl)butanamide | 2.13 | 386.106 | 387.2477 |

TABLE 2-continued

| Example | R | Compound Name | HPLC retention time (min)[a] | MW[b] | MS[c] |
|---|---|---|---|---|---|
| 23 | 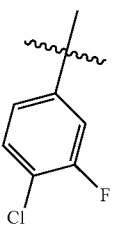 [SMILES: *c1ccc(Cl)c(F)c1] | (2R)-4-[4-(4-chloro-3-fluorophenyl)-1H-1,2,3-triazol-1-yl]-N-hydroxy-2-methyl-2-(methylsulfonyl)butanamide | 2.38 | 390.0565 | 391.1868 |
| 24 | 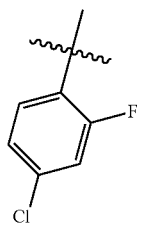 [SMILES: *c1ccc(Cl)cc1F] | (2R)-4-[4-(4-chloro-2-fluorophenyl)-1H-1,2,3-triazol-1-yl]-N-hydroxy-2-methyl-2-(methylsulfonyl)butanamide | 2.37 | 390.0565 | 391.1868 |

[a]HPLC Method Column: Waters Atlantis dC18 4.6 × 50 mm, 5 μm. Mobile Phase A 0.05% TFA in Water. Mobile Phase B: 0.05% TFA in MeCN. Flow rate: 2.0 mL/min., Gradient: 95% H$_2$O/5% MeCN linear to 5% H$_2$O/95% MeCN over 4.0 min, HOLD at 5% H$_2$O/95% MeCN to 5.0 min.
[b]Calculated exact molecular weight.
[c]MS Observed ion m/z (M + 1).

Examples 25-39

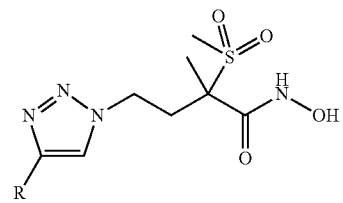

Examples 25-39 were prepared from intermediate 4-azido-2-methyl-2-(methylsulfonyl)-N-(tetrahydro-2H-pyran-2-yloxy)butanamide, in a library array format, by a method analogous to that described in examples 16-24. Final products were purified by HPLC. Characterization data for examples 25-39 is shown in Table 3.

TABLE 3

| Example | Compound Name | HPLC retention time (min) | Mw[c] | MS[d] | HPLC method[a,b] |
|---|---|---|---|---|---|
| 25 | 4-(4-{[(4-bromophenyl)sulfanyl]methyl}-1H-1,2,3-triazol-1-yl)-N-hydroxy-2-methyl-2-(methylsulfonyl)butanamide | 2.551 | 462 | 463 | A |
| 26 | 4-[4-(4-chlorophenyl)-1H-1,2,3-triazol-1-yl]-N-hydroxy-2-methyl-2-(methylsulfonyl)butanamide | 2.573 | 372.1 | 373 | A |

TABLE 3-continued

| Example | Compound Name | HPLC retention time (min) | Mw[c] | MS[d] | HPLC method[a,b] |
|---|---|---|---|---|---|
| 27 | 4-(4-{[(3-chlorophenyl)sulfanyl]methyl}-1H-1,2,3-triazol-1-yl)-N-hydroxy-2-methyl-2-(methylsulfonyl)butanamide | 2.672 | 418.1 | 419 | A |
| 28 | 4-(4-{[(2-t-butylphenyl)sulfanyl]methyl}-1H-1,2,3-triazol-1-yl)-N-hydroxy-2-methyl-2-(methylsulfonyl)butanamide | 1.701 | 440.2 | 441 | B |
| 29 | 4-(4-{[(4-chlorophenyl)sulfanyl]methyl}-1H-1,2,3-triazol-1-yl)-N-hydroxy-2-methyl-2-(methylsulfonyl)butanamide | 2.677 | 418.1 | 419 | A |
| 30 | N-hydroxy-2-methyl-2-(methylsulfonyl)-4-{4-[(naphthalen-2-yloxy)methyl]-1H-1,2,3-triazol-1-yl}butanamide | 2.807 | 418.1 | 419 | A |
| 31 | N-hydroxy-2-methyl-2-(methylsulfonyl)-4-[4-({[2-(propan-2-yl)phenyl]sulfanyl}methyl)-1H-1,2,3-triazol-1-yl]butanamide | 2.95 | 426.1 | 427 | A |
| 32 | 4-(4-{[(2-ethylphenyl)sulfanyl]methyl}-1H-1,2,3-triazol-1-yl)-N-hydroxy-2-methyl-2-(methylsulfonyl)butanamide | 2.763 | 412.1 | 413 | A |
| 33 | N-hydroxy-2-methyl-2-(methylsulfonyl)-4-(4-{[4-(trifluoromethyl)phenoxy]methyl}-1H-1,2,3-triazol-1-yl)butanamide | 1.331 | 436.1 | 437 | B |
| 34 | N-hydroxy-2-methyl-2-(methylsulfonyl)-4-{4-[(naphthalen-1-yloxy)methyl]-1H-1,2,3-triazol-1-yl}butanamide | 1.478 | 418.1 | 419 | B |
| 35 | 4-{4-[(3-t-butylphenoxy)methyl]-1H-1,2,3-triazol-1-yl}-N-hydroxy-2-methyl-2-(methylsulfonyl)butanamide | 1.687 | 424.2 | 425 | B |
| 36 | N-hydroxy-2-methyl-4-(4-{[3-(methylsulfanyl)phenoxy]methyl}-1H-1,2,3-triazol-1-yl)-2-(methylsulfonyl)butanamide | 2.216 | 414.1 | 415 | B |
| 37 | N-hydroxy-2-methyl-4-[4-(4-methylphenyl)-1H-1,2,3-triazol-1-yl]-2-(methylsulfonyl)butanamide | 2.306 | 352.1 | 353 | A |
| 38 | 4-[4-(2-bromophenyl)-1H-1,2,3-triazol-1-yl]-N-hydroxy-2-methyl-2-(methylsulfonyl)butanamide | 2.318 | 416 | 417 | A |
| 39 | 4-{4-[(2,5-dimethylphenoxy)methyl]-1H-1,2,3-triazol-1-yl}-N-hydroxy-2-methyl-2-(methylsulfonyl)butanamide | 1.829 | 396.1 | 397 | B |

[a]HPLC Method A Column: Welch XB-C18 2.1 × 50 mm 5 μm/0.05%/TFA. Mobile Phase A: 0.05% TFA in Water. Mobile Phase B: 0.05% TFA in MeCN. Flow rate: 2.0 mL/min
[b]HPLC Method B Column: Welch XB-C18 2.1 × 50 mm 5 μm/0.05% TFA. Mobile Phase A: 0.05% NH$_4$OH in Water. Mobile Phase B: 0.05% NH$_4$OH in MeCN. Flow rate: 2.0 mL/min
[c]Calculated exact molecular weight
[d]MS Observed ion m/z (M + 1)

Examples 40-92

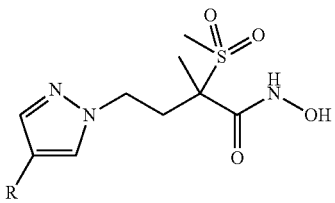

Examples 40-92 were prepared from 2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide and the appropriate aryl bromide in library format using Suzuki reaction conditions followed by acid deprotection according to either general procedures 1 or 2. Characterization data for examples 40-92 is shown in Table 4.

General Procedure 1 (for Aryl Bromides with No Heteroatom)

To a solution of 2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide (600 ul of a 0.16 M sol. in DMF, 100 μM, 1 eq) was added Aryl bromide (100 uM, 1 eq). $K_2CO_3$ (~40 mg, ~300 umol, ~3.0 eq) and water (60 uL) was added to each vial. The mixture was purged with nitrogen, then Pd(II) EnCat BINAP30 (MFCD07785498, 0.3 mmol/g Pd loading, Pd/BINAP=1.0/0.25, 50 mg, 15 μmol, 0.15 eq) was added to each vial under $N_2$ flow. The vials were sealed and heated at 80° C. for 16 h. The reaction mixtures were filtered and concentrated. The residues were dissolved in DCM (or MeOH if solubility in DCM was poor). 4M HCl in dioxane (300 μL) was added and the mixtures were allowed to shake at 30° C. for 2 h. The reaction mixtures were concentrated to dryness and the crude products purified by HPLC.

General Procedure 2 (for Aryl Bromides Containing a Heteroatom)

To a solution 2-methyl-2-(methylsulfonyl)-N-(tetrahydro-2H-pyran-2-yloxy)-4-[4-(4,4,5,5-tetramethyl-1,3,2-dioxaborolan-2-yl)-1H-pyrazol-1-yl]butanamide (800 uL of a 0.165 M sol. in dioxane, 100 μMol, 1 eq) was added $Cs_2CO_3$ (~65 mg, ~200 umol, ~2.0 eq) and 100 μL of water. The vial was purged with nitrogen then Pd-118 catalyst (~1.5 mg, ~2 μmol, ~0.02 eq) was added to each vial under $N_2$ flow. The vials were sealed and heated at 80° C. for 16 h. The aqueous portion of the mixture was removed and the organic portion was concentrated to dryness. The residues were dissolved in DCM (or MeOH if solubility in DCM was inadequate). 4M HCl in dioxane (300 μL) was added and the mixtures were allowed to shake at 30° C. for 2 h. The reaction mixtures were concentrated to dryness and the crude products purified by HPLC.

TABLE 4

| Example No. | Compound Name | HPLC retention time[a,b] (min) | MW[c] | MS[d] | HPLC method | Preparation method (1 or 2) |
|---|---|---|---|---|---|---|
| 40 | N-hydroxy-2-methyl-2-(methylsulfonyl)-4-(4-phenyl-1H-pyrazol-1-yl)butanamide | 1.793 | 337.1 | 338 | B | 1 |
| 41 | N-hydroxy-2-methyl-4-[4-(4-methylphenyl)-1H-pyrazol-1-yl]-2-(methylsulfonyl)butanamide | 1.939 | 351.1 | 352 | B | 1 |
| 42 | N-hydroxy-2-methyl-4-[4-(3-methylphenyl)-1H-pyrazol-1-yl]-2-(methylsulfonyl)butanamide | 1.944 | 351.1 | 352 | B | 1 |
| 43 | N-hydroxy-2-methyl-4-[4-(2-methylphenyl)-1H-pyrazol-1-yl]-2-(methylsulfonyl)butanamide | 1.914 | 351.1 | 352 | B | 1 |
| 44 | N-hydroxy-4-[4-(3-hydroxyphenyl)-1H-pyrazol-1-yl]-2-methyl-2-(methylsulfonyl)butanamide | 2.226 | 353.1 | 354 | A | 1 |
| 45 | 4-[4-(2-fluorophenyl)-1H-pyrazol-1-yl]-N-hydroxy-2-methyl-2-(methylsulfonyl)butanamide | 2.64 | 355.1 | 356 | A | 1 |
| 46 | 4-[4-(2-cyanophenyl)-1H-pyrazol-1-yl]-N-hydroxy-2-methyl-2-(methylsulfonyl)butanamide | 1.762 | 362.1 | 363 | B | 1 |
| 47 | 4-[4-(4-cyanophenyl)-1H-pyrazol-1-yl]-N-hydroxy-2-methyl-2-(methylsulfonyl)butanamide | 1.722 | 362.1 | 363 | B | 1 |
| 48 | 4-[4-(3-cyanophenyl)-1H-pyrazol-1-yl]-N-hydroxy-2-methyl-2-(methylsulfonyl)butanamide | 2.508 | 362.1 | 363 | A | 1 |

TABLE 4-continued

| Example No. | Compound Name | HPLC retention time[a,b] (min) | MW[c] | MS[d] | HPLC method | Preparation method (1 or 2) |
|---|---|---|---|---|---|---|
| 49 | N-hydroxy-4-[4-(4-hydroxy-2-methylphenyl)-1H-pyrazol-1-yl]-2-methyl-2-(methylsulfonyl)butanamide | 2.22 | 367.1 | 368 | A | 1 |
| 50 | N-hydroxy-4-[4-(4-hydroxy-3-methylphenyl)-1H-pyrazol-1-yl]-2-methyl-2-(methylsulfonyl)butanamide | 2.287 | 367.1 | 368 | A | 1 |
| 51 | N-hydroxy-4-[4-(3-methoxyphenyl)-1H-pyrazol-1-yl]-2-methyl-2-(methylsulfonyl)butanamide | 2.607 | 367.1 | 368 | A | 1 |
| 52 | 4-[4-(4-fluoro-3-methylphenyl)-1H-pyrazol-1-yl]-N-hydroxy-2-methyl-2-(methylsulfonyl)butanamide | 2.829 | 369.1 | 370 | A | 1 |
| 53 | 4-[4-(3-fluoro-2-methylphenyl)-1H-pyrazol-1-yl]-N-hydroxy-2-methyl-2-(methylsulfonyl)butanamide | 2.798 | 369.1 | 370 | A | 1 |
| 54 | 4-[4-(5-chloropyridin-2-yl)-1H-pyrazol-1-yl]-N-hydroxy-2-methyl-2-(methylsulfonyl)butanamide | 2.421 | 372.1 | 373 | A | 1 |
| 55 | 4-[4-(2,4-difluorophenyl)-1H-pyrazol-1-yl]-N-hydroxy-2-methyl-2-(methylsulfonyl)butanamide | 2.724 | 373.1 | 374 | A | 1 |
| 56 | 4-[4-(2,5-difluorophenyl)-1H-pyrazol-1-yl]-N-hydroxy-2-methyl-2-(methylsulfonyl)butanamide | 2.708 | 373.1 | 374 | A | 1 |
| 57 | N-hydroxy-2-methyl-2-(methylsulfonyl)-4-[4-(40-92 be)-1H-pyrazol-1-yl]butanamide | 2.075 | 377.1 | 378 | A | 1 |
| 58 | 4-[4-(2,3-dihydro-1-benzofuran-5-yl)-1H-pyrazol-1-yl]-N-hydroxy-2-methyl-2-(methylsulfonyl)butanamide | 2.551 | 379.1 | 380 | A | 1 |
| 59 | 4-[4-(3-cyano-4-fluorophenyl)-1H-pyrazol-1-yl]-N-hydroxy-2-methyl-2-(methylsulfonyl)butanamide | 2.616 | 380.1 | 381 | A | 1 |
| 60 | 4-[4-(3-fluoro-4-methoxyphenyl)-1H-pyrazol-1-yl]-N-hydroxy-2-methyl-2-(methylsulfonyl)butanamide | 2.614 | 385.1 | 386 | A | 1 |
| 61 | N-hydroxy-2-methyl-2-(methylsulfonyl)-4-[4-(3-oxo-2,3-dihydro-1H-inden-5-yl)-1H-pyrazol-1-yl]butanamide | 2.444 | 391.1 | 392 | A | 1 |
| 62 | N-hydroxy-2-methyl-2-(methylsulfonyl)-4-[4-(1-oxo-2,3-dihydro-1H-inden-5-yl)-1H-pyrazol-1-yl]butanamide | 2.36 | 391.1 | 392 | A | 1 |
| 63 | 4-[4-(2,3-dihydro-1,4-benzodioxin-6-yl)-1H-pyrazol-1-yl]-N-hydroxy-2-methyl-2-(methylsulfonyl)butanamide | 2.519 | 395.1 | 396 | A | 1 |
| 64 | 4-[4-(3-chloro-4-cyanophenyl)-1H-pyrazol-1-yl]-N-hydroxy-2-methyl-2-(methylsulfonyl)butanamide | 2.701 | 396.1 | 397 | A | 1 |

TABLE 4-continued

| Example No. | Compound Name | HPLC retention time[a,b] (min) | MW[c] | MS[d] | HPLC method | Preparation method (1 or 2) |
|---|---|---|---|---|---|---|
| 65 | 4-[4-(3,4-dimethoxyphenyl)-1H-pyrazol-1-yl]-N-hydroxy-2-methyl-2-(methylsulfonyl)butanamide | 2.421 | 397.1 | 398 | A | 1 |
| 66 | 4-{4-[4-(1-cyanocyclopropyl)phenyl]-1H-pyrazol-1-yl}-N-hydroxy-2-methyl-2-(methylsulfonyl)butanamide | 2.655 | 402.1 | 403 | A | 1 |
| 67 | N-hydroxy-2-methyl-4-[4-(2-methylquinolin-6-yl)-1H-pyrazol-1-yl]-2-(methylsulfonyl)butanamide | 1.958 | 402.1 | 403 | A | 1 |
| 68 | 4-{4-[3-(difluoromethoxy)phenyl]-1H-pyrazol-1-yl}-N-hydroxy-2-methyl-2-(methylsulfonyl)butanamide | 1.943 | 403.1 | 404 | B | 1 |
| 69 | 4-[4-(3-aminoisoquinolin-6-yl)-1H-pyrazol-1-yl]-N-hydroxy-2-methyl-2-(methylsulfonyl)butanamide | 1.643 | 403.1 | 404 | B | 1 |
| 70 | N-hydroxy-2-methyl-2-(methylsulfonyl)-4-{4-[4-(1H-pyrazol-3-yl)phenyl]-1H-pyrazol-1-yl}butanamide | 2.342 | 403.1 | 404 | A | 1 |
| 71 | N-hydroxy-2-methyl-2-(methylsulfonyl)-4-{4-[3-(1H-pyrazol-3-yl)phenyl]-1H-pyrazol-1-yl}butanamide | 2.433 | 403.1 | 404 | A | 1 |
| 72 | N-hydroxy-2-methyl-2-(methylsulfonyl)-4-{4-[4-(1,3-oxazol-5-yl)phenyl]-1H-pyrazol-1-yl}butanamide | 2.47 | 404.1 | 405 | A | 1 |
| 73 | N-hydroxy-2-methyl-2-(methylsulfonyl)-4-{4-[4-(1,2-oxazol-5-yl)phenyl]-1H-pyrazol-1-yl}butanamide | 2.598 | 404.1 | 405 | A | 1 |
| 74 | N-hydroxy-2-methyl-2-(methylsulfonyl)-4-{4-[3-(1,2-oxazol-5-yl)phenyl]-1H-pyrazol-1-yl}butanamide | 2.638 | 404.1 | 405 | A | 1 |
| 75 | N-hydroxy-2-methyl-2-(methylsulfonyl)-4-[4-(8-oxo-5,6,7,8-tetrahydronaphthalen-2-yl)-1H-pyrazol-1-yl]butanamide | 2.626 | 405.1 | 406 | A | 1 |
| 76 | N-hydroxy-2-methyl-2-(methylsulfonyl)-4-{4-[5-(trifluoromethyl)pyridin-2-yl]-1H-pyrazol-1-yl}butanamide | 1.856 | 406.1 | 407 | B | 2 |
| 77 | N-hydroxy-2-methyl-2-(methylsulfonyl)-4-{4-[6-(trifluoromethyl)pyridin-3-yl]-1H-pyrazol-1-yl}butanamide | 2.612 | 406.1 | 407 | A | 2 |
| 78 | 4-[4-(3-cyano-4-ethoxyphenyl)-1H-pyrazol-1-yl]-N-hydroxy-2-methyl-2-(methylsulfonyl)butanamide | 2.723 | 406.1 | 407 | A | 2 |
| 79 | N-hydroxy-2-methyl-4-[4-(2-methyl-1,3-benzothiazol-6-yl)-1H-pyrazol-1-yl]-2-(methylsulfonyl)butanamide | 2.501 | 408.1 | 409 | A | 2 |

TABLE 4-continued

| Example No. | Compound Name | HPLC retention time[a,b] (min) | MW[c] | MS[d] | HPLC method | Preparation method (1 or 2) |
|---|---|---|---|---|---|---|
| 80 | 4-[4-(2-amino-1,3-benzothiazol-6-yl)-1H-pyrazol-1-yl]-N-hydroxy-2-methyl-2-(methylsulfonyl)butanamide | 1.955 | 409.1 | 410 | A | 2 |
| 81 | N-hydroxy-2-methyl-4-{4-[6-(2-methylpropoxy)pyridin-3-yl]-1H-pyrazol-1-yl}-2-(methylsulfonyl)butanamide | 2.824 | 410.2 | 411 | A | 2 |
| 82 | N-hydroxy-2-methyl-4-{4-[4-(1-methyl-1H-pyrazol-5-yl)phenyl]-1H-pyrazol-1-yl}-2-(methylsulfonyl)butanamide | 2.509 | 417.1 | 418 | A | 2 |
| 83 | 4-[4-(1-benzyl-1H-imidazol-4-yl)-1H-pyrazol-1-yl]-N-hydroxy-2-methyl-2-(methylsulfonyl)butanamide | 2.112 | 417.1 | 418 | A | 2 |
| 84 | N-hydroxy-2-methyl-4-{4-[4-(3-methyl-1H-pyrazol-5-yl)phenyl]-1H-pyrazol-1-yl}-2-(methylsulfonyl)butanamide | 2.371 | 417.1 | 418 | A | 2 |
| 85 | 4-{4-[3-(5-amino-1H-pyrazol-3-yl)phenyl]-1H-pyrazol-1-yl}-N-hydroxy-2-methyl-2-(methylsulfonyl)butanamide | 2.097 | 418.1 | 419 | A | 2 |
| 86 | 6-{1-[4-(hydroxyamino)-3-methyl-3-(methylsulfonyl)-4-oxobutyl]-1H-pyrazol-4-yl}-1H-indole-2-carboxamide | 2.203 | 419.1 | 420 | A | 2 |
| 87 | 5-{1-[4-(hydroxyamino)-3-methyl-3-(methylsulfonyl)-4-oxobutyl]-1H-pyrazol-4-yl}-1H-indole-2-carboxamide | 2.124 | 419.1 | 420 | A | 2 |
| 88 | N-hydroxy-2-methyl-2-(methylsulfonyl)-4-{4-[3-(trifluoromethoxy)phenyl]-1H-pyrazol-1-yl}butanamide | 3.026 | 421.1 | 422 | A | 2 |
| 89 | 4-{4-[1-(4-fluorophenyl)-1H-imidazol-4-yl]-1H-pyrazol-1-yl}-N-hydroxy-2-methyl-2-(methylsulfonyl)butanamide | 2.108 | 421.1 | 422 | A | 2 |
| 90 | N-hydroxy-2-methyl-2-(methylsulfonyl)-4-{4-[4-(1,2,3-thiadiazol-4-yl)phenyl]-1H-pyrazol-1-yl}butanamide | 1.852 | 421.1 | 422 | B | 2 |
| 91 | 4-[4-(2-ethyl-1,3-benzothiazol-6-yl)-1H-pyrazol-1-yl]-N-hydroxy-2-methyl-2-(methylsulfonyl)butanamide | 2.701 | 422.1 | 423 | A | 2 |
| 92 | N-hydroxy-2-methyl-4-{4-[4-(2-methylpyrimidin-4-yl)phenyl]-1H-pyrazol-1-yl}-2-(methylsulfonyl)butanamide | 2.32 | 429.1 | 430 | A | 2 |

[a]HPLC Method A
Column: Welch XB-C18 2.1 × 50 mm 5 μm/0.05% TFA. Mobile Phase A: 0.05% TFA in Water. Mobile Phase B: 0.05% TFA in MeCN. Flow rate: 2.0 mL/min
[b]HPLC Method B
Column: Welch XB-C18 2.1 × 50 mm 5 μm/0.05% TFA. Mobile Phase A: 0.05% NH$_4$OH in Water. Mobile Phase B: 0.05% NH$_4$OH in MeCN. Flow rate: 2.0 mL/min
[c]Calculated exact molecular weight
[d]MS Observed ion m/z (M + 1).

Biological Examples

In order to assess the compounds biological activity, selected in-vitro assays were conducted on selected compounds of Formula I. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as $IC_{50}$). Additionally, MICs (minimal inhibitory concentrations) were determined for several bacteria. The specific protocols are described below:

A) $IC_{50}$ Assay, LpxC Enzyme from *P. Aeruginosa* Labeled as PA LpxC Enzyme $IC_{50}$):

$IC_{50}$ determination in the LpxC enzyme assay was carried out in a similar manner to that described by Malikzay et al in the 2006 Poster, Screening LpxC (UDP-3-O—(R-3-hydroxymyristoyl)-GlcNAc deacetylase) using BioTrove RapidFire HTS Mass Spectrometry (aNew Lead Discovery and binflammation and Infectious Disease, cStructural Chemistry, Schering-Plough Research Institute, Kenilworth, N.J. 07033, (BioTrove, Inc. 12 Gill St., Suite 4000, Woburn, Mass. 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1 N HCl was added to stop the enzyme reaction, the plates were centrifuged, and then processed with the BioTrove Rapidfire HTMS Mass Spectrometry System. A no-enzyme control was used in calculating the $IC_{50}$ values from the percent conversion values.

B) MIC Determinations:

The in vitro antibacterial activity of compounds described in the Examples was evaluated by minimum inhibitory concentration (MIC) testing according to Clinical and Laboratory Standards Institute (CLSI) Guidelines. See: Clinical and Laboratory Standards Institute. Methods for Dilution Antimicrobial Susceptibility Tests for Bacteria that Grow Aerobically; Approved Standard-Eighth Edition. CLSI document M7-A8 [ISBN 1-56238-689-1]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Twentieth Informational Supplement. CLSI document M100-S20 [ISBN1-56238-716-2]. Clinical and Laboratory Standards Institute.

The MIC determination is a standard laboratory method for evaluating the antibacterial activity of a compound. The MIC represents the lowest drug concentration that inhibits visible growth of bacteria following overnight incubation. In order to determine the MIC value, a range of drug concentrations (e.g. 0.06 μg/mL to 64 μg/mL) are incubated with a defined strain of bacteria. Typically, the drug concentration range is broken down into 2-fold increments (e.g. 0.06 μg/mL, 0.12 μg/mL. 0.25 μg/mL, 0.50 μg/mL, 1.0 μg/mL, etc.) and the various drug concentrations are all individually incubated overnight with approximately the same number of bacteria. The MIC is then determined by visually inspecting the drug effect at each concentration, and identifying the lowest drug concentration that has inhibited bacterial growth as compared to the drug free control. Typically, bacteria continue to grow at drug concentrations lower than the MIC and don't grow at concentrations at and above the MIC.

The MIC values described in Tables 2 and 3 below were derived from assays wherein each test compound was evaluated in duplicate. In cases where the duplicate values varied by 0-2-fold, the lower of the two values was reported below. Generally speaking, if the duplicate values varied by more than 2-fold, the assay was considered non-valid and was repeated until the variation between duplicate runs was ≤2-fold. In line with the CLSI guidelines referred to above, both control organisms and reference compounds were utilized in each MIC assay to provide proper quality control. MIC values generated with these control organisms and reference compounds were required to fall within a defined range for the assay to be considered valid and be included herein. Those skilled in the art will recognize that MIC values can and do vary from experiment to experiment. Generally speaking, it should be recognized that MIC values often vary +/−2-fold from experiment to experiment. While a single MIC is reported for each compound and each microorganism, the reader should not conclude that each compound was only tested once. Several of the compounds were subjected to multiple tests. The data reported in Tables 2 and 3 is reflective of the compounds relative activity and different MICs may have been generated on these occasions in line with the guidelines described above.

The following bacterial strains were used in these MIC determinations:

(1) *Acinetobacter baumannii/haemolyticus*: Multidrug-resistant clinical isolate labeled as AB-3167 in Table 5;

(2) *Escherichia coli* EC-1: VOGEL, mouse virulent labeled as EC-1 in Table 5;

(3) *Klebsiella pneumoniae*: Ciprofloxacin-resistant isolate, expresses extended-spectrum beta-lactamases (ESBL), clinical isolate, labeled as KP-3700 in Table 5.

(4) *Pseudomonas aeruginosa* UI-18: Wild-type, labeled as PA-7 in Table 5;

TABLE 5

Biological Data

| Ex. No. | Compound Name | PA: $IC_{50}$ (nM) | AB-3167 (μg/ml) | EC-1 (μg/ml) | KP-3700 (μg/ml) | PA-7 (μg/ml) |
| --- | --- | --- | --- | --- | --- | --- |
| 1 | (2R)-4-[4-(cyclohex-1-en-1-yl)-1H-pyrazol-1-yl]-N-hydroxy-2-methyl-2-(methylsulfonyl)butanamide | | >64.0 | 8 | 16 | 1 |
| 2 | (2R)-4-(4-cyclohexyl-1H-pyrazol-1-yl)-N-hydroxy-2-methyl-2-(methylsulfonyl)butanamide | 0.752 | >64.0 | 32 | 64 | 1 |
| 3 | (2R)-4-(4-cyclopentyl-1H-pyrazol-1-yl)-N-hydroxy-2-methyl-2-(methylsulfonyl)butanamide | 14.3 | 64 | 64 | 64 | 8 |

TABLE 5-continued

Biological Data

| Ex. No. | Compound Name | PA: IC$_{50}$ (nM) | AB-3167 (μg/ml) | EC-1 (μg/ml) | KP-3700 (μg/ml) | PA-7 (μg/ml) |
|---|---|---|---|---|---|---|
| 4 | (2R)-N-hydroxy-2-methyl-4-(3-methyl-4-phenyl-1H-pyrazol-1-yl)-2-(methylsulfonyl)butanamide | 14.6 | >64.0 | 8 | 32 | 8 |
| 5 | (2R)-N-hydroxy-2-methyl-4-(4-methyl-1H-pyrazol-1-yl)-2-(methylsulfonyl)butanamide | >100 | >64.0 | >64.0 | >64.0 | 32 |
| 6 | (2R)-N-hydroxy-2-methyl-2-(methylsulfonyl)-4-(4-phenyl-1H-pyrazol-1-yl)butanamide | 1.61 | >64.0 | 16 | 64 | 1 |
| 7 | (2R)-4-(4-cyano-1H-pyrazol-1-yl)-N-hydroxy-2-methyl-2-(methylsulfonyl)butanamide | 620 | >64.0 | >64.0 | >64.0 | >64.0 |
| 8 | (2R)-N-hydroxy-2-methyl-2-(methylsulfonyl)-4-[4-(pyrazin-2-yl)-1H-pyrazol-1-yl]butanamide | >100 | >64.0 | >64.0 | >64.0 | >64.0 |
| 9 | (2R)-N-hydroxy-2-methyl-2-(methylsulfonyl)-4-(quinoxalin-2-yl)-1H-pyrazol-1-yl]butanamide | 19 | >64.0 | >64.0 | >64.0 | >64.0 |
| 10 | (2R)-4-[4-(1,3-benzoxazol-2-yl)-1H-pyrazol-1-yl]-N-hydroxy-2-methyl-2-(methylsulfonyl)butanamide | 13.8 | 32 | 32 | >64.0 | 32 |
| 11 | (2R)-4-{4-[(3-cyanophenyl)ethynyl]-1H-pyrazol-1-yl}-N-hydroxy-2-methyl-2-(methylsulfonyl)butanamide | 12.1 | >64.0 | 32 | 64 | 16 |
| 12 | (2R)-N-hydroxy-2-methyl-2-(methylsulfonyl)-4-{4-[4-(1,3-oxazol-2-yl)phenyl]-1H-pyrazol-1-yl}butanamide | 0.963 | | | | |
| 13 | N-hydroxy-2-methyl-2-(methylsulfonyl)-4-(4-phenyl-1H-imidazol-1-yl)butanamide | | >64.0 | >64.0 | >64.0 | >64.0 |
| 14 | (2R)-N-hydroxy-2-methyl-2-(methylsulfonyl)-4-(4-phenyl-1H-1,2,3-triazol-1-yl)butanamide | 0.85 | >64.0 | 32 | 32 | 2 |
| 15 | (2R)-N-hydroxy-2-methyl-4-(5-methyl-4-phenyl-1H-1,2,3-triazol-1-yl)-2-(methylsulfonyl)butanamide | 21.3 | >64.0 | >64.0 | >64.0 | 32 |
| 16 | (2R)-4-[4-(2-chloro-4-methoxyphenyl)-1H-1,2,3-triazol-1-yl]-N-hydroxy-2-methyl-2-(methylsulfonyl)butanamide | 4.71 | >64.0 | 8 | 32 | 8 |
| 17 | (2R)-4-[4-(2,3-difluorophenyl)-1H-1,2,3-triazol-1-yl]-N-hydroxy-2-methyl-2-(methylsulfonyl)butanamide | 8.08 | >64.0 | 32 | 64 | 4 |
| 18 | (2R)-N-hydroxy-2-methyl-2-(methylsulfonyl)-4-[4-(2,3,4-trifluorophenyl)-1H-1,2,3-triazol-1-yl]butanamide | 3.29 | | | | |
| 19 | (2R)-4-[4-(2,3-dichlorophenyl)-1H-1,2,3-triazol-1-yl]-N-hydroxy-2-methyl-2-(methylsulfonyl)butanamide | 1.95 | >64.0 | 8 | 16 | 4 |
| 20 | (2R)-4-[4-(3,4-difluorophenyl)-1H-1,2,3-triazol-1-yl]-N-hydroxy-2-methyl-2-(methylsulfonyl)butanamide | 1.87 | >64.0 | 32 | >64.0 | 4 |
| 21 | (2R)-4-[4-(3,4-dichlorophenyl)-1H-1,2,3-triazol-1-yl]-N-hydroxy-2-methyl-2-(methylsulfonyl)butanamide | 1.67 | >64.0 | 16 | 32 | 2 |
| 22 | (2R)-4-[4-(2-fluoro-4-methoxyphenyl)-1H-1,2,3-triazol-1-yl]-N-hydroxy-2-methyl-2-(methylsulfonyl)butanamide | 1.2 | >64.0 | 4 | 32 | 2 |
| 23 | (2R)-4-[4-(4-chloro-3-fluorophenyl)-1H-1,2,3-triazol-1-yl]-N-hydroxy-2-methyl-2-(methylsulfonyl)butanamide | 0.912 | >64.0 | 8 | 64 | 2 |
| 24 | (2R)-4-[4-(4-chloro-2-fluorophenyl)-1H-1,2,3-triazol-1-yl]-N-hydroxy-2-methyl-2-(methylsulfonyl)butanamide | 0.657 | >64.0 | 2 | 4 | 1 |
| 25 | 4-(4-{[(4-bromophenyl)sulfanyl]methyl}-1H-1,2,3-triazol-1-yl)-N-hydroxy-2-methyl-2-(methylsulfonyl)butanamide | 10.1 | | | | |
| 26 | 4-[4-(4-chlorophenyl)-1H-1,2,3-triazol-1-yl]-N-hydroxy-2-methyl-2-(methylsulfonyl)butanamide | 2.87 | >64.0 | 32 | 32 | 4 |

TABLE 5-continued

Biological Data

| Ex. No. | Compound Name | PA: IC$_{50}$ (nM) | AB-3167 (μg/ml) | EC-1 (μg/ml) | KP-3700 (μg/ml) | PA-7 (μg/ml) |
|---|---|---|---|---|---|---|
| 27 | 4-(4-{[(3-chlorophenyl)sulfanyl]methyl}-1H-1,2,3-triazol-1-yl)-N-hydroxy-2-methyl-2-(methylsulfonyl)butanamide | 12.2 | >64.0 | >64.0 | >64.0 | 64 |
| 28 | 4-(4-{[(2-te-butylphenyl)sulfanyl]methyl}-1H-1,2,3-triazol-1-yl)-N-hydroxy-2-methyl-2-(methylsulfonyl)butanamide | 174 | >64.0 | >64.0 | >64.0 | >64.0 |
| 29 | 4-(4-{[(4-chlorophenyl)sulfanyl]methyl}-1H-1,2,3-triazol-1-yl)-N-hydroxy-2-methyl-2-(methylsulfonyl)butanamide | 8.82 | >64.0 | >64.0 | >64.0 | 32 |
| 30 | N-hydroxy-2-methyl-2-(methylsulfonyl)-4-{4-[(naphthalen-2-yloxy)methyl]-1H-1,2,3-triazol-1-yl}butanamide | 3.76 | >64.0 | >64.0 | >64.0 | 32 |
| 31 | N-hydroxy-2-methyl-2-(methylsulfonyl)-4-[4-({[2-(propan-2-yl)phenyl]sulfanyl}methyl)-1H-1,2,3-triazol-1-yl]butanamide | 303 | >64.0 | >64.0 | >64.0 | >64.0 |
| 32 | 4-(4-{[(2-ethylphenyl)sulfanyl]methyl}-1H-1,2,3-triazol-1-yl)-N-hydroxy-2-methyl-2-(methylsulfonyl)butanamide | 50.9 | >64.0 | >64.0 | >64.0 | >64.0 |
| 33 | N-hydroxy-2-methyl-2-(methylsulfonyl)-4-(4-{[4-(trifluoromethyl)phenoxy]methyl}-1H-1,2,3-triazol-1-yl)butanamide | 9.6 | >64.0 | 64 | >64.0 | 32 |
| 34 | N-hydroxy-2-methyl-2-(methylsulfonyl)-4-{4-[(naphthalen-1-yloxy)methyl]-1H-1,2,3-triazol-1-yl}butanamide | 26.3 | >64.0 | >64.0 | >64.0 | >64.0 |
| 35 | 4-{4-[(3-te-butylphenoxy)methyl]-1H-1,2,3-triazol-1-yl}-N-hydroxy-2-methyl-2-(methylsulfonyl)butanamide | 24 | >64.0 | >64.0 | >64.0 | >64.0 |
| 36 | N-hydroxy-2-methyl-4-(4-{[3-(methylsulfanyl)phenoxy]methyl}-1H-1,2,3-triazol-1-yl)-2-(methylsulfonyl)butanamide | 6.39 | >64.0 | >64.0 | >64.0 | 32 |
| 37 | N-hydroxy-2-methyl-4-[4-(4-methylphenyl)-1H-1,2,3-triazol-1-yl]-2-(methylsulfonyl)butanamide | 1.39 | >64.0 | 16 | 64 | 4 |
| 38 | 4-[4-(2-bromophenyl)-1H-1,2,3-triazol-1-yl]-N-hydroxy-2-methyl-2-(methylsulfonyl)butanamide | 18.9 | >64.0 | 16 | >64.0 | 32 |
| 39 | 4-{4-[(2,5-dimethylphenoxy)methyl]-1H-1,2,3-triazol-1-yl}-N-hydroxy-2-methyl-2-(methylsulfonyl)butanamide | 51.3 | >64.0 | >64.0 | >64.0 | >64.0 |
| 40 | N-hydroxy-2-methyl-2-(methylsulfonyl)-4-(4-phenyl-1H-pyrazol-1-yl)butanamide | 4.63 | >64.0 | 32 | >64.0 | 2 |
| 41 | N-hydroxy-2-methyl-4-[4-(4-methylphenyl)-1H-pyrazol-1-yl]-2-(methylsulfonyl)butanamide | 1.26 | >64.0 | 8 | 64 | 2 |
| 42 | N-hydroxy-2-methyl-4-[4-(3-methylphenyl)-1H-pyrazol-1-yl]-2-(methylsulfonyl)butanamide | 6.2 | >64.0 | 64 | >64.0 | 4 |
| 43 | N-hydroxy-2-methyl-4-[4-(2-methylphenyl)-1H-pyrazol-1-yl]-2-(methylsulfonyl)butanamide | 11.3 | >64.0 | 32 | >64.0 | 16 |
| 44 | N-hydroxy-4-[4-(3-hydroxyphenyl)-1H-pyrazol-1-yl]-2-methyl-2-(methylsulfonyl)butanamide | 21.1 | >64.0 | >64.0 | >64.0 | >64.0 |
| 45 | 4-[4-(2-fluorophenyl)-1H-pyrazol-1-yl]-N-hydroxy-2-methyl-2-(methylsulfonyl)butanamide | 2.5 | >64.0 | 16 | 64 | 2 |
| 46 | 4-[4-(2-cyanophenyl)-1H-pyrazol-1-yl]-N-hydroxy-2-methyl-2-(methylsulfonyl)butanamide | 72.5 | >64.0 | 4 | >64.0 | 32 |
| 47 | 4-[4-(4-cyanophenyl)-1H-pyrazol-1-yl]-N-hydroxy-2-methyl-2-(methylsulfonyl)butanamide | 1.15 | >64.0 | 64 | >64.0 | 4 |
| 48 | 4-[4-(3-cyanophenyl)-1H-pyrazol-1-yl]-N-hydroxy-2-methyl-2-(methylsulfonyl)butanamide | 29.3 | >64.0 | >64.0 | >64.0 | 64 |

TABLE 5-continued

Biological Data

| Ex. No. | Compound Name | PA: IC$_{50}$ (nM) | AB-3167 (µg/ml) | EC-1 (µg/ml) | KP-3700 (µg/ml) | PA-7 (µg/ml) |
|---|---|---|---|---|---|---|
| 49 | N-hydroxy-4-[4-(4-hydroxy-2-methylphenyl)-1H-pyrazol-1-yl]-2-methyl-2-(methylsulfonyl)butanamide | 90.4 | >64.0 | >64.0 | >64.0 | >64.0 |
| 50 | N-hydroxy-4-[4-(4-hydroxy-3-methylphenyl)-1H-pyrazol-1-yl]-2-methyl-2-(methylsulfonyl)butanamide | 44.4 | >64.0 | >64.0 | >64.0 | >64.0 |
| 51 | N-hydroxy-4-[4-(3-methoxyphenyl)-1H-pyrazol-1-yl]-2-methyl-2-(methylsulfonyl)butanamide | 7.3 | >64.0 | >64.0 | >64.0 | 16 |
| 52 | 4-[4-(4-fluoro-3-methylphenyl)-1H-pyrazol-1-yl]-N-hydroxy-2-methyl-2-(methylsulfonyl)butanamide | 6.93 | >64.0 | 16 | 64 | 2 |
| 53 | 4-[4-(3-fluoro-2-methylphenyl)-1H-pyrazol-1-yl]-N-hydroxy-2-methyl-2-(methylsulfonyl)butanamide | 9.28 | >64.0 | 32 | >64.0 | 16 |
| 54 | 4-[4-(5-chloropyridin-2-yl)-1H-pyrazol-1-yl]-N-hydroxy-2-methyl-2-(methylsulfonyl)butanamide | 6.94 | >64.0 | >64.0 | >64.0 | 16 |
| 55 | 4-[4-(2,4-difluorophenyl)-1H-pyrazol-1-yl]-N-hydroxy-2-methyl-2-(methylsulfonyl)butanamide | 2.07 | >64.0 | 8 | 64 | 2 |
| 56 | 4-[4-(2,5-difluorophenyl)-1H-pyrazol-1-yl]-N-hydroxy-2-methyl-2-(methylsulfonyl)butanamide | 6.75 | >64.0 | 32 | >64.0 | 8 |
| 57 | N-hydroxy-2-methyl-2-(methylsulfonyl)-4-[4-(1H-pyrrolo[2,3-b]pyridin-6-yl)-1H-pyrazol-1-yl]butanamide | 3.72 | >64.0 | >64.0 | >64.0 | 64 |
| 58 | 4-[4-(2,3-dihydro-1-benzofuran-5-yl)-1H-pyrazol-1-yl]-N-hydroxy-2-methyl-2-(methylsulfonyl)butanamide | 1.17 | >64.0 | >64.0 | >64.0 | 4 |
| 59 | 4-[4-(3-cyano-4-fluorophenyl)-1H-pyrazol-1-yl]-N-hydroxy-2-methyl-2-(methylsulfonyl)butanamide | 11.6 | >64.0 | >64.0 | >64.0 | 64 |
| 60 | 4-[4-(3-fluoro-4-methoxyphenyl)-1H-pyrazol-1-yl]-N-hydroxy-2-methyl-2-(methylsulfonyl)butanamide | 20.1 | >64.0 | 64 | >64.0 | 8 |
| 61 | N-hydroxy-2-methyl-2-(methylsulfonyl)-4-[4-(3-oxo-2,3-dihydro-1H-inden-5-yl)-1H-pyrazol-1-yl]butanamide | 38.6 | >64.0 | >64.0 | >64.0 | >64.0 |
| 62 | N-hydroxy-2-methyl-2-(methylsulfonyl)-4-[4-(1-oxo-2,3-dihydro-1H-inden-5-yl)-1H-pyrazol-1-yl]butanamide | 0.754 | >64.0 | >64.0 | >64.0 | 16 |
| 63 | 4-[4-(2,3-dihydro-1,4-benzodioxin-6-yl)-1H-pyrazol-1-yl]-N-hydroxy-2-methyl-2-(methylsulfonyl)butanamide | 6.75 | >64.0 | >64.0 | >64.0 | 4 |
| 64 | 4-[4-(3-chloro-4-cyanophenyl)-1H-pyrazol-1-yl]-N-hydroxy-2-methyl-2-(methylsulfonyl)butanamide | 0.62 | >64.0 | 64 | >64.0 | 4 |
| 65 | 4-[4-(3,4-dimethoxyphenyl)-1H-pyrazol-1-yl]-N-hydroxy-2-methyl-2-(methylsulfonyl)butanamide | 93.2 | >64.0 | >64.0 | >64.0 | >64.0 |
| 66 | 4-{4-[4-(1-cyanocyclopropyl)phenyl]-1H-pyrazol-1-yl}-N-hydroxy-2-methyl-2-(methylsulfonyl)butanamide | 2.83 | >64.0 | >64.0 | >64.0 | 16 |
| 67 | N-hydroxy-2-methyl-4-[4-(2-methylquinolin-6-yl)-1H-pyrazol-1-yl]-2-(methylsulfonyl)butanamide | 12.1 | >64.0 | >64.0 | >64.0 | 32 |
| 68 | 4-{4-[3-(difluoromethoxy)phenyl]-1H-pyrazol-1-yl}-N-hydroxy-2-methyl-2-(methylsulfonyl)butanamide | 2.1 | >64.0 | 64 | >64.0 | 8 |
| 69 | 4-[4-(3-aminoisoquinolin-6-yl)-1H-pyrazol-1-yl]-N-hydroxy-2-methyl-2-(methylsulfonyl)butanamide | 2.57 | >64.0 | >64.0 | >64.0 | >64.0 |
| 70 | N-hydroxy-2-methyl-2-(methylsulfonyl)-4-{4-[4-(1H-pyrazol-3-yl)phenyl]-1H-pyrazol-1-yl}butanamide | 4.11 | >64.0 | 64 | >64.0 | 32 |
| 71 | N-hydroxy-2-methyl-2-(methylsulfonyl)-4-{4-[3-(1H-pyrazol-3-yl)phenyl]-1H-pyrazol-1-yl}butanamide | 5.12 | >64.0 | >64.0 | >64.0 | >64.0 |

TABLE 5-continued

Biological Data

| Ex. No. | Compound Name | PA: IC$_{50}$ (nM) | AB-3167 (μg/ml) | EC-1 (μg/ml) | KP-3700 (μg/ml) | PA-7 (μg/ml) |
|---|---|---|---|---|---|---|
| 72 | N-hydroxy-2-methyl-2-(methylsulfonyl)-4-{4-[4-(1,3-oxazol-5-yl)phenyl]-1H-pyrazol-1-yl}butanamide | 0.373 | >64.0 | 4 | 16 | 2 |
| 73 | N-hydroxy-2-methyl-2-(methylsulfonyl)-4-{4-[4-(1,2-oxazol-5-yl)phenyl]-1H-pyrazol-1-yl}butanamide | 0.35 | >64.0 | 4 | 16 | 2 |
| 74 | N-hydroxy-2-methyl-2-(methylsulfonyl)-4-{4-[3-(1,2-oxazol-5-yl)phenyl]-1H-pyrazol-1-yl}butanamide | 2.45 | >64.0 | >64.0 | >64.0 | 32 |
| 75 | N-hydroxy-2-methyl-2-(methylsulfonyl)-4-[4-(8-oxo-5,6,7,8-tetrahydronaphthalen-2-yl)-1H-pyrazol-1-yl]butanamide | 7.17 | >64.0 | >64.0 | >64.0 | 64 |
| 76 | N-hydroxy-2-methyl-2-(methylsulfonyl)-4-{4-[5-(trifluoromethyl)pyridin-2-yl]-1H-pyrazol-1-yl}butanamide | 37.3 | >64.0 | >64.0 | >64.0 | 64 |
| 77 | N-hydroxy-2-methyl-2-(methylsulfonyl)-4-{4-[6-(trifluoromethyl)pyridin-3-yl]-1H-pyrazol-1-yl}butanamide | 19.5 | >64.0 | >64.0 | >64.0 | 64 |
| 78 | 4-[4-(3-cyano-4-ethoxyphenyl)-1H-pyrazol-1-yl]-N-hydroxy-2-methyl-2-(methylsulfonyl)butanamide | 21.7 | >64.0 | >64.0 | >64.0 | 64 |
| 79 | N-hydroxy-2-methyl-4-[4-(2-methyl-1,3-benzothiazol-6-yl)-1H-pyrazol-1-yl]-2-(methylsulfonyl)butanamide | 6.22 | >64.0 | 64 | >64.0 | 16 |
| 80 | 4-[4-(2-amino-1,3-benzothiazol-6-yl)-1H-pyrazol-1-yl]-N-hydroxy-2-methyl-2-(methylsulfonyl)butanamide | 75.8 | >64.0 | >64.0 | >64.0 | >64.0 |
| 81 | N-hydroxy-2-methyl-4-{4-[6-(2-methylpropoxy)pyridin-3-yl]-1H-pyrazol-1-yl}-2-(methylsulfonyl)butanamide | 2.07 | >64.0 | 8 | 32 | 32 |
| 82 | N-hydroxy-2-methyl-4-{4-[4-(1-methyl-1H-pyrazol-5-yl)phenyl]-1H-pyrazol-1-yl}-2-(methylsulfonyl)butanamide | 3.29 | >64.0 | 8 | 32 | 16 |
| 83 | 4-[4-(1-benzyl-1H-imidazol-4-yl)-1H-pyrazol-1-yl]-N-hydroxy-2-methyl-2-(methylsulfonyl)butanamide | >100 | | | | |
| 84 | N-hydroxy-2-methyl-4-{4-[4-(3-methyl-1H-pyrazol-5-yl)phenyl]-1H-pyrazol-1-yl}-2-(methylsulfonyl)butanamide | 6.44 | >64.0 | 16 | >64.0 | 64 |
| 85 | 4-{4-[3-(5-amino-1H-pyrazol-3-yl)phenyl]-1H-pyrazol-1-yl}-N-hydroxy-2-methyl-2-(methylsulfonyl)butanamide | 58.9 | >64.0 | >64.0 | >64.0 | >64.0 |
| 86 | 6-{1-[4-(hydroxyamino)-3-methyl-3-(methylsulfonyl)-4-oxobutyl]-1H-pyrazol-4-yl}-1H-indole-2-carboxamide | 14.5 | >64.0 | >64.0 | >64.0 | >64.0 |
| 87 | 5-{1-[4-(hydroxyamino)-3-methyl-3-(methylsulfonyl)-4-oxobutyl]-1H-pyrazol-4-yl}-1H-indole-2-carboxamide | 63.6 | >64.0 | >64.0 | >64.0 | >64.0 |
| 88 | N-hydroxy-2-methyl-2-(methylsulfonyl)-4-{4-[3-(trifluoromethoxy)phenyl]-1H-pyrazol-1-yl}butanamide | 0.652 | 64 | 32 | >64.0 | 8 |
| 89 | 4-{4-[1-(4-fluorophenyl)-1H-imidazol-4-yl]-1H-pyrazol-1-yl}-N-hydroxy-2-methyl-2-(methylsulfonyl)butanamide | >100 | | | | |
| 90 | N-hydroxy-2-methyl-2-(methylsulfonyl)-4-{4-[4-(1,2,3-thiadiazol-4-yl)phenyl]-1H-pyrazol-1-yl}butanamide | 1.23 | >64.0 | 16 | 64 | 4 |
| 91 | 4-[4-(2-ethyl-1,3-benzothiazol-6-yl)-1H-pyrazol-1-yl]-N-hydroxy-2-methyl-2-(methylsulfonyl)butanamide | 2.55 | >64.0 | 32 | >64.0 | 16 |
| 92 | N-hydroxy-2-methyl-4-{4-[4-(2-methylpyrimidin-4-yl)phenyl]-1H-pyrazol-1-yl}-2-(methylsulfonyl)butanamide | 5.49 | >64.0 | 32 | >64.0 | 32 |

We claim:
1. A compound of Formula I

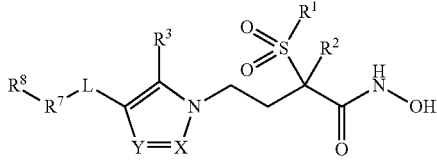

Formula I or a pharmaceutically acceptable salt thereof;
wherein
$R^1$ is $(C_1-C_3)$alkyl;
$R^2$ is hydrogen or $(C_1-C_3)$alkyl;
$R^3$ is hydrogen or $(C_1-C_3)$alkyl;
X is N or $CR^4$;
Y is N or $CR^4$;
$R^4$ is hydrogen or $(C_1-C_3)$alkyl;
L is a bond, $(C_2-C_6)$alkenylene, $(C_1-C_6)$alkylene, $(C_2-C_6)$alkynylene, —$(CH_2)_nO(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$—, or —$(CH_2)_nNR^5CO(CH_2)_p$—;
$R^5$ and $R^6$ are independently hydrogen, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl, or formyl;
n is 0, 1, 2, 3, or 4;
p is 0, 1, 2, 3, or 4;
$R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_3-C_8)$cycloalkyl-$NR^5$—, $(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocycle, $(C_3-C_{13})$heterocycleoxy, $(C_3-C_{13})$heterocyclethio, $(C_3-C_{13})$heterocycle-$NR^5$—, hydroxy$(C_1-C_{10})$alkyl, mercapto$(C_1-C_6)$alkyl, $(NR^5R^6)$alkyl, or $(NR^5R^6)$carbonyl; and
$R^8$ is absent, $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocycle, or $(C_3-C_{13})$heterocycle$(C_1-C_6)$alkyl.

2. The compound according to claim 1, or a pharmaceutically acceptable salt thereof;
wherein:
$R^1$ is $(C_1-C_3)$alkyl;
$R^2$ is $(C_1-C_3)$alkyl;
$R^3$ is hydrogen or $(C_1-C_3)$alkyl;
X is N;
Y is N or $CR^4$;
$R^4$ is hydrogen or $(C_1-C_3)$alkyl;
L is a bond, $(C_2-C_6)$alkynylene, —$(CH_2)_nO(CH_2)_p$—, or —$(CH_2)_nS(CH_2)_p$—;
n is 0, 1, or 2;
p is 0, 1, or 2;
$R^7$ is $(C_1-C_6)$alkyl, $(C_6-C_{12})$aryl, cyano, $(C_5-C_8)$cycloalkenyl, $(C_3-C_8)$cycloalkyl, $(C_5-C_{12})$heteroaryl, or $(C_3-C_{13})$heterocycle; and
$R^8$ is absent, $(C_6-C_{12})$aryl, $(C_6-C_{12})$aryl$(C_1-C_6)$alkyl, $(C_3-C_8)$cycloalkyl, or $(C_5-C_{12})$heteroaryl.

3. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond, $(C_2-C_6)$alkynylene, —$(CH_2)_nO(CH_2)_p$—, or —$(CH_2)_nS(CH_2)_p$—;
n is 0, 1, or 2;
p is 0, 1, or 2;
$R^7$ is $(C_6-C_{12})$aryl, wherein the $(C_6-C_{12})$aryl is dihydroindenyl, naphthyl, phenyl, or tetrahydronaphthalenyl, wherein each is optionally substituted with 1, 2, or 3 substituents that are independently $(C_1-C_6)$alkoxy, $(C_1-C_6)$alkyl, $(C_1-C_6)$alkylthio, cyano, ethylenedioxy, halo$(C_1-C_6)$alkoxy, halo$(C_1-C_6)$alkyl, halogen, hydroxy, or oxo; and
$R^8$ is absent, $(C_3-C_8)$cycloalkyl, or $(C_5-C_{12})$heteroaryl.

4. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond, —C≡C—, —O(CH_2)—, or —S(CH_2)—;
$R^7$ is $(C_6-C_{12})$aryl, wherein the $(C_6-C_{12})$aryl is dihydroindenyl, naphthyl, phenyl, or tetrahydronaphthalenyl, wherein each is optionally substituted with 1, 2, or 3 substituents that are independently $(C_1-C_6)$alkoxy, $(C_1-C_6)$alkyl, $(C_1-C_6)$alkylthio, cyano, ethylenedioxy, halo$(C_1-C_6)$alkoxy, halo$(C_1-C_6)$alkyl, halogen, hydroxy, or oxo; and
$R^8$ is absent, $(C_3-C_8)$cycloalkyl, or $(C_5-C_{12})$heteroaryl wherein the $(C_5-C_{12})$heteroaryl is isoxazolyl, oxazolyl, pyrazolyl, pryimidinyl, or thiadiazoyl wherein each is optionally substituted with 1 substituent that is $(C_1-C_6)$alkyl or $NZ^1Z^2$ wherein $Z^1$ and $Z^2$ are hydrogen, and wherein the $(C_3-C_8)$cycloalkyl is cyclopropyl optionally substituted with 1 substituent that is cyano.

5. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond;
$R^7$ is $(C_5-C_8)$cycloalkenyl or $(C_3-C_8)$cycloalkyl, wherein the $(C_5-C_8)$cycloalkenyl is cyclohexenyl, and wherein the $(C_3-C_8)$cycloalkyl is cyclohexyl or cyclopentyl; and
$R^8$ is absent.

6. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond, $(C_2-C_6)$alkynylene, $—(CH_2)_nO(CH_2)_p—$, or $—(CH_2)_nS(CH_2)_p—$;
n is 0, 1, or 2;
p is 0, 1, or 2;
$R^7$ is $(C_5-C_{12})$heteroaryl wherein the $(C_5-C_{12})$heteroaryl is benzoxazolyl, benzothiazolyl, indolyl, imidazolyl, isoquinolinyl, oxazolyl, pyrazinyl, pyrazolyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, $—NZ^1Z^2$, or $(NZ^1Z^2)$carbonyl where $Z^1$ and $Z^2$ are hydrogen; and
$R^8$ is absent, $(C_6-C_{12})$aryl, or $(C_6-C_{12})$aryl$(C_1-C_6)$alkyl.

7. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond;
$R^7$ is $(C_5-C_{12})$heteroaryl wherein the $(C_5-C_{12})$heteroaryl is benzoxazolyl, benzothiazolyl, indolyl, imidazolyl, isoquinolinyl, oxazolyl, pyrazinyl, pyrazolyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, $—NZ^1Z^2$, or $(NZ^1Z^2)$carbonyl where $Z^1$ and $Z^2$ are hydrogen; and
$R^8$ is absent, $(C_6-C_{12})$aryl, or $(C_6-C_{12})$aryl$(C_1-C_6)$alkyl, wherein the $(C_6-C_{12})$aryl$(C_1-C_6)$alkyl is benzyl and wherein the $(C_6-C_{12})$aryl is phenyl optionally substituted with 1 substituent that is halogen.

8. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond;
$R^7$ is $(C_3-C_{13})$heterocycle wherein the $(C_3-C_{13})$heterocycle is 2,3-dihydrobenzofuranyl; and
$R^8$ is absent.

9. The compound according to claim 1, or a pharmaceutically acceptable salt thereof;
wherein:
$R^1$ is methyl;
$R^2$ is methyl;
$R^3$ is hydrogen or methyl;
X is N;
Y is N or $CR^4$;
$R^4$ is hydrogen or methyl;
L is a bond;
$R^7$ is $(C_1-C_6)$alkyl or cyano; and
$R^8$ is absent.

10. The compound according to claim 1, or a pharmaceutically acceptable salt thereof;
wherein
X is N; and
Y is N.

11. The compound according to claim 10, or a pharmaceutically acceptable salt thereof;
wherein
$R^1$ is $(C_1-C_3)$alkyl;
$R^2$ is hydrogen or $(C_1-C_3)$alkyl;
$R^3$ is hydrogen or $(C_1-C_3)$alkyl;
L is a bond, $—(CH_2)_nO(CH_2)_p—$, or $—(CH_2)_nS(CH_2)_p—$;
n is 0, 1, or 2;
p is 0, 1, or 2;
$R^7$ is $(C_6-C_{12})$aryl; and
$R^8$ is absent.

12. The compound according to claim 10, or a pharmaceutically acceptable salt thereof;
wherein
$R^1$ is methyl;
$R^2$ is methyl;
$R^3$ is hydrogen or methyl;
L is a bond, $—O(CH_2)—$, or $—S(CH_2)—$;
$R^7$ is $(C_6-C_{12})$aryl wherein the $(C_6-C_{12})$aryl is naphthyl or phenyl where each is optionally substituted with 1, 2, or 3 substituents that are independently $(C_1-C_6)$alkoxy, $(C_1-C_6)$alkyl, $(C_1-C_6)$alkylthio, halo$(C_1-C_6)$alkyl, or halogen; and
$R^8$ is absent.

13. The compound according to claim 10 that is
(2R)—N-hydroxy-2-methyl-2-(methylsulfonyl)-4-(4-phenyl-1H-1,2,3-triazol-1-yl)butanamide;
(2R)—N-hydroxy-2-methyl-4-(5-methyl-4-phenyl-1H-1,2,3-triazol-1-yl)-2-(methylsulfonyl)butanamide;
(2R)-4-[4-(2-chloro-4-methoxyphenyl)-1H-1,2,3-triazol-1-yl]-N-hydroxy-2-methyl-2-(methylsulfonyl)butanamide;
(2R)-4-[4-(2,3-difluorophenyl)-1H-1,2,3-triazol-1-yl]-N-hydroxy-2-methyl-2-(methylsulfonyl)butanamide;
(2R)—N-hydroxy-2-methyl-2-(methylsulfonyl)-4-[4-(2,3,4-trifluorophenyl)-1H-1,2,3-triazol-1-yl]butanamide;
(2R)-4-[4-(2,3-dichlorophenyl)-1H-1,2,3-triazol-1-yl]-N-hydroxy-2-methyl-2-(methylsulfonyl)butanamide;
(2R)-4-[4-(3,4-difluorophenyl)-1H-1,2,3-triazol-1-yl]-N-hydroxy-2-methyl-2-(methylsulfonyl)butanamide;
(2R)-4-[4-(3,4-dichlorophenyl)-1H-1,2,3-triazol-1-yl]-N-hydroxy-2-methyl-2-(methylsulfonyl)butanamide;
(2R)-4-[4-(2-fluoro-4-methoxyphenyl)-1H-1,2,3-triazol-1-yl]-N-hydroxy-2-methyl-2-(methylsulfonyl)butanamide;
(2R)-4-[4-(4-chloro-3-fluorophenyl)-1H-1,2,3-triazol-1-yl]-N-hydroxy-2-methyl-2-(methylsulfonyl)butanamide;
(2R)-4-[4-(4-chloro-2-fluorophenyl)-1H-1,2,3-triazol-1-yl]-N-hydroxy-2-methyl-2-(methylsulfonyl)butanamide;
4-(4-{[(4-bromophenyl)sulfanyl]methyl}-1H-1,2,3-triazol-1-yl)-N-hydroxy-2-methyl-2-(methylsulfonyl)butanamide;
4-[4-(4-chlorophenyl)-1H-1,2,3-triazol-1-yl]-N-hydroxy-2-methyl-2-(methylsulfonyl)butanamide;
4-(4-{[(3-chlorophenyl)sulfanyl]methyl}-1H-1,2,3-triazol-1-yl)-N-hydroxy-2-methyl-2-(methylsulfonyl)butanamide;

4-(4-{[(2-t-butylphenyl)sulfanyl]methyl}-1H-1,2,3-triazol-1-yl)-N-hydroxy-2-methyl-2-(methylsulfonyl)butanamide;

4-(4-{[(4-chlorophenyl)sulfanyl]methyl}-1H-1,2,3-triazol-1-yl)-N-hydroxy-2-methyl-2-(methylsulfonyl)butanamide;

N-hydroxy-2-methyl-2-(methylsulfonyl)-4-{4-[(naphthalen-2-yloxy)methyl]-1H-1,2,3-triazol-1-yl}butanamide;

N-hydroxy-2-methyl-2-(methylsulfonyl)-4-[4-({[2-(propan-2-yl)phenyl]sulfanyl}methyl)-1H-1,2,3-triazol-1-yl]butanamide;

4-(4-{[(2-ethylphenyl)sulfanyl]methyl}-1H-1,2,3-triazol-1-yl)-N-hydroxy-2-methyl-2-(methylsulfonyl)butanamide;

N-hydroxy-2-methyl-2-(methylsulfonyl)-4-(4-{[4-(trifluoromethyl)phenoxy]methyl}-1H-1,2,3-triazol-1-yl)butanamide;

N-hydroxy-2-methyl-2-(methylsulfonyl)-4-{4-[(naphthalen-1-yloxy)methyl]-1H-1,2,3-triazol-1-yl}butanamide;

4-{4-[(3-t-butylphenoxy)methyl]-1H-1,2,3-triazol-1-yl}-N-hydroxy-2-methyl-2-(methylsulfonyl)butanamide;

N-hydroxy-2-methyl-4-(4-{[3-(methylsulfanyl)phenoxy]methyl}-1H-1,2,3-triazol-1-yl)-2-(methylsulfonyl)butanamide;

N-hydroxy-2-methyl-4-[4-(4-methylphenyl)-1H-1,2,3-triazol-1-yl]-2-(methylsulfonyl)butanamide;

4-[4-(2-bromophenyl)-1H-1,2,3-triazol-1-yl]-N-hydroxy-2-methyl-2-(methylsulfonyl)butanamide;

4-{4-[(2,5-dimethylphenoxy)methyl]-1H-1,2,3-triazol-1-yl}-N-hydroxy-2-methyl-2-(methylsulfonyl)butanamide;

or a pharmaceutically acceptable salt thereof.

14. The compound according to claim 1, or a pharmaceutically acceptable salt thereof;
wherein
X is N; and
Y is $CR^4$.

15. The compound according to claim 14, or a pharmaceutically acceptable salt thereof;
wherein
$R^1$ is $(C_1-C_3)$alkyl;
$R^2$ is $(C_1-C_3)$alkyl;
$R^3$ is hydrogen;
$R^4$ is hydrogen or $(C_1-C_3)$alkyl;
L is a bond or $(C_2-C_6)$alkynylene;
$R^7$ is $(C_1-C_6)$alkyl, $(C_6-C_{12})$aryl, cyano, $(C_5-C_8)$cycloalkenyl, $(C_3-C_8)$cycloalkyl, $(C_5-C_{12})$heteroaryl, or $(C_3-C_{13})$heterocycle; and
$R^8$ is absent, $(C_6-C_{12})$aryl, $(C_6-C_{12})$aryl$(C_1-C_6)$alkyl, $(C_3-C_8)$cycloalkyl, or $(C_5-C_{12})$heteroaryl.

16. The compound according to claim 14, or a pharmaceutically acceptable salt thereof;
wherein
$R^1$ is methyl;
$R^2$ is methyl;
$R^3$ is hydrogen;
$R^4$ is hydrogen or methyl;
L is a bond or —C≡C—;
$R^7$ is $(C_6-C_{12})$aryl wherein the $(C_6-C_{12})$aryl is dihydroindenyl, phenyl, or tetrahydronaphthalenyl wherein each is optionally substituted with 1, 2, or 3 substituents that are independently $(C_1-C_6)$alkoxy, $(C_1-C_6)$alkyl, cyano, ethylenedioxy, halo$(C_1-C_8)$alkoxy, halogen, hydroxy, or oxo; and
$R^8$ is absent, $(C_3-C_8)$cycloalkyl, or $(C_5-C_{12})$heteroaryl.

17. The compound according to claim 14, or a pharmaceutically acceptable salt thereof;
wherein
$R^1$ is methyl;
$R^2$ is methyl;
$R^3$ is hydrogen;
$R^4$ is hydrogen or methyl;
L is a bond or —C≡C—;
$R^7$ is $(C_6-C_{12})$aryl wherein the $(C_6-C_{12})$aryl is dihydroindenyl, phenyl, or tetrahydronaphthalenyl wherein each is optionally substituted with 1, 2, or 3 substituents that are independently $(C_1-C_6)$alkoxy, $(C_1-C_6)$alkyl, cyano, ethylenedioxy, halo$(C_1-C_8)$alkoxy, halogen, hydroxy, or oxo; and
$R^8$ is absent, $(C_3-C_8)$cycloalkyl, or $(C_5-C_{12})$heteroaryl, wherein the $(C_3-C_8)$cycloalkyl is cyclopropyl optionally substituted with cyano, and wherein the $(C_5-C_{12})$heteroaryl is isoxazolyl, oxazolyl, pyrazolyl, pyrimidinyl, or thiadiazolyl wherein each is optionally substituted with 1 substituent that is $(C_1-C_6)$alkyl or $NZ^1Z^2$ wherein $Z^1$ and $Z^2$ are hydrogen.

18. The compound according to claim 14, or a pharmaceutically acceptable salt thereof;
wherein
$R^1$ is methyl;
$R^2$ is methyl;
$R^3$ is hydrogen;
$R^4$ is hydrogen;
L is a bond;
$R^7$ is $(C_5-C_{12})$heteroaryl wherein the $(C_5-C_{12})$heteroaryl is benzoxazolyl, benzothiazolyl, imidazolyl, indolyl, isoquinolinyl, pyrazinyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl wherein $Z^1$ and $Z^2$ are hydrogen; and
$R^8$ is absent, $(C_6-C_{12})$aryl, or $(C_6-C_{12})$aryl$(C_1-C_6)$alkyl.

19. The compound according to claim 14, or a pharmaceutically acceptable salt thereof;
wherein
$R^1$ is methyl;
$R^2$ is methyl;
$R^3$ is hydrogen;
$R^4$ is hydrogen;
L is a bond;
$R^7$ is $(C_5-C_{12})$heteroaryl wherein the $(C_5-C_{12})$heteroaryl is benzoxazolyl, benzothiazolyl, imidazolyl, indolyl, isoquinolinyl, pyrazinyl, pyridinyl, pyrrolopyridinyl, quinolinyl, or quinoxalinyl, wherein each is optionally substituted with 1 substituent that is $(C_1-C_6)$alkoxy, $(C_1-C_6)$alkyl, halo$(C_1-C_6)$alkyl, halogen, —$NZ^1Z^2$, or $(NZ^1Z^2)$carbonyl wherein $Z^1$ and $Z^2$ are hydrogen; and
$R^8$ is absent, $(C_6-C_{12})$aryl, or $(C_6-C_{12})$aryl$(C_1-C_6)$alkyl, wherein the $(C_6-C_{12})$aryl$(C_1-C_6)$alkyl is benzyl, and wherein the $(C_6-C_{12})$aryl is phenyl optionally substituted with 1 substituent that is halogen.

20. The compound according to claim 14, or a pharmaceutically acceptable salt thereof;
wherein
$R^1$ is methyl;
$R^2$ is methyl;
$R^3$ is hydrogen;
$R^4$ is hydrogen;
L is a bond;
$R^7$ is $(C_1-C_6)$alkyl or cyano; and
$R^8$ is absent.

21. The compound according to claim 14, or a pharmaceutically acceptable salt thereof;
wherein
R¹ is methyl;
R² is methyl;
R³ is hydrogen;
R⁴ is hydrogen;
L is a bond;
R⁷ is (C₅-C₈)cycloalkenyl or (C₃-C₈)cycloalkyl, wherein the (C₅-C₈)cycloalkenyl is cyclohexenyl, and wherein the (C₃-C₈)cycloalkyl is cyclohexyl or cyclopentyl; and
R⁸ is absent.

22. The compound according to claim 14, or a pharmaceutically acceptable salt thereof;
wherein
R¹ is methyl;
R² is methyl;
R³ is hydrogen;
R⁴ is hydrogen;
L is a bond;
R⁷ is (C₃-C₁₃)heterocycle wherein (C₃-C₁₃)heterocycle is 2,3-dihydrobenzofuranyl; and
R⁸ is absent.

23. The compound according to claim 14 that is
(2R)-4-[4-(cyclohex-1-en-1-yl)-1H-pyrazol-1-yl]-N-hydroxy-2-methyl-2-(methylsulfonyl)butanamide;
(2R)-4-(4-cyclohexyl-1H-pyrazol-1-yl)-N-hydroxy-2-methyl-2-(methylsulfonyl)butanamide;
(2R)-4-(4-cyclopentyl-1H-pyrazol-1-yl)-N-hydroxy-2-methyl-2-(methylsulfonyl)butanamide;
(2R)—N-hydroxy-2-methyl-4-(3-methyl-4-phenyl-1H-pyrazol-1-yl)-2-(methylsulfonyl)butanamide;
(2R)—N-hydroxy-2-methyl-4-(4-methyl-1H-pyrazol-1-yl)-2-(methylsulfonyl)butanamide;
(2R)—N-hydroxy-2-methyl-2-(methylsulfonyl)-4-(4-phenyl-1H-pyrazol-1-yl)butanamide;
(2R)-4-(4-cyano-1H-pyrazol-1-yl)-N-hydroxy-2-methyl-2-(methylsulfonyl)butanamide;
(2R)—N-hydroxy-2-methyl-2-(methylsulfonyl)-4-[4-(pyrazin-2-yl)-1H-pyrazol-1-yl]butanamide;
(2R)—N-hydroxy-2-methyl-2-(methylsulfonyl)-4-[4-(quinoxalin-2-yl)-1H-pyrazol-1-yl]butanamide;
(2R)-4-[4-(1,3-benzoxazol-2-yl)-1H-pyrazol-1-yl]-N-hydroxy-2-methyl-2-(methylsulfonyl)butanamide;
(2R)-4-{4-[(3-cyanophenyl)ethynyl]-1H-pyrazol-1-yl}-N-hydroxy-2-methyl-2-(methylsulfonyl)butanamide;
(2R)—N-hydroxy-2-methyl-2-(methylsulfonyl)-4-{4-[4-(1,3-oxazol-2-yl)phenyl]-1 H-pyrazol-1-yl}butanamide
N-hydroxy-2-methyl-2-(methylsulfonyl)-4-(4-phenyl-1H-pyrazol-1-yl)butanamide;
N-hydroxy-2-methyl-4-[4-(4-methylphenyl)-1H-pyrazol-1-yl]-2-(methylsulfonyl)butanamide;
N-hydroxy-2-methyl-4-[4-(3-methylphenyl)-1H-pyrazol-1-yl]-2-(methylsulfonyl)butanamide;
N-hydroxy-2-methyl-4-[4-(2-methylphenyl)-1H-pyrazol-1-yl]-2-(methylsulfonyl)butanamide;
N-hydroxy-4-[4-(3-hydroxyphenyl)-1H-pyrazol-1-yl]-2-methyl-2-(methylsulfonyl)butanamide;
4-[4-(2-fluorophenyl)-1H-pyrazol-1-yl]-N-hydroxy-2-methyl-2-(methylsulfonyl)butanamide;
4-[4-(2-cyanophenyl)-1H-pyrazol-1-yl]-N-hydroxy-2-methyl-2-(methylsulfonyl)butanamide;
4-[4-(4-cyanophenyl)-1H-pyrazol-1-yl]-N-hydroxy-2-methyl-2-(methylsulfonyl)butanamide;
4-[4-(3-cyanophenyl)-1H-pyrazol-1-yl]-N-hydroxy-2-methyl-2-(methylsulfonyl)butanamide;
N-hydroxy-4-[4-(4-hydroxy-2-methylphenyl)-1H-pyrazol-1-yl]-2-methyl-2-(methylsulfonyl)butanamide;
N-hydroxy-4-[4-(4-hydroxy-3-methylphenyl)-1H-pyrazol-1-yl]-2-methyl-2-(methylsulfonyl)butanamide;
N-hydroxy-4-[4-(3-methoxyphenyl)-1H-pyrazol-1-yl]-2-methyl-2-(methylsulfonyl)butanamide;
4-[4-(4-fluoro-3-methylphenyl)-1H-pyrazol-1-yl]-N-hydroxy-2-methyl-2-(methylsulfonyl)butanamide;
4-[4-(3-fluoro-2-methylphenyl)-1H-pyrazol-1-yl]-N-hydroxy-2-methyl-2-(methylsulfonyl)butanamide;
4-[4-(5-chloropyridin-2-yl)-1H-pyrazol-1-yl]-N-hydroxy-2-methyl-2-(methylsulfonyl)butanamide;
4-[4-(2,4-difluorophenyl)-1H-pyrazol-1-yl]-N-hydroxy-2-methyl-2-(methylsulfonyl)butanamide;
4-[4-(2,5-difluorophenyl)-1H-pyrazol-1-yl]-N-hydroxy-2-methyl-2-(methylsulfonyl)butanamide;
N-hydroxy-2-methyl-2-(methylsulfonyl)-4-[4-(40-92 be)-1H-pyrazol-1-yl]butanamide;
4-[4-(2,3-dihydro-1-benzofuran-5-yl)-1H-pyrazol-1-yl]-N-hydroxy-2-methyl-2-(methylsulfonyl)butanamide;
4-[4-(3-cyano-4-fluorophenyl)-1H-pyrazol-1-yl]-N-hydroxy-2-methyl-2-(methylsulfonyl)butanamide;
4-[4-(3-fluoro-4-methoxyphenyl)-1H-pyrazol-1-yl]-N-hydroxy-2-methyl-2-(methylsulfonyl)butanamide;
N-hydroxy-2-methyl-2-(methylsulfonyl)-4-[4-(3-oxo-2,3-dihydro-1H-inden-5-yl)-1H-pyrazol-1-yl]butanamide;
N-hydroxy-2-methyl-2-(methylsulfonyl)-4-[4-(1-oxo-2,3-dihydro-1H-inden-5-yl)-1H-pyrazol-1-yl]butanamide;
4-[4-(2,3-dihydro-1,4-benzodioxin-6-yl)-1H-pyrazol-1-yl]-N-hydroxy-2-methyl-2-(methylsulfonyl)butanamide;
4-[4-(3-chloro-4-cyanophenyl)-1H-pyrazol-1-yl]-N-hydroxy-2-methyl-2-(methylsulfonyl)butanamide;
4-[4-(3,4-dimethoxyphenyl)-1H-pyrazol-1-yl]-N-hydroxy-2-methyl-2-(methylsulfonyl)butanamide;
4-{4-[4-(1-cyanocyclopropyl)phenyl]-1H-pyrazol-1-yl}-N-hydroxy-2-methyl-2-(methylsulfonyl)butanamide;
N-hydroxy-2-methyl-4-[4-(2-methylquinolin-6-yl)-1H-pyrazol-1-yl]-2-(methylsulfonyl)butanamide;
4-{4-[3-(difluoromethoxy)phenyl]-1H-pyrazol-1-yl}-N-hydroxy-2-methyl-2-(methylsulfonyl)butanamide;
4-[4-(3-aminoisoquinolin-6-yl)-1H-pyrazol-1-yl]-N-hydroxy-2-methyl-2-(methylsulfonyl)butanamide;
N-hydroxy-2-methyl-2-(methylsulfonyl)-4-{4-[4-(1H-pyrazol-3-yl)phenyl]-1H-pyrazol-1-yl}butanamide;
N-hydroxy-2-methyl-2-(methylsulfonyl)-4-{4-[3-(1H-pyrazol-3-yl)phenyl]-1H-pyrazol-1-yl}butanamide;
N-hydroxy-2-methyl-2-(methylsulfonyl)-4-{4-[4-(1,3-oxazol-5-yl)phenyl]-1H-pyrazol-1-yl}butanamide;
N-hydroxy-2-methyl-2-(methylsulfonyl)-4-{4-[4-(1,2-oxazol-5-yl)phenyl]-1H-pyrazol-1-yl}butanamide;
N-hydroxy-2-methyl-2-(methylsulfonyl)-4-{4-[3-(1,2-oxazol-5-yl)phenyl]-1H-pyrazol-1-yl}butanamide;
N-hydroxy-2-methyl-2-(methylsulfonyl)-4-[4-(8-oxo-5,6,7,8-tetrahydronaphthalen-2-yl)-1H-pyrazol-1-yl]butanamide;
N-hydroxy-2-methyl-2-(m ethylsulfonyl)-4-{4-[5-(trifluoromethyl)pyridin-2-yl]-1H-pyrazol-1-yl}butanamide;
N-hydroxy-2-methyl-2-(m ethylsulfonyl)-4-{4-[6-(trifluoromethyl)pyridin-3-yl]-1 H-pyrazol-1-yl}butanamide;

4-[4-(3-cyano-4-ethoxyphenyl)-1H-pyrazol-1-yl]-N-hydroxy-2-methyl-2-(methylsulfonyl)butanamide;

N-hydroxy-2-methyl-4-[4-(2-methyl-1,3-benzothiazol-6-yl)-1H-pyrazol-1-yl]-2-(methylsulfonyl)butanamide;

4-[4-(2-amino-1,3-benzothiazol-6-yl)-1H-pyrazol-1-yl]-N-hydroxy-2-methyl-2-(methylsulfonyl)butanamide;

N-hydroxy-2-methyl-4-{4-[6-(2-methylpropoxy)pyridin-3-yl]-1H-pyrazol-1-yl}-2-(methylsulfonyl)butanamide;

N-hydroxy-2-methyl-4-{4-[4-(1-methyl-1H-pyrazol-5-yl)phenyl]-1H-pyrazol-1-yl}-2-(methylsulfonyl)butanamide;

4-[4-(1-benzyl-1H-imidazol-4-yl)-1H-pyrazol-1-yl]-N-hydroxy-2-methyl-2-(methylsulfonyl)butanamide;

N-hydroxy-2-methyl-4-{4-[4-(3-methyl-1H-pyrazol-5-yl)phenyl]-1H-pyrazol-1-yl}-2-(methylsulfonyl)butanamide;

4-{4-[3-(5-amino-1H-pyrazol-3-yl)phenyl]-1H-pyrazol-1-yl}-N-hydroxy-2-methyl-2-(methylsulfonyl)butanamide;

6-{1-[4-(hydroxyamino)-3-methyl-3-(methylsulfonyl)-4-oxobutyl]-1H-pyrazol-4-yl}-1H-indole-2-carboxamide;

5-{1-[4-(hydroxyamino)-3-methyl-3-(methylsulfonyl)-4-oxobutyl]-1H-pyrazol-4-yl}-1H-indole-2-carboxamide;

N-hydroxy-2-methyl-2-(methylsulfonyl)-4-{4-[3-(trifluoromethoxy)phenyl]-1H-pyrazol-1-yl}butanamide;

4-{4-[1-(4-fluorophenyl)-1H-imidazol-4-yl]-1H-pyrazol-1-yl}-N-hydroxy-2-methyl-2-(methylsulfonyl)butanamide;

N-hydroxy-2-methyl-2-(methylsulfonyl)-4-{4-[4-(1,2,3-thiadiazol-4-yl)phenyl]-1 H-pyrazol-1-yl}butanamide;

4-[4-(2-ethyl-1,3-benzothiazol-6-yl)-1H-pyrazol-1-yl]-N-hydroxy-2-methyl-2-(methylsulfonyl)butanamide;

N-hydroxy-2-methyl-4-{4-[4-(2-methylpyrimidin-4-yl)phenyl]-1H-pyrazol-1-yl}-2-(methylsulfonyl)butanamide;

or a pharmaceutically acceptable salt thereof.

24. The compound according to claim 1, or a pharmaceutically acceptable salt thereof;
wherein
X is $CR^4$; and
Y is N.

25. The compound according to claim 24, or a pharmaceutically acceptable salt thereof;
wherein
$R^1$ is methyl;
$R^2$ is methyl;
$R^3$ is hydrogen;
$R^4$ is hydrogen;
L is a bond;
$R^7$ is $(C_6-C_{12})$aryl; and
$R^8$ is absent.

26. The compound according to claim 24 that is N-hydroxy-2-methyl-2-(methylsulfonyl)-4-(4-phenyl-1H-imidazol-1-yl)butanamide or a pharmaceutically acceptable salt thereof.

27. A pharmaceutical composition comprising a compound or a pharmaceutically acceptable salt thereof according to claim 1 in admixture with at least one pharmaceutically acceptable excipient.

28. A method for treating a bacterial infection in a patient, the method comprising administering a therapeutically effect amount of a compound or a pharmaceutically acceptable salt thereof according to claim 1 to a patient in need thereof.

* * * * *